US005541060A

United States Patent [19]

[11] Patent Number: 5,541,060

[45] Date of Patent: Jul. 30, 1996

Bell et al.

[54] DETECTION OF GLUCOKINASE-LINKED EARLY-ONSET NON-INSULIN-DEPENDENT DIABETES MELLITUS

[75] Inventors: Graeme I. Bell; Markus Stoffel; Jun Takeda; Nathalie Vionnet; Kazuki Yasuda, all of Chicago, Ill.; Simon J. Pilkis, St. James, N.Y.; Habib Zouali, Arcueil, France; Gilberto Velho, Paris, France; Daniel Cohen, Sauigny/Orge, France; Philippe Froguel, Bagnolet, France

[73] Assignee: Arch Development Corporation, Chicago, Ill.

[21] Appl. No.: 872,678

[22] Filed: Apr. 22, 1992

[51] Int. Cl.$^6$ .............................. C12Q 1/68; C12P 19/34

[52] U.S. Cl. .............................. 435/6; 435/91.2; 935/77; 935/78

[58] Field of Search .............................. 435/91, 6, 91.2, 435/6; 536/23, 24.33; 935/77, 78

[56] References Cited

U.S. PATENT DOCUMENTS 4,683,195 7/1987 Mullis et al. .............................. 435/91

FOREIGN PATENT DOCUMENTS

0332435A2 9/1989 United Kingdom .

OTHER PUBLICATIONS

"Analysis of any Point Mutation in DNA. The Amplification Refractory Mutation System (ARMS)", published in *Nucleic Acids Research,* Mar. 2, 1989, pp. 2503–2516, by C. R. Newton, et al.

"Nonsense Mutation in the Glucokinase Gene Causes Early–Onset Non–Insulin–Dependent Diabetes Mellitus", by N. Vionnet, et al., Nature, vol. 356 (6371), Apr. 23, 1992.

"Close Linkage of Glucokinase Locus on Chromosome 7p to Early–Onset Non–Insulin–Dependent Diabetes Mellitus", published in *Nature,* vol. 356, Mar. 12, 1992, pp. 162–164, by Ph. *Froguel,* et al.

"Diabetes Sleuths Find 'Smoking Gun' Gene", published in *Chicago Tribune,* Apr. 23, 1992, p. 2, by Peter Gorner.

"The Amino Acid Sequence of Rat Liver Glucokinase Deduced From Cloned cDNA", published in *The Journal of Biological Chemistry,* vol. 264, Jan. 5, 1989, pp. 363–369, by Teresa L. Andreone, et al.

"Molecular Defects in Diabetes Mellitus", published in *Diabetes,* vol. 40, Apr. 1991, pp. 413–422, by Graeme I. Bell.

"Gene for Non–Insulin–Dependent Diabetes Mellitus is Linked to DNA Polymorphism on Human Chromosome 20g", published in *Proc. Natl. Acad. Sci.,* vol. 88, Feb. 1991, pp. 1484–1488, by Graeme I. Bell, et al.

"Scope and Heterogeneous Nature of MODY", published in *Diabetes Care,* vol. 13, Jan. 1990, pp. 49–64, by Stefan S. Fajans, M.D.

"Engineering of Glucose–Stimulated Insulin Secretion and Biosynthesis in Non–Islet Cells", published in *Proc. Natl. Acad. Sci.,* vol. 89, Jan. 1992, pp. 688–692, by Steven D. Hughes, et al.

"Rat Glucokinase Gene: Structure and Regulation by Insulin", published in *Proc. Natl. Acad. Sci.,* vol. 86, Jul. 1989, pp. 4838–4842, by Mark A. Magnuson, et al.

"Glucokinase Gene Structure", published in *Diabetes,* vol. 39, May 1990, pp. 523–527, by Mark A. Magnuson.

"An Alternate Promoter in the Glucokinase Gene is Active in the Pancreatic Beta Cell", published in *The Journal of Biological Chemistry,* vol. 264, Sep. 25, 1989, pp. 15936–15942, by Mark Magnuson, et al.

"Glucokinase as Glucose Sensor and Metabolic Signal Generator in Pancreatic Beta–Cells and Hepatocytes", published in *Diabetes,* vol. 39, Jun. 1990, pp. 647–652, by Franz M. Matschinsky.

"Detection of Polymorphisms of Human DNA by Gel Electrophoresis as Single–Strand Conformation Polymorphisms", published in *Proc. Natl. Acad. Sci.,* vol. 86, Apr. 1989, pp. 2766–2770, by Masato Orita, et al.

"Rapid and Sensitive Detection of Point Mutations and DNA Polymorphisms Using the Polymerase Chain Reaction", published in *Genomics,* 1989, pp. 874–879, by Masato Orita, et al.

"Cloning and Sequence Determination of Two Alternatively Spliced DNAs", Human Liver Glucokinase Gene: published in *Proc. Natl. Acad. Sci.,* vol. 88, Aug. 1991, pp. 7294–7297, by Yukio Tanizawa, et al.

"Mutations in Insulin–Receptor Gene in Insulin–Resistant Patients", published in *Diabetes Care,* vol. 13, Mar. 1990, pp. 257–279, by Simeon I. Taylor, M.D., et al.

"Lessons Learned from Molecular Biology of Insulin–Gene Mutations", published in *Diabetes Care,* vol. 13, Jun. 1990, pp. 600–609, by Donald F. Steiner, M.D.; et al.

"Primer–directed Enzymatic Amplification of DNA with a Thermostable DNA Polymerase", published in *Science,* vol. 239, Jan. 29, 1988, pp. 487–491, by Randall K. Saiki, et al.

Matsutani, A. et al. (1992, Feb.) Genomics, vol. 12, 319–325.

Textbook of Human Genetics, M. Levitan, Oxford University Press, New York, 1988, p. 292.

*Primary Examiner*—W. Gary Jones
*Assistant Examiner*—Lisa Arthur
*Attorney, Agent, or Firm*—Arnold, White & Durkee

[57] ABSTRACT

The invention relates to the observed tight linkage between DNA polymorphisms in the glucokinase gene (GCK) on the short arm of chromosome 7, and NIDDM in a cohort of sixteen French families having MODY. It further relates to identification of mutations in GCK and their linkage with diabetes in particular families are disclosed. This invention provides the first evidence implicating specific mutations in a gene involved in glucose metabolism in the pathogenesis of NIDDM. The invention further discloses the isolation and characterization of human pancreatic β-cell GCK and a method for searching for mutations that cause early-onset NIDDM. To assess the effect of these mutations on glucokinase activity, a method is disclosed for generating an α-carbon backbone model for human glucokinase based on the crystal structure of the structurally-related yeast hexokinase B. Thus, in its most general sense, the invention relates to a method for detecting a propensity to develop early-onset, non-insulin-dependent diabetes mellitus.

15 Claims, 35 Drawing Sheets

AGGAGGAGCCAGTCCCTGTGGCCTCTGTTCTGACAGTGTCAACCTCAG
CTCCGATGGGCTCCCCTACTGCCTGGCAGACCTGTCCAGCTTTGGACT
AGTGGCTCCACTGTGGAGGGTCTCTGGAGAGTTTACAGCCCTAGATAG
GCTTCCAGACTCACGGGATCCTCTGCTCATCAGAACAGGAGTGTGGGA
GGCGATTGAGTGGTCACCATGGTGATGGGGATGGAGGCTCTTTGCCAC
GACAACCACAGGCCCTCTCAGGAGCACAGTAAGCCCTGGCAGGAGAAT
GAGAGACACAGTCACCTGCAGCCTAATTACTCAAAAGCTGTCCCCAGG
GAGAGAAAGTGCTGAGGACGCCACCCAAGCGCCCAGCAATGGCCCTGC
AGGAGAAACTGTGACTGAACCTCAAACCCCAAACCAGCCCGAGGAGAA

GCCTACTGGGGAAGGCTGAGGGGTCCCAGCTCCCCACGCTGGCTGCTG
CTCGCCCTCCATTGGGCATTCTGGGAGTGTTTGCTTGCCTGTCCCCAA
GCCTTCTGGGGCAGGAAGGCCTACTGCCTGGCAGACCCATCCAGCTTT
TGCCTCCAAGAGCAAGTCCAGACCTGCACCAGCGCGGCCAGGCCCCC
CGCACAAGGCTGAGGAATGGAAGATGGGTAGGCTCTGCACACCCCCTC
TGTCAACTGTTACCCCACATGGGCCTACCCTCCCTTTCTGGCCCTGCC

FIG. 6A

```
CCAGGCTTGTGGGCCAGGTGTACTGTTGTGGTTCAGATTTCAAGGAGATAGTCAGGGCAGGCCGCGCAAAGCC
CTGGCCCTGCGACCTGTCCAGCTTTGGACTCTGGCCCTGCGACCTGGAAGTCAGGCTGCCAAGAGGTCCAGGC
GGGGGTTAGGGATGTGAGATGGTCCCAGGGGCCTGCTCCTGAGCCACGCCAAGCTGCCTGCTCCCTTTCCTCT
GACCCTGAGACACTGCCCCAGGATCTGAACAGGTGGCAAAGGCTTAACAGGCTAGCGTGCACTGTAGTGACAA
CAGTCCCAGTTTTATGCATGGCAGCTCTAATGACAGGATGGTCAGCCCTGCTGAGGCCACTCCTGGTCACCAT
CCCCCACTCCACACCTGGCTGGAGCAGGAAATGCCGAGCGGCGCCTGAGCCCCAGGGAAGCAGGCTAGGATGT
TCACAGAAGGGAGAGGACATTTCCCACTGAATCTGTCTGAAGGACACTAAGCCCCACAGCTCAACACAACCAG
CTGGAGAACATCCAGGCTCAGTGAGGAAGGGTCCAGAAGGGAATGCTTGCCGACTCGTTGGAGAACAATGAAA
CCACATTCTCCCAGGGACCCAGGGCGGGCCTGACCCCTGCGGCGGAGAAGCCTTGGATATTTCCACTTCAGAA
Exon 1a   1                                10                   15
          Met Leu Asp Asp Arg Ala Arg Met Glu Ala Ala Lys Lys Glu Lys
TGCAC     ATG CTG GAC GAC AGA GCC AGG ATG GAG GCC GCC AAG AAG GAG AAG GTAT
CATTCCATGGTTTGTTTGAGCCTCAGAATCTGATTTTATGCACAGGCTCTTTGAGAAGGGTCTTGCCAGGGGT
GGACTCTGGTCCTGCGACCCGGAAGTCAGGCGTCCAAGAGGTC:::::: >8 kb :::::::GGGATCCCCT
TTAGGACCCCCTCCCTGTCCAAGGGCATTTCAGTAAGTGTTCTGTGGCCAAGGCAGCCTGGTGACTTTCTGCC
CTGCTGGGCAGCAATCCCTACCCCATGTTCACAGAGTGTGGCCGGCTGCCCCATGGCTCTGTCCCCGTGGCCC
TCTGACCCCATGGCAGGGGGCAGAGTATTTGAGCAGCCGCCAGCTGAGCCCTTTCAGTGCAGAAGCCCTGGGC
```

FIG. 6B

```
TGCCAGCCTCAGGCAGCTCTCCATCCAAGCAGCCGTTGCTGCCACAGG
               Exon 1b  1
                        Met Ala Met Asp Val Thr
CTACCTCTTAGCCCCTCGGAGAG ATG GCG ATG GAT GTC ACA

TGGGAGAGCAGCACCCAGGGCAGGGCCTTGGTTTTGCAGATTACCAAA
GGCTAGGGCAGCTGTGCCTC:::::: 0.6 kb ::::::CTGCAGCA
GCTGGAATAGACAGTTCCTCAGTCCACATCTGCCAAAGGCGGCACTAG
CATCCTGCCCCTGGCAGCCCTGCCTGACCAGCTCCGCCTCTCCCACTG
                   Exon 1c

CACATCTACCTCTCCAG  CCAGACTCTCCTCTGAACTCGGGCCTCAC
                 10              14
Ser Gln Leu Pro Gln Pro Asn Ser Gln
TCC CAA CTC CCA CAA CCC AAC TCC CAG GTCAGATGGAAC
```

FIG. 6C

CGGGCCTTACGCTCCAAGGCTACAGCATGTGCTAGGCCTCAGCAGGCAGGAGCATCTCTGCCTCCCAAAGCAT 10 16

Arg Ser Gln Ala Gln Thr Ala Leu Thr Leu

AGG AGC CAG GCC CAG ACA GCC TTG ACT CTG GTAAGGGTCACACCAAAGTTAGGGACTTTGCAC

ACTAAGGCTGGGGGCAGGGAAGGCGAGCAGGCTTGGGGCACCTTGGAAGGAGGCACATGGCTTGGGGGTCCT

TCTGCCCAGGGACTGCCCTGGCCCTTGGCATTTCCTCAGGGACCCACAGCTCCACCAGCCGGCCCCTCCCAGT

AAGGCATCCTGCCTTTTTTACTGCGTTCTGGAGGTGGGGTCACAAAGCACTGCTCACTGCATAAAAGGGACAG

CTATCCAACCTGTACACCCTGGTGACCATGTCCAGGCCAGTGGCCTTAAGGACTGTCTCTGTACTGATGGCTC

1

Met Pro Arg Pro Arg

ATGGCCAACTGCTACTTGGAACAAATCGCCCCTTGGCTGGCAGATGTGTTAAC ATG CCC AGA CCA AGA

CTCTTCTTCCCAGGCCCTTCTGTTCCTCTCCTCAGCCCCTCCCACCTCCCTTCAGAATAAGTCTAGACTCTTA

FIG. 6D

```
TCGCTTTCACCAAGCCTGCGCCCAGCATCCCTGCACAGGGATTGTTAG
GACGAAGCAGGGTGCTACAGGACGCTGTGCCACAGGGATATCGTCAGG
CCAGACTCTGCTCTTCTGACTTTCCAGCTGGTTTTACCTGTAGTAAAG


CGTGAGGCCCTCGGTGTGCAGATGCCTGGTGACAGCCCCACCCTGAGG
 20                                          30
Leu Ala Glu Phe Gln Leu Gln Glu Glu Asp Leu Lys
CTG GCA GAG TTC CAG CTG CAG GAG GAG GAC CTG AAG
 50                                          60
His Glu Glu Ala Ser Val Lys Met Leu Pro Thr Tyr
CAT GAA GAG GCC AGT GTG AAG ATG CTG CCC ACC TAC
```

FIG. 6E

```
GACAGCCTGACGCCCTGCTTCCACCCTGCCCCAAGATGCCCTGCTCTGCAG::::: 4.3 kb :::::GG
GACAGAAGCTACTCTGCCCTCTGCTGCTCACCCCTCCAACACGCTGTGGCTGCATTTGTTGAGTGGCTGGTA
TTTGAGAAGATGGTCATCCTGACCCCGGGGTCAGAAGACAGAAGGAGGCCCATGGCGTGTGGGGAGATGCCC
                                                    Exon 2  16
                                                         Val Glu Gln Ile
TCCCCAGCCTACCCCCTCCCCAGCCCGACTGCTCCCATCCCCCTCCCTGTGCAG   GTA GAG CAG ATC
                                      40
Lys Val Met Arg Arg Met Gln Lys Glu Met Asp Arg Gly Leu Arg Leu Glu Thr
AAG GTG ATG AGA CGG ATG CAG AAG GAG ATG GAC CGC GGC CTG AGG CTG GAG ACC
                                      70
Val Arg Ser Thr Pro Glu Gly Ser G(1u)
GTG CGC TCC ACC CCA GAA GGC TCA G GTACCACATGGTAACCGGCTCCTCATCCAGAAGCAGCTGT
```

FIG. 6F

```
GGGCTCAGCCTAGCTGGGAGAAGCACCCCAGGCACTCCCAGACTCACAGCCAGCCCGAGA
TGGTCCGGCCCTGGGGCACTCGGGCTCACCCTGGAGCTGGCAAACCTCAGGAAAACTGGC

CCGGCTCAGTCACCTGGGGCCCACCCAGCCCAAGGCCAGCCTGTGGGTGTCCCTGAGGCT
          80                                        90
Asp Leu Gly Gly Thr Asn Phe Arg Val Met Leu Val Lys Val Gly
GAC CTG GGT GGC ACT AAC TTC AGG GTG ATG CTG GTG AAG GTG GGA
         110                                    120 121
Tyr Ser Ile Pro Glu Asp Ala Met Thr Gly Thr Ala Glu Met
TAC TCC ATC CCC GAG GAC GCC ATG ACC GGC ACT GCT GAG ATG GTGA

ACGGGAGGTGCCACCTGTCTACCAGGGGTGGGAGAGCGGGGGCTGGAGGACCACCCAGC

CCTGGCATTCAGTGGCCAGGTGTTGCAGTGTCCCTGAGGAATAGCTTGGCTTGAGGCCGT
 4    122                             130
      Leu Phe Asp Tyr Ile Ser Glu Cys Ile Ser Asp Phe Leu Asp
CAG   CTC TTC GAC TAC ATC TCT GAG TGC ATC TCC GAC TTC CTG GAC
```

FIG. 6G

```
CAGAATCTCCTGGGGAGCAATGAAGTCCTCGACTTGGCCAGTTCTCACCCTTGGCTCCTC
GTTTTAA:::::: 1.2 kb ::::::TCCCTTGTGCCTTCCCTCCTCCTCTTTGTAATAT
                Exon 3   70
                                   (G)lu Val Gly Asp Phe Leu Ser Leu
GACACACTTCTCTCTGTGCCTTTAG             AA GTC GGG GAC TTC CTC TCC CTG
                                   100
Glu Gly Glu Glu Gly Gln Trp Ser Val Lys Thr Lys His Gln Met
GAA GGT GAG GAG GGG CAG TGG AGC GTG AAG ACC AAA CAC CAG ATG

GCAGCGCAGGGGCCGGGGCAGGGGGCAAGGCATGCAGGATCTCAGGGCCCAGCTAGTCCTG

CTCAGAGGCAGCTGGAGGCCTGGGTGAACAGGACT:::::: 1.7 kb ::::::GACAGG
                                                           Exon
GGGGAGGGCTGCCGGCCAGCGCACCCCCCCATGCCAGATGGTCACCATGGCGTGCATCTTC
             140                                         150
 Lys His Gln Met Lys His Lys Lys Leu Pro Leu Gly Phe Thr Phe
 AAG CAT CAG ATG AAA CAC AAG AAG CTG CCC CTG GGC TTC ACC TTC
```

FIG. 6H

```
                                                   160 161
Ser Phe Pro Val Arg His Glu Asp Ile Asp Lys
TCC TTT CCT GTG AGG CAC GAA GAC ATC GAT AAG GTGGGCCGGGTGGAGG

CCCCATACCCTGTGCTCAGAAGGGAGATCTGGATTCAAATTGTGGCCATGTCACCTGCCA
ACCAGCTATGATCACCCCACTCCAGTGGAAAGAGCAGCTGGCAGTAGGGTGGGGCTCAAA


TG:::::: 0.9 kb ::::::CCCTAGCACCCTGCCTCCAGATATGTTAGCAGCCACGA
                                    180
Lys Ala Ser Gly Ala Glu Gly Asn Asn Val Val Gly Leu Leu Arg
AAG GCC TCA GGA GCA GAA GGG AAC AAT GTC GTG GGG CTT CTG CGA


CCCTGGGCCACCCACCCCAGCACTGCCTGCCTTTCTCCTTGGCTTCCAGCACTGCAGCTT
                        210
Asp Thr Val Ala Thr Met Ile Ser Cys Tyr Tyr Glu Asp His Gln
GAC ACG GTG GCC ACG ATG ATC TCC TGC TAC TAC GAA GAC CAT CAG
```

FIG. 6I

```
GGCAGAAGGCAGATGAGGGGAGGCACAGGCACCCCAGAGGAACTCTGCCTTCAAATGTAGC

CTCTAATGCTGTGGAAAAGAAGCATCACATTAGCTAATTCTGGCTGTGCGCCTTGTGAGGC
CTCAGGCAGCCGGCTCTGGGTCATCAGCCAGTCATGTCACATGCCTATGCTAGTCAGAATG
               Exon 5  162                             170
                       Gly Ile Leu Leu Asn Trp Thr Lys Gly Phe
GGCCTATCTCTCCCCACAG    GGC ATC CTT CTC AAC TGG ACC AAG GGC TTC
             190          193
Asp Ala Ile Lys Arg Arg Gly
GAC GCT ATC AAA CGG AGA GGG GTGAGGGGCACCTGTACCTGCCGGGGGGCTG
           Exon 6  194                     200
                   Asp Phe Glu Met Asp Val Val Ala Met Val Asn
CTGTGCTTCTTGGCAG   GAC TTT GAA ATG GAT GTG GTG GCA ATG GTG AAT
220                            227
Cys Glu Val Gly Met Ile Val G(ly)
TGC GAG GTC GGC ATG ATC GTG G GTAAGGGCTCCTTGCACCCCTGCCCCTTCCAG
```

FIG. 6J

```
ACTGCCGAGGCTCCCTGTGTACAACAGGCTTCAAGGGCCCTGTGGGTGAGGGCCAAACTA

CAAGATGGAAGC:::::: 1.9 kb ::::::GGCAGGAACCAGGCCCTACTCCGGGGCA
                                240
Ala Cys Tyr Met Glu Glu Met Gln Asn Val Glu Leu Val Glu Gly
GCC TGC TAC ATG GAG GAG ATG CAG AAT GTG GAG CTG GTG GAG GGG
                                270
Asp Ser Gly Glu Leu Asp Glu Phe Leu Leu Glu Tyr Asp Arg Leu
GAC TCC GGC GAG CTG GAC GAG TTC CTG CTG GAG TAT GAC CGC CTG

CTCCCCCACAACCCAGGCCCTGGGCGCTCTGGTGCAGCGGCAGATGGAGCCGGGCCATT
```

FIG. 6K

```
CTTAACAACCGGTGATGTCAGAGCAGAGCCTGGTGCTACAGCCTGGGTGGTCTTGGGGTAT
                                         Exon 7  227  Met (F391)
                                                (G)ly Thr Gly Cys Asn
GTGCAGCTCTCGCTGACAGTCCCCCGACCTCCACCCCAG  GC  ACG GGC TGC AAT
            250                                   T       260 Arg (F388
Asp Glu Gly Arg Met Cys Val Asn Thr Glu Trp Gly Ala Phe Gly /390)
GAC GAG GGC CGC ATG TGC GTC AAT ACC GAG TGG GGC GCC TTC GGG
        AM (F8)                             288         A
Val Asp Glu Ser Ser Ala Asn Pro Gly Gln Gln Le(u)
GTG GAC GAG AGC TCT GCA AAC CCC GGT CAG CAG CT GTAAGGATGCCCCC
        T
GCAGATAATGGGCTTGTTTTTAAACAACTCTGGGAAAAGCAAACTGACAATCCGTTCGTA
```

FIG. 6L

AGCTCCATCCCTTCTGCTCAGTCATGACCTGCCCCTGTGAGAGATGAAGGGTTAGT

::::CCTCAGTGGGGAGCACTGGGGCCGGCTCCCGGCTTCCACCTGCATGAGGGGC

Ile Gly Gly Lys Tyr Met Gly Glu Leu Val Arg Leu Val Leu
ATA GGT GGC AAG TAC ATG GGC GAG CTG GTG CGG CTT GTG CTG

Gln Leu Arg Thr Arg Gly Ala Phe Glu Thr Arg Phe Val Ser
CAG CTG CGC ACA CGC GGA GCC TTC GAG ACG CGC TTC GTG TCG

GGCACTGCAGACTTGGTCTCAGGGCGACGCTGAGTCCCAGGCCCGGGGCGCAGGGA

GACGGCTGGCCGGGGCCCCTCCCTGGAGAACGAGAGGCCGCCGCTGGAGGGGGATG

350
Asp Arg Lys Gln Ile Tyr Asn Ile Leu Ser Thr Leu Gly Leu
GAC CGC AAG CAG ATC TAC AAC ATC CTG AGC ACG CTG GGG CTG

FIG. 6M

```
CCCAGTTGTGATGTGATAAGCCCAGACCTCTTTCCTTCCGACAGGTGAT:::: 1.0 kb ::::
                                          Exon 8   288     290
                                                 (Le)u Tyr Glu Lys Leu
CCTCCCTCGTGCCTGCTGATGTAATGGTCCTGCCCTATGTCCAG    G TAT GAG AAG CTC
            310                                         320
Leu Arg Leu Val Asp Glu Asn Leu Leu Phe His Gly Glu Ala Ser Glu
CTC AGG CTC GTG GAC GAA AAC CTG CTC TTC CAC GGG GAG GCC TCC GAG
            340
Gln Val Glu Se(r)
CAG GTG GAG AG GTGTGCGGAGGAGGAGGGTGGGTGCAAAGGGCAGGGGCTGGGGTCGCCCG

CGGGAAACTAGGGCCTGGGGCGGGATTCCGGGCGTGGG::::: 0.5 kb :::::GCTGGGG
                                              Exon 9  340
                                                   (Se)r Asp Thr Gly
GACTGTCGGAGCGACACTCAGCGACCGCCCTACCTCCTCCCGCCCCGCAG C GAC ACG GGC
        360                                      370
Arg Pro Ser Thr Thr Asp Cys Asp Ile Val Arg Arg Ala Cys Glu Ser
CGA CCC TCG ACC ACC GAC TGC GAC ATC GTG CGC CGC GCC TGC GAG AGC
```

FIG. 6N

```
                              380
Val Ser Thr Arg Ala Ala His Met Cys Ser Ala Gly Leu Ala
GTG TCT ACG CGC GCT GCG CAC ATG TGC TCG GCG GGG CTG GCG
                              410
Ile Thr Val Gly Val Asp Gly Ser Val Tyr Lys Leu His Pro
ATC ACT GTG GGC GTG GAT GGC TCC GTG TAC AAG CTG CAC CCC

CTTGCGGTTCCCAAGCTCCAAGATTTCGTAGTCCTCTTCTCGTCCCCCTTGGCCTA
GA:::::: 0.7 kb ::::::TAGAGTCTTCTCGACCCCCTTGGCCTAGATTTGG
                Exon 10  418     420
                          (Se)r Phe Lys Glu Arg Phe His Ala
GGCAGCCCTGCTTCTCTTCTGCCCAG C TTC AAG GAG CGG TTC CAT GCC
                                        450
Glu Glu Gly Ser Gly Arg Gly Ala Ala Leu Val Ser Ala Val
GAG GAG GGC AGT GGC CGG GGC GCG GCC CTG GTC TCG GCG GTG
```

FIG. 60

```
      390                                         400
Gly Val Ile Asn Arg Met Arg Glu Ser Arg Ser Glu Asp Val Met Arg
GGC GTC ATC AAC CGC ATG CGC GAG AGC CGC AGC GAG GAC GTA ATG CGC
418
Se(r)
AG  GTGAGCCCGCCCCGCTCTCTCCCTGGTAAAGTGGGCCCAAAAGCGCGCTCCAAGGTTC
         T
GATTTGGGGGAAGGGTCGACTGCGTGCAGGGCGCCCGGTAATGAATGTGGAGGATGAGGTGGAG
GGGAAGGGTCGACTGCGTGCAGGGCGCCCGGTAATGAATGTGGAGGATGAGGTGGAGGAGGAC
             430                                         440
 Ser Val Arg Arg Leu Thr Pro Ser Cys Glu Ile Thr Phe Ile Glu Ser
 AGC GTG CGC AGG CTG ACG CCC AGC TGC GAG ATC ACC TTC ATC GAG TCG
            460                 465
Ala Cys Lys Lys Ala Cys Met Leu Gly Gln OP
GCC TGT AAG AAG GCC TGT ATG CTG GGC CAG TGA GAGCAGTGGCCGCAAGCGCAG
```

FIG. 6P

GGAGGATGCCACAGCCCCACAGCACCCAGGCTCCATGGGGAAGTGCTCCCCACACG
GGGGAACAGAGCGGGCCTCTTCCCTCAGTTTTTCGGTGGGACAGCCCCAGGGCCCT
ATTTCCCAGAAGGGAGTTGCTCACTCAGGACTTTGATGCATTTCCACACTGTCAGA
CTTCCCTGGGAACTCATCCTGTGTGGGGAGGCAGCTCCAACAGCTTGACCAGACCT
GGCTCAAGAGGCCCAGGGAGCAATGGGAGGGGGCTCCATGGAGGAGGTGTCCCAAG
GGACCCTCGCAGCAGGTGCAAGAGACAGAGCCCCCAAGCCTCTGCCCCAAGGGGCC
CAAGCAGCATTCAGCACACCCCAAGGACAACCCCATCATATGACATGCCACCCTC

FIG. 6Q

TGCTCGCAGCCTGGCGGGGCAGGAGGCCTGGCCTTGTCAGGACCCAGGCCGCCTGCCATACCGCT
AACGGGGGTGCGGCAGGAGCAGGAACAGAGACTCTGGAAGCCCCCACCTTTCTCGCTGGAATCA
GCTGTTGGCCTCGCCTGGGCCCAGGCTCTGGGAAGGGGTGCCCTCTGGATCCTGCTGTGGCCTCA
AGACCTGGGCCAAAAGGGCAGCCAGGGGCTGCTCATCACCCAGTCCTGGCCATTTTCTTGCCTGA
CTTTGAATACCCCCAGAGACCTTTTCTCTCCCATACCATCACTGAGTGGCTTGTGATTCTGGGAT
CACAAAGGGGAGAAGGGCCAGCCCTACATCTTCAGCTCCCATAGCGCTGGCTCAGGAAGAAACCC
TCCATGCCCAACCTAAGATTGTGTGGGTTTTTTAATTAAAAATGTTAAAAGTTTT

FIG. 6R

```
       385            390             395            400             405           410
Hugk   A G L A G V I N R M R E S R S E D V M R I T V G V D G S
Yshkb  C G I A A I C Q K R G - - - - - - Y K T G H I A A D G S
           400            405                      410           415
                                                         β12

       435            440             445            450            455           460
Hugk   E I T F I E S E E G S G R G A A L V S A V A C K K A C M
Yshkb  P I K V V P A E D G S G P G A A V I A A L A Q K R I A E
       450            455             460            465            470           475
          β8                                 α13
```

DETECTION OF GLUCOKINASE-LINKED EARLY-ONSET NON-INSULIN-DEPENDENT DIABETES MELLITUS

Government support under DK-20595 awarded by The National Institutes of Health may provide the government certain rights in this invention.

BACKGROUND OF THE INVENTION

1. Field of the Invention

The invention relates to the discovery of mutant alleles at the glucokinase gene locus on the short arm of human chromosome 7. The invention relates as well to the correlation between these alleles and certain forms of non-insulin dependent diabetes mellitus. In particular, the invention provides methods for detecting subjects with a propensity to develop certain forms of diabetes by virtue of their possession of mutant glucokinase alleles. The invention further provides methods for determining the molecular mechanisms associated with defective glucokinase as these mechanisms relate to substrate/ligand binding by the enzyme.

2. Description of the Related Art

Non-Insulin Dependent Diabetes Mellitus

Non-insulin-dependent or Type 2 diabetes mellitus (NIDDM) is a major public health disorder of glucose homeostasis affecting about 5–7% of the general population. Clinically, NIDDM is a heterogenous disorder characterized by chronic hyperglycemia leading to progressive micro- and macrovascular lesions in the cardiovascular, renal and visual systems as well as diabetic neuropathy. The causes of the fasting hyperglycemia and/or glucose intolerance associated with this form of diabetes are not well understood. Unfortunately, the disease is associated with early morbidity and mortality.

Subtypes of the disease can be identified based at least to some degree on the time of onset of the symptoms. The principal type of NIDDM occurs at a later time of onset, typically at midlife. Early-onset NIDDM or maturity-onset diabetes of the young (MODY) shares many features with the more common form(s) of NIDDM but onset occurs in early life.

GENETIC STUDIES

Maturity-onset diabetes of the young (MODY) is a form of non-insulin dependent (Type 2) diabetes mellitus (NIDDM) that is characterized by an early age at onset and an autosomal dominant mode of inheritance (Fajans 1989). Except for these features, the clinical characteristics of patients with MODY are similar to those with the more common late-onset form(s) of NIDDM.

Although most forms of NIDDM do not exhibit simple Mendelian inheritance, the contribution of heredity to the development of early-onset NIDDM has been recognized for many years (Cammidge 1928) and the concordance of early-onset NIDDM in monozygotic twin pairs (Barnett et al. 1981) indicates that genetic factors play a role in its development. Early-onset NIDDM is thus characterized by its early age of onset (often during childhood), clear mode of inheritance (autosomal dominant), high penetrance (of the symptomology), and ready availability of multi-generational pedigrees for genetic studies.

Clinical, familial, genetic and metabolic studies suggest that early-onset diabetes is a relatively complex disorder with a number of different genes being responsible for its development. Genetic studies have shown linkage between early-onset NIDDM and DNA markers on chromosome 20 (Bell et al. 1991) and with the glucokinase gene (GCK) on chromosome 7 (Froguel et al. 1992; incorporated herein specifically by reference). Whereas the diabetes-susceptibility gene on chromosome 20 has not been identified, GCK is a candidate for the susceptibility gene on chromosome 7. Glucokinase is, therefore, also a candidate for the site of genetic lesions in these families.

GLUCOKINASE

Glucokinase (ATP:D-hexose 6-phosphotransferase, EC 2.7.1.1) is an enzyme which catalyzes the formation of glucose-6-phosphate from glucose and may be involved in the regulation of insulin secretion and integration of hepatic intermediary metabolism (Matchinsky 1990). It is expressed only in liver and pancreatic β-cells and plays a key role in the regulation of glucose homeostasis.

In the hepatocyte, the phosphorylation of glucose by glucokinase facilitates the uptake and metabolism of glucose by maintaining a gradient for glucose transport into these cells thereby regulating hepatic glucose disposal, In β-cells, glucokinase is believed to comprise part of the glucose-sensing mechanism and to be involved in the regulation of insulin secretion.

In the rat, glucokinase is encoded by a single-copy gene that has 11 exons. The glucokinase transcripts expressed in β-cells and liver have unique 5'-ends because of the presence of tissue-specific promoters and first exons termed exons 1a and 1b, respectively. The two transcripts share exons 2–10. Since translation is initiated within exon 1, the sequence of amino acids 1–15 of the hepatic and β-cell glucokinase isoforms differ.

The sequences of cDNAs encoding the β-cell and hepatic isoform of human glucokinase have also been reported (Tanizawa et al. 1991; Nishi et al. 1992) and like the corresponding rat proteins, the sequences of the two isoforms differ at their $NH_2$-termini. The exon-intron organization of the rat gene has been previously reported (Magnuson 1990).

Since an understanding of the molecular basis of NIDDM may elucidate the mechanisms controlling glucose homeostasis and facilitate the development of new therapeutic strategies, studies are needed to identify diabetes-susceptibility genes. Moreover, methods of detecting individuals with a propensity to develop such diseases are needed. Where possible, the molecular mechanism underpinning the genetic lesion should be determined in order to allow diagnosis and specifically-directed therapy.

SUMMARY OF THE INVENTION

The inventors have observed tight linkage between DNA polymorphisms in the glucokinase gene (GCK) on the short arm of chromosome 7, and NIDDM in a cohort of sixteen French families having MODY (Froguel et al. 1992). In the present invention, identification of mutations in GCK and their linkage with diabetes in particular families are disclosed. This invention provides the first evidence implicating specific mutations in a gene involved in glucose metabolism in the pathogenesis of NIDDM.

The identification of these nonsense and missense mutations confirms that genetic variation in glucokinase can cause dominantly-inherited early-onset NIDDM. The identification of mutations in glucokinase, a protein that plays an important role in hepatic and β-cell glucose metabolism, also indicates that early-onset NIDDM may be a disorder of carbohydrate metabolism. Moreover, these results suggest that studies of other proteins involved in the regulation of glucose metabolism may lead to the identification of other diabetes-susceptibility genes.

The invention further discloses the isolation and characterization of genomic human pancreatic β-cell GCK and a method for searching for mutations that cause early-onset NIDDM. To assess the effect of these mutations on glucokinase activity, a method is disclosed for generating an α-carbon backbone model for human glucokinase based on the crystal structure of the structurally-related yeast hexokinase B, This model suggests that certain of the mutations may alter binding of ATP and glucose.

In its most general sense, the invention relates to a method for detecting a propensity to develop early-onset, non-insulin-dependent diabetes mellitus. This method relies on the fact that mutations in a glucokinase gene giving rise to a defective glucokinase gene product have been correlated by the inventors with the disease. It will be understood by those of skill in the art, given the disclosure of the invention that such mutations do indeed cause discernible lesions in the glucose metabolism of a subject, that a variety of methods may be utilized to detect a propensity for the disease.

In particular, methods may be applied to determine whether one or more of the same or similar mutant alleles are found in the DNA of a suspected individual. Alternatively, methods may be applied to the glucokinase enzyme from the affected individuals to determine its similarity to the wild type enzyme. Whatever approach is used to detect variant glucokinase, the discovery that specific genetic lesions in the glucokinase gene exist and are correlated to specific metabolic disorders in glucose metabolism will facilitate the diagnosis of similar mutations in other individuals.

It is important to note in this regard, however, that many forms of diabetes, including other forms of NIDDM, have not yielded such ready explanations as disclosed in the present invention as to MODY mutants. To the contrary, other forms of diabetes appear to be related to complex interactions which may or may not involve mutations in the glucokinase gene.

Thus, more specific methods are disclosed for detecting in a subject a propensity to develop early-onset, non-insulin-dependent diabetes mellitus. One such method comprises first selecting a technique capable of detecting nucleotide changes in a DNA sequence encoding at least a portion of a glucokinase gene. The technique can be any such technique known to those of skill in the art, however, it should be a technique capable of at least detecting single nucleotide changes including deletions additions, and substitutions in the nucleotide sequence.

While a number of exemplary mutations in the glucokinase gene are discussed herein, the methods of the invention are not limited only to these mutations. It will be understood by the skilled practioner that the methods of the invention are capable of detecting any such mutations in the glucokinase gene. It is believed by the present inventors that the muber of such mutations correlating to MODY will be limited to relatively few. However, given the teachings of the present invention that early-onset NIDDM is linked tightly at least to the glucokinase gene locus, in light of the methods taught by the present invention, the skilled practioner is provided with ample teachings to characterize other such glucokinase mutations all of which would fall within the scope of the present claims.

The method next provides for obtaining DNA of a subject to be tested for the propensity. The DNA to be obtained and tested may be so obtained using any of a number of techniques known well to those of skill in the art. Preferably, however, the DNA will be obtained by means such as those taught in references such as Sambrook et al. (1989) Molecular Cloning: A Laboratory Manual, pp. 9.14–9.23. More preferably, the isolation techniques will be similar to those taught in Bell et al. (1981) and may be accomplished in automated means such as by use of an Applied Biosystems 340A Nucleic Acid Extractor.

The method next provides for applying the method capable of detecting at least single nucleotide changes to the DNA of the subject being tested for the propensity. Such a test may be carried out singly or it may be carried out using known standards such as by using similar DNA tests on the DNA of known normal subjects. In either case, the method last provides for determining whether at least one nucleotide change has occurred glucokinase gene. The nucleotide changes which are to be detected include changes as small as a single nucleotide in addition to, deleted from, or altered in the wild type glucokinase gene. Wild type glucokinase is defined for purposes of the invention as the principal gene sequence and resulting amino acid sequence depicted in FIG. 6A, FIG. 6B, FIG. 6C, FIG. 6D, FIG. 6E, FIG. 6F, FIG. 60, FIG. 6H, FIG. 6I, FIG. 6I, FIG. 6K, FIG. 6L, FIG. 6M, FIG. 6N, FIG. 6O, FIG. 6P, FIG. 6Q, FIG. 6R.

The methods of the invention are particularly useful when applied to determine propensities of subjects to the early-onset, non-insulin-dependent diabetes mellitus subtype known as maturity-onset-diabetes of the young.

The methods of the invention may be carried out by utilizing single strand conformation polymorphisms (SSCP). SSCP is a method capable of detecting at least single nucleotide changes in the DNA sequence encoding at least a portion of the glucokinase gene which first comprises isolating the DNA of the subject to be tested for the propensity by any of the techniques described herein or known to those of skill in the art. Next, the method provides for selecting a pair of primers capable of amplifying an exon sequence of the glucokinase gene when used in conjunction with a polymerase chain reaction. Exons of the glucokinase gene may be identified by reference to any of the known genomic sequences for glucokinase genes. Preferably, however, the exons will be identified by comparison to the human pancreatic β-cell glucokinase sequence shown in FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R. Next the method provides for contacting the DNA of the subject to be tested for the propensity with the pair of primers selected and for carrying out the polymerase chain reaction with the DNA and pair of primers to create amplification products. The method then provides for electrophoresing the amplification products to produce an electrophoretic pattern and analyzing the electrophoretic pattern in order to detect at least one nucleotide change. In particular, and as will be apparent in the examples to follow, detection of the variations is easily provided for by the addition of at least one additional electrophoretic band migrating more slowly than the single band found in normal allele samples.

The methods of the invention may also be used with any number of other techniques capable of detecting at least single nucleotide changes in a DNA sequence. The detection of the presence of at least one nucleotide variation may in certain special situations, be achieved by detection of a point mutation which creates or destroys a restriction site (for example, that situation as found in certain alleles of sickle cell anemia). In such a situation, the restriction enzyme may be employed either before or after amplification (Chehab et al. 1987). Other allele-specific techniques of use herein include the techniques described by Kan and Dozy (1978), Rubin and Kan (1985), Conner et al. (1983), Kidd et al. (1983), Lee and LeMaistre (U.S. patent application Ser. No. 448,118, filed Dec. 11, 1989 or Piratsu, et al. (1983). Of particular utility, however, may be the techniques described in European Patent Publication Nos. 237,362 and 332,435, since far fewer steps are required in order to detect variations in the mutant alleles.

Allele-specific detection of mutants is particularly useful with regard to the specific mutations disclosed by this invention. Thus, the methods of the invention may be used to detect the single nucleotide change in the DNA sequence encoding the glucokinase gene from C to T causing an alteration from threonine to methionine at amino acid position 228 of the glucokinase gene sequence of FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R. Similarly, the methods of the invention may be used to detect the single nucleotide changes, in the DNA sequence encoding the glucokinase gene where: (1) a change from G to A causes an alteration from glycine to arginine at amino acid position 261 of the glucokinase gene sequence of FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R; (2) a change from G to T causes an alteration from glutamate to an amber nonsense condon at amino acid position 279 of the glucokinase gene sequence of FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R; (3) a change from G to C causing an alteration from glucine to arginine at amino acid position 299 of the glucokinase gene sequence of FIG. 6A, FIG. 6B, FIG. 6C, FIG. 6D, FIG. 6E, FIG. 6F, FIG. 60, FIG. 6H, FIG. 6I, FIG. 6J, FIG. 6K, FIG. 6L, FIG. 6M, FIG. 6N, FIG. 6O, FIG. 6P, FIG. 6Q, FIG. 6R; (4) a change from G to A causing an alteration from glutamate to lysine at amino acid position 300 of the glucokinase gene sequence of FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R; (5) a change from G to C causing an alteration from glutamate to glutamine at amino acid position 300 of the glucokinase gene sequence of FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R; and, (6) a change from T to C causing an alteration from leucine to proline at amino acid position 309 of the glucokinase gene sequence of FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R.

The methods of the invention are of particular utility when used in conjunction with a pair of primers selected from the pairs of primers of Table 3. As can be seen in that table, pairs of primers are provided for each of the exon sequences which comprise the genomic DNA sequence encoding human pancreatic β-cell glucokinase. Since the homology is almost identical between the hepatic and pancreatic isoforms, such primers will also find utility in probing the hepatic genes as well.

The methods of the invention are, therefore, applicable where the DNA sequence encoding at least a portion of a glucokinase gene is a DNA sequence encoding an hepatocyte-derived glucokinase or a pancreatic β-cell-derived glucokinase. In particular, since the diagnosis of such diseases is of paramount importance in human disease, the methods of the invention will find their chief usefulness in probing the hepatocyte- or pancreatic β-cell-derived glucokinase of humans.

A method is also disclosed for assessing the molecular mechanism by which a mutant allele of a glucokinase gene may affect glucokinase activity. This method will find particular utility in determining the effects of mutations on glucokinase activity.

The method involves first structurally aligning the amino acid sequences of yeast hexokinase with the mutant allele of the glucokinase gene. This structural alignment is carried out as described in detail below and places the locus of the mutation on a carbon backbone of the hexokinase amino acid sequence. Next, the method provides for determining a site along the allele of the glucokinase amino acid sequence which confers the propensity to develop early-onset, non-insulin dependent diabetes mellitus as is accomplished in the methods described above. After the mutant locus is known, the method provides for locating where the mutant locus is structurally aligned with the yeast hexokinase amino acid sequence. Where the mutant locus is closely aligned with amino acid residues known to affect one or another ligand binding of a ligand to hexokinase, a determination is then made as to whether or not the site occurs in a region of the hexokinase amino acid sequence which would be likely to reduce the ability of the glucokinase to bind the ligand. The ligands of particular interest are ATP and glucose. This method can be refined when the atomic structure of human glucokinase has been determined. It will be understood by those of skill in the art of protein structure that as more refined molecular data is obtained on the atomic structure of human glucokinase, additional refinements in the method as they apply to sites of binding of ligands/substrates will be possible.

The variety of methods described above may be incorporated into kits for the purposes of diagnosing propensities to develop early-onset NIDDM. Thus, a kit for detecting the presence or absence of at least one variant nucleotide in the nucleic acids encoding glucokinase contained in a sample may comprise at least one pair of primers selected from the pairs of primers of Table 3 along with each of four different nucleoside triphosphates and an agent (such as any of a number of commercially available DNA polymerases as identified herein) for the polymerization of the nucleoside triphosphates. Where more than one set of primers is selected, separate receptacles for aliquots of the sample DNA will be provided for separate reactions and analyses. Of particular utility will be such kits containing primers directed to allele-specific amplification based on the mutant sequences giving rise to genetic polymorphisms responsible for MODY phenotypes.

BRIEF DESCRIPTION OF THE DRAWINGS

FIG. 3A shows SSCP analysis of exon 7 of GCK from a member of kindred F8 with early onset NIDDM (1496) and a normal relative (1240). FIG. 3B shows the nucleotide sequence at the site of the mutation in the mutant and normal allele, respectively.

FIGS. 6A–6R show the partial sequence of the human glucokinase gene. Nucleotide and predicted amino acid sequences are shown. The number of amino acids at the beginning and the end of the exon is noted. Approximate sizes of the introns are indicated. The mutations in exon 7 and the polymorphism in intron 9 are shown in bold-face type.

FIG. 8A. Sequences of point mutation of subject 2070, kindred F391, having a C→T transition producing a Thr→Met mutation in residue 228. Sequences were obtained after subcloning PCR amplified fragments into M13mp18 and dideoxynucleotide sequencing. Sequences shown here represent the antisense orientation. FIG. 8B. Region of the missense mutation of individual 2044, kindred F388. The G→A substitution leading to a Gly→Arg mutation in residue 261 is indicated.

FIGS 9B–9I. Model for human glucokinase. FIG. 9A1–FIG. 9A2, FIG. 9A, FIG. 9B, FIG. 9C, FIG. 9D, FIG. 9E, FIG. 9F, FIG. 9G, FIG. 9H. Preliminary structural alignment of amino acid sequences of human glucokinase (Hugk) and yeast hexokinase B (Yshkb) based upon placing deletions and insertions between the secondary structural elements in the crystal structure of yeast hexokinase B. The single letter amino acid abbreviations are used. Identical residues are shown in black boxes, and similar in shaded boxes. The similar residues are from the analysis of Rasler et al. (1988) *J. Mol. Biol.* 204:1019–1029. The 13 α-helices and β-strands are indicated above the sequences. The small arrows indicate the positions of introns in the human glucokinase gene.

FIG. 9I. The α-carbon backbone of yeast hexokinase B (grey strands) is shown and is predicted to represent a structural model for glucokinase. The glucose molecule (dark grey balls) was extracted from the inhibitor OTG present in the crystal structure of hexokinase B. The glucokinase mutations: T228M, G261R and E279AM (this mutation produces a truncated protein) are indicated.

COMPLIANCE WITH 37 C.F.R. 1.821(f)

Figure 1:
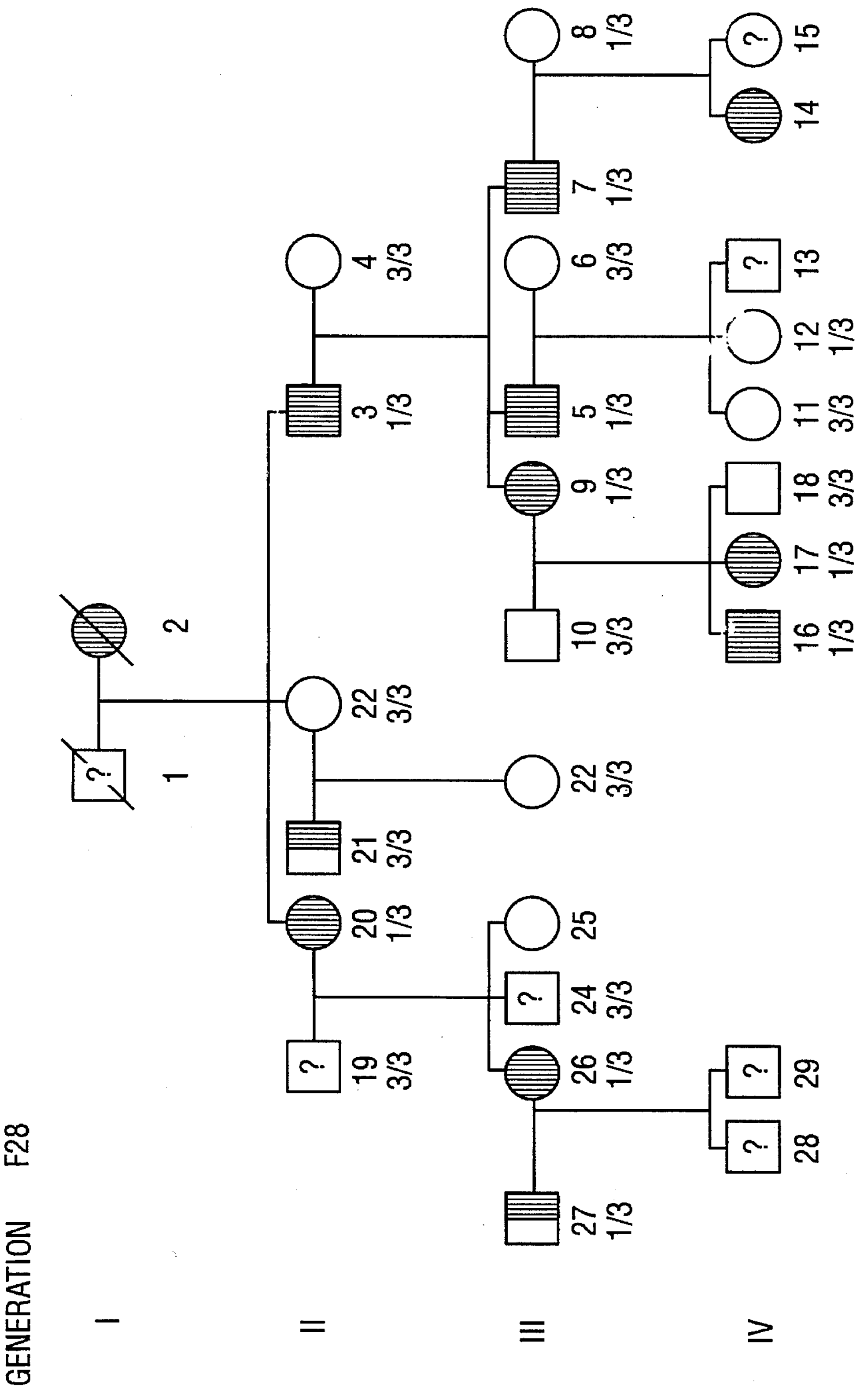
FIG. 1. F28 MODY pedigree. Affected and unaffected individuals are represented by closed and open symbols, respectively, NIDDM by half-closed symbols and untested individuals by question marks. Identification number (first line) and GCK-1 genotype (second line) are shown below each individual.

The content of the paper and computer readable copies containing the Sequence Listings are the same.

DESCRIPTION OF PREFERRED EMBODIMENTS

Nucleic Acid Hybridization Embodiments

In certain aspects, the DNA sequence information provided by the invention allows for the preparation of relatively short DNA (or RNA) sequences having the ability to specifically hybridize to gene sequences of the selected glucokinase gene. In these aspects, nucleic acid probes of an appropriate length are prepared based on a consideration of the selected glucokinase sequence. The ability of such nucleic acid probes to specifically hybridize to the glucokinase gene sequences lend them particular utility in a variety of embodiments. Most importantly, the probes can be used in a variety of assays for detecting the presence of complementary sequences in a given sample. However, either uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 14 to 40 or so long nucleotide stretch of the glucokinase sequence, such as that shown in FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained, longer hybridizing molecules may be used. One will generally prefer to design nucleic acid molecules having gene-complementary complementary stretches of 14 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, herein incorporated by reference, or by introducing selected sequences into recombinant vectors for recombinant production.

Accordingly, the nucleotide sequences of the invention may be used for their ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate glucokinase coding sequences for related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator known in the art, including radioactive, enzymatic or other ligands, such as avidin/biotin, which are capable of giving a detectable signal. In preferred embodiments, one will likely desire to employ an enzyme tag such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

EXAMPLES

Examples have been included in, order to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

Example I

FRENCH FAMILY MODY LINKAGE

Although clinical and metabolic profiles of families with maturity-onset diabetes of the young (MODY) are diverse (Fajans 1989), most MODY patients present a decreased insulin response to glucose, suggesting a primary pancreatic β-cell defect (Fajans 1990). Genes whose products seem to be involved in insulin secretion (such as liver or pancreatic β-cell glucose transporter (GLUT2) and glucokinase (GCK), the key enzyme of glucose metabolism in liver and β-cells) are candidate genes for MODY (Unger 1991; Chanson et al. 1991). To determine the genetic regions involved, the inventors tested these candidate genes as well as a candidate region: one gene responsible for MODY has been mapped to the long arm of chromosome 20 in one large American pedigree (lodscore=5.25; recombination fraction=0.00) (Bell et al. 1991) on the basis of its cosegregation with a polymorphic AluVpA region in the adenosine deaminase gene (ADA).

Figure 2A:
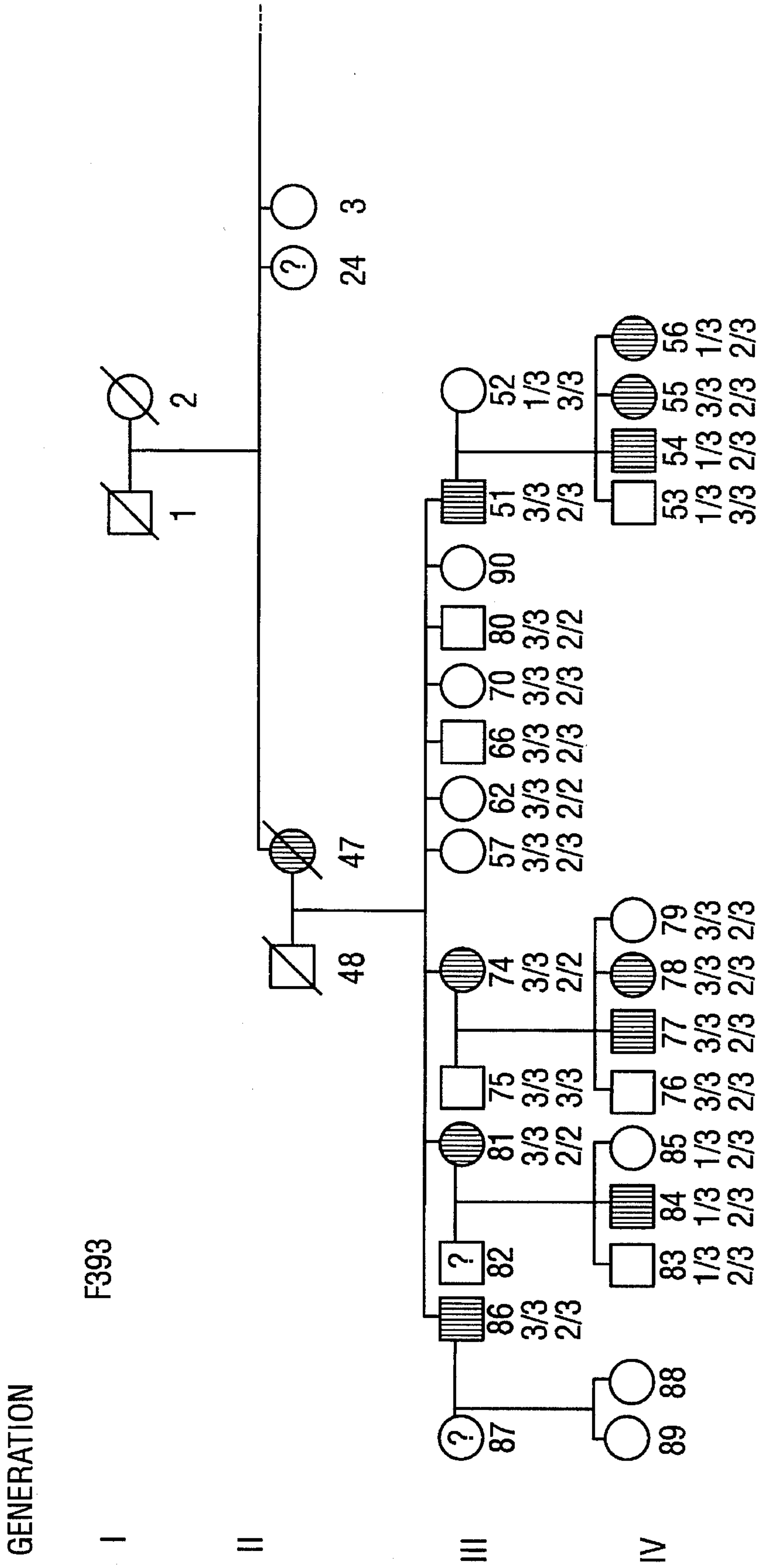
FIGS. 2A and 2B. F393 MODY pedigree. Affected and unaffected individuals are represented by closed and open symbols, respectively, and untested individuals by question marks. Identification number (first line), GCK-1 and GCK-2 genotypes (second and third lines, respectively) are shown below each individual.
Figure 2B:
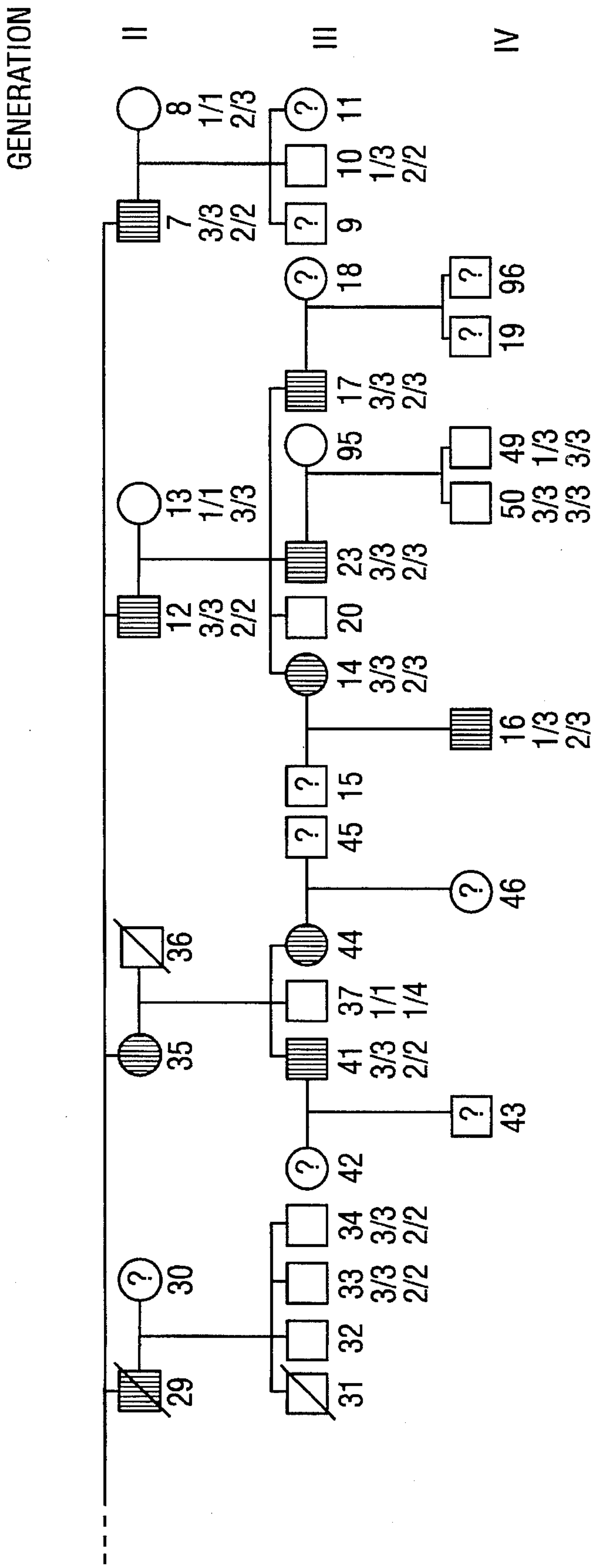

The inventors collected genealogical information and clinical data from 16 French MODY families (for pedigrees, see figures below) ascertained by presence of NIDDM in three consecutive generations (for all but one family in which the older generation was not available), and at least two patients diagnosed before 25 years of age (Table 1, and FIGS. 1 and 2). Of the 304 individuals examined clinically, 125 were considered affected. Those individuals showed either a plasma glucose concentration higher than 7.8 mmol/l, 2 h after an oral glucose per liter load (glucose intolerance according to WHO (World Health Organization) criteria), or a fasting plasma glucose higher than 6.1 mmol/l in two separate measurements. The latter criteria represent values higher than 3 standard deviations above the mean of the normal population (Multicentre Study 1983) and have been used in previous studies (O'Rahilly et al. 1988). Of the 125 affected individuals, 33% presented characteristics of clinical diabetes according to WHO criteria, namely fasting plasma glucose higher than 7.8 mmol/l, or treatment with hypoglycemic agents with previously documented hyperglycemia at this level. Most diabetic subjects had fasting insulinemia in the same range as the normoglycemic relatives but showed a decreased insulin response to an oral glucose load.

Genotypes for the GCK, GLUT2 and ADA loci were obtained as described in Tables 1 and 2. For linkage analysis the inventors used LINKAGE programs (Lathrop et al. 1985) assuming an autosomal dominant pattern of inheritance under a previously defined segregation model (O'Rahilly & Turner 1988) as described in Table 1. Lodscores were negative in all families characterized for GLUT2, whereas ADA gave positive, but nonsignificant evidence of linkage (lodscore >1) in one family, and negative values in 12 families.

By contrast, the maximum lodscore for the GCK locus was 11.6 over all families for recombination fraction=0.01 (Table 2). One family had a maximum lodscore of 5.9, and three others had lodscores >2. the maximum lodscore for GCK were negative in two families, and a test for linkage heterogeneity with the program HOMOG version 3.1 (ref. 14) was significant (P=0.0003), suggesting that one or several other loci, not linked to GCK, may be responsible for MODY in some of our families. The maximum likelihood recombination estimate with GCK is 0.00 (0.00–0.05 one-lod-unit support interval) in the linked category of families. The proportion of families in which the disease is linked to GCK was estimated to be 0.8 (0.45–0.95 one-lod-unit support interval). These results were not sensitive to changes in the model assumed for inheritance of the MODY phenotype, as described in Table 1.

The maximum lodscore was found at a recombination fraction of 0.00 in all but one of the 14 families with positive lodscore. Inspection of the data for family F8, which had a maximum lodscore of 2.23 at a recombination fraction of 0.04, revealed a single diabetic individual who did not inherit the allele segregating with the disease in this family. Several arguments suggest that this person presents a different type of diabetes: (1) she is obese (most MODY patents have normal body mass index); (2) she has a more severe disease; (3) a later age of onset of diabetes (52 years); and (4) none of her four children or four grandchildren, all older than 20, is affected. If this individual's affected status is considered as unknown, the maximum lodscore for the family becomes 3.54 at a recombination fraction of zero.

Two large families (F213 and F30) exhibited negative lodscores with GCK. In one of these (F213), patents were found to have an unusual glycemic profile in which fasting blood glucose was normal, whereas 2-h post-glucose values were consistently in the pathological range. This family also had lower penetrance (20–30%) in each generation, and age-of-onset after 40 years in all but two diabetics (onset 15 and 16 years of age). Family F30, which also had a negative lodscore for GCK, gave a lodscore of 1.14 with ADA (Table 1). Families with lodscores >2 with GCK, did not show linkage to ADA. These results suggest that MODY is genetically heterogenous, with at least two or more loci implicated in the disease. But the majority of families in the inventor's sample show evidence of linkage to GCK, suggesting that this gene, or another closely linked locus, is principally predisposing for the disease.

These results provide strong support for the involvement of glucokinase in some forms of NIDDM. Hyperglycemia associated with NIDDM results from an interplay between impaired insulin secretion and peripheral or hepatic insulin resistance (Defronzo 1988). Neither the mechanisms of this interplay, nor the potential primary role of each component were well understood. Glucokinase has an important role in the regulation of pancreatic insulin secretion in response to glucose and in the uptake of glucose in the liver (Meglasson & Matschinsky 1984; Matschinsky 1990). The key role of glucokinase at the beginning of the glycolytic pathway, and the regulation of this enzyme by glucose in the β-cells and by insulin in the liver, may constitute an important feedback loop for maintaining glucose homeostasis (Magnuson & Shelton 1989). Therefore, a defect in glucokinase activity has been proposed as contributing to aberrant glucose metabolism in NIDDM (Matschinsky 1990).

These results strongly suggest that mutation(s) in the glucokinase locus on chromosome 7p might predispose individuals in these families in NIDDM with early age of onset. Alterations in the structure, function and regulation of β-cell and liver glucokinase could have a major influence on the glucose homeostasis of the organism. Hence, glucokinase was suggested to be an interesting pharmacological target.

In view of the difficulties of assaying the in vivo activity of glucokinase in humans, it is important to find more informative markers for this region so that the remaining informative families can be characterized with respect to this locus. But for a definitive demonstration that this gene product is involved in this pathology, the predisposing mutation(s) had to be identified (Froguel et al. 1992).

TABLE 1

Characteristics of the 16 French MODY families

| Family number | Total number of subjects | Number of diabetic subjects | ADA lodscore (θ = 0.00) | ADA lodscore (θ = 0.05) | Marker 66 lodscore (θ = 0.00) | Marker 66 lodscore (θ = 0.05) | GLUT2 lodscore (θ = 0.05) |
|---|---|---|---|---|---|---|---|
| F8 | 36 | 16 | −4.86 | −1.29 | −5.92 | −1.85 | −4.45 |
| F28 | 21 | 8 | −2.97 | −0.92 | −1.80 | 0.32 | −2.23 |
| F30 | 17 | 6 | 1.14 | 1.24 | 1.28 | 1.18 | −1.04 |
| F51 | 103 | 39 | −16.36 | −9.89 | n.d. | n.d. | −13.62 |
| F85 | 11 | 5 | −1.89 | −0.99 | −0.01 | −0.01 | −1.11 |
| F213 | 16 | 4 | −2.76 | −1.62 | −1.84 | −1.18 | −0.98 |
| F253 | 7 | 2 | 0.97 | 0.89 | −0.02 | 0.00 | −0.53 |
| F313 | 9 | 2 | −2.69 | −0.27 | −0.95 | −0.81 | −1.65 |
| F331 | 8 | 3 | −2.07 | −1.44 | −1.98 | −0.47 | −1.54 |
| F386 | 6 | 3 | 0.54 | 0.49 | 0.00 | 0.99 | n.d. |
| F387 | 6 | 4 | −0.50 | −0.37 | −3.66 | −1.75 | n.d. |
| F388 | 7 | 4 | −1.13 | −0.45 | −1.47 | −0.76 | n.d. |
| F391 | 6 | 4 | −1.11 | −0.43 | 0.00 | 0.00 | n.d. |
| F392 | 7 | 5 | −1.05 | −0.40 | −1.35 | −0.65 | n.d. |
| F393 | 38 | 17 | −10.47 | −2.93 | −6.11 | −0.51 | n.d. |
| F397 | 6 | 3 | 0.55 | 0.51 | 0.00 | 0.00 | n.d. |

Lodscores for diabetes were obtained versus the ADA AluVpA/Pst1 haplotype and the IP20M66 microsatellite on chromosome 20 q, and versus GLUT2 EcoR1/Taq1/poly$(CA)_{15}$ microsatellite haplotype. Families were recruited in France in 1990–1991 through a multimedia campaign, Froguel, Ph. Diabetologia 34, 685 (1991). Families with diabetic members in at least three consecutive generations, autosomal dominant transmission of NIDDM, and several diabetic members diagnosed before 25 year of age, were considered as MODY. Fajans, S. S. Diabetes Care 13, 49–64 (1990). The polymorphis AiluVpA region of the ADA gene was amplified in a polymerase chain reaction (PCR) with a pair of oligonucleotides primers OL3 and OL4 as described. Rvonomou, R. P. et al Proc. Natn. Acad. Sci. USA 87, 2951–2954 (1990). On amplification, eight alleles were identified with sizes ranging from 180 to 208 base pairs (bp). The ADA intron 2 restriction fragment length polymorphism (Pst1) was studied by Southern blotting, and was detected by a genomic probe which revealed two alleles of 3.5 kilobases (kb) and 1.6 kb. Tzail, S. et al Am. J. hum. Genet. 44, 864–8975 (1989). Marker IP20M66 on chromosome 20 q is a $(CA)_{11}$ microsatellite Hazan. J., J. Genomics, in press, situated at 5 centimorgans (cMO from ADA locus (K. S. Xiang and G. I. Bell, unpublished results). It was detected by PCR (oligomers 66A, 5'-TGCACACCCATGTACACAGACTC-3' and 66 M, 5'-GCCCAGGTCTCCAACTCTCC-3'). All primers were custom synthesized by GENSET (France). PCR was done by initially denaturing genomic DNA for 5 min at 94° C., then using 30 cycles of 30 s denaturation at 94° C., 30 s annealing at 68° C., 30 s extension at 72° C. Unlabelled PCR products were electrophoresed on 5% denaturating polyacrylamide sequencing gel, and passively blotted on a nylon membrane Hybond $N^+$ (Amersham). The filters were then hybridized with one of the two amplification primers [α-$^{32}$P]dCTP-labelled by terminal transferase (Boehringer Mannheim). After hybridization (3 h) the filters were washed and autoradiographed for 1–2 h. The results showed an eight-allele polymorphism (the frequency alleles) in the 1988 –220 bp range. The GLUT2 EcoRI and Taq1 RFLPs were studied by Southern blotting, and were detected by a complementary DNA probe as described. Matsutani, A. et al Diabetes 39, 534–542 (1990); Froguel, Ph. et al D. Nucleic Acids Res. 19, 5799 (1991). The GLUT2 microsatellite was detected as described Froguel, Ph. et al. Nucleic Acids Res. 19, 3754 (1991). The lodscores for both sexes were computed together ($\theta_{male} = \theta_{female}$). We assumed a population prevalence of the MODY gene of 0.0001, an age-related penetrance of 0.30 for individuals below 10 years old, of 0.65 between 10 and 20 years old, and 0.90 for subjects older than 20 years, and 1% phenocopy frequency. Results were unaffected by changes in the genetic models (modification of full or lower penetrances, changes in gene frequency and phenocopy frequency, subjects with impaired fasting lucose <7.8 $mmoll^{-1}$ considered as unknown).

TABLE 2

Lodscores for the MODY gene in 16 pedigrees versus the glucokinase microsatellite tandem repeats localized to chromosome 7 p (refs 26, 27)

| Recombination fraction | 0.00 | 0.01 | 0.02 | 0.03 | 0.04 | 0.05 | 0.10 | 0.20 | 0.30 | 0.40 |
|---|---|---|---|---|---|---|---|---|---|---|
| Total Lodscore | 11.59 | 11.63 | 11.60 | 11.54 | 11.46 | 11.33 | 10/67 | 8.40 | 5.58 | 2.58 |
| F8 | 2.03 | 2.14 | 2.19 | 2.22 | 2.23 | 2.23 | 2.12 | 1.65 | 1.06 | 0.47 |
| F28 | 2.18 | 2.14 | 2.10 | 2.06 | 2.02 | 1.97 | 1.75 | 1.28 | 0.78 | 0.31 |
| F30 | −2.21 | −1.99 | −1.82 | −1.69 | −1.57 | −1.47 | −1.10 | −0.65 | −0.35 | −0.15 |
| F51 | 5.89 | 5.77 | 5.65 | 5.53 | 5.41 | 5.29 | 4.69 | 3.50 | 2.30 | 1.09 |
| F85 | 0.89 | 0.87 | 0.85 | 0.83 | 0.81 | 0.78 | 0.76 | 0.74 | 0.72 | 0.03 |
| F213 | −2.68 | −2.65 | −2.61 | −2.54 | −2.45 | −2.34 | −1.74 | −0.88 | −0.39 | −0.11 |
| F253 | 0.05 | 0.05 | 0.05 | 0.05 | 0.05 | 0.04 | 0.04 | 0.04 | 0.04 | 0.00 |
| F313 | 0.46 | 0.44 | 0.42 | 0.41 | 0.39 | 0.37 | 0.35 | 0.34 | 0.32 | 0.01 |
| F331 | 0.28 | 0.27 | 0.27 | 0.27 | 0.26 | 0.26 | 0.23 | 0.19 | 0.13 | 0.07 |
| F386 | 0.28 | 0.28 | 0.27 | 0.27 | 0.26 | 0.26 | 0.24 | 0.19 | 0.14 | 0.07 |
| F387 | 0.31 | 0.30 | 0.30 | 0.30 | 0.30 | 0.30 | 0.29 | 0.25 | 0.19 | 0.11 |
| F388 | 0.32 | 0.31 | 0.30 | 0.29 | 0.28 | 0.27 | 0.26 | 0.25 | 0.24 | 0.00 |
| F391 | 0.55 | 0.53 | 0.52 | 0.51 | 0.50 | 0.48 | 0.42 | 0.28 | 0.15 | 0.04 |
| F392 | 0.42 | 0.40 | 0.39 | 0.37 | 0.36 | 0.34 | 0.26 | 0.13 | 0.05 | 0.01 |
| F393 | 2.27 | 2.22 | 2.18 | 2.13 | 2.09 | 2.04 | 2.00 | 1.95 | 1.90 | 0.00 |
| F397 | 0.55 | 0.55 | 0.54 | 0.53 | 0.52 | 0.51 | 0.47 | 0.37 | 0.27 | 0.14 |

The polymorphic glucokinase (CA) repeat (GCK1) was detected by PCR with primers 5'-CCCACACCAAAACTGCCTG-TATTAG-3' and 5'-TTGGTCAGTGTAGGCTGAACTCATG-3'. Matsutani, A. et al Genomics 12, 319–325 (1992). PCR was done by initially denaturing genomic DNA for 6 min at 92° C., followed by 1 min annealing at 68° C. 30 s extension at 72° C., then using 30 cycles with 40 s denaturation at 92° C., 30 s annealing at 40 s denaturation at 92° C., 30 s annealing at 68° C., 30 s extension at 72° C., followed by a 7 min final extension at 72° C. Three alleles ranging in length from 180 to 205 bp were observed in our pedigrees, and the observed heterozygosity is 42%. Families uninformative for GCK1 were genotyped for a second microsatellite of the glucokinase locus (GCK2; Y.T., K. Chen and MA.P., unpublished results) showing four alleles in our pedigrees. GCK2 was detected by PCR, with primers 5'-CTGTGCCATGGTTATATAAGAGAAG-3' an d 5'-AAACAGATACGCT-TCATCCTGATTC-3'. PCR reaction was done under the same conditions as for the marker IP20M66. PCR products were analyzed and linkage analysis and lodscores were calculated as described in table 1.

EXAMPLE II

Other Families with Early-Onset Non-Insulin-Dependent Diabetes Mellitus

Family history and clinical data were collected in three French families having MODY. These families were ascertained by the presence of NIDDM in at least two consecutive generations and with two patients being diagnosed with NIDDM prior to 25 years of age. The criteria used for a diagnosis of NIDDM are described in Froguel et al. (1992). In kindreds F388, F390 and F391, the mean age of apparent onset (diagnosis) of diabetes was 29, 23, and 12 years in the generations born after 1930, 1950 and 1970, respectively. Most of the affected individuals have mild fasting hyperglycemia with plasma glucose values ranging from 6.2–8.5 mM, and 2 h-post glucose load concentrations ranging from 8.3–14.4 mM. One patient (2105) has mild fasting hyperglycemia but normal glucose tolerance. The fasting serum insulin levels in the MODY patients are normal, ranging from 10–17 Mμ/l. Two hour post-glucose load insulin concentrations are much higher in families F388 and F390 [range 45–80 Mμ/l] than in family 391 [range 15–51 Mμ/l]. One nondiabetic individual (2025) is insulin-resistant with fasting serum insulin values of 88 Mμ/l. All the affected individuals in families F388 and F390 are treated by diet alone. Three patients in kindred F391 (individuals 2070, 2041 and 2086) are presently being treated with sulfonylurea drugs. With the exception of individual 2044 in family F388, none of the diabetic individuals are obese (i.e., body mass-index >26 kg/m$^2$). None of the affected subjects have reported ocular, renal or vascular complications.

EXAMPLE III cDNA Encoding Glucokinase from Pancreatic β-Cells

GENERAL METHODS

Standard methods were carried out as described in Sambrook et al. (1989) and as described previously (Nishi et al. 1988). DNA sequencing was done by the dideoxynucleotide chain-termination procedure after subcloning appropriate DNA fragments into M13mp18 or M13mp19. The sequence was confirmed on both strands.

Isolation of Human Glucokinase cDNA Clones

A human liver cDNA library was screened using low-stringency hybridization conditions (Fukumoto et al. 1988) (hybridization conditions—5×SSC, 25% formamide, 2×Denhardt's solution, mmol/l sodium phosphate buffer, pH 6.5, 0.1% sodium dodecyl sulfate, 100 μg/ml of sonicated and denatured salmon testes DNA, 10% dextran sulfate, and 1×10$^6$ cpm/ml of probe at 37° C. for 16–20 h; washing conditions—2×SSC and 0.1% sodium dodecyl sulfate, for 1 h each at room temperature and then at 40° C.) with a $^{32}$P-labelled 3,248 base pair (bp) EcoRl fragment of the human hexokinase I cDNA clone, λhHEX-15 (Nishi et al. 1988), which codes for amino acids 92–917 and the 3'-untranslated region of the mRNA. The cDNA clone λhGK12-1 was obtained using this procedure. The remainder of the cDNA was obtained by reverse transcription-polymerase chain reaction (PCR) amplification of human insulinoma mRNA using specific primers rGK-13 (sense primer) 5'-GTCGAGCAGATCCTGGCAGAG-3' (SEQ ID NO: 37) and ohGK-2r (antisense primer) 5'-TGGTCCAGT-TGAGAAGGAAG-3' (SEQ ID NO: 38); the sequence of rGK-13 was based on the sequence of rat glucokinase mRNA] which gave cDNA clone—hGK3.1, and by the rapid amplification of cDNA ends (RACE) procedure (Frohman et al. 1988) using human insulinoma mRNA and the specific primer (antisense) 5'-CTCTGCCAGGATCTGCTC-TAC-3' (SEQ ID NO: 39) which generated a cDNA clone, hGK-p5, containing the 5'-end of human Beta-cell glucokinase mRNA. At least two PCR and RACE products obtained from each amplification were sequenced to control for errors that might be introduced in the amplification by Taq DNA polymerase. A cDNA encoding the human Beta-cell isoform of glucokinase, designated pGEM-hGK20 (vector -pGEM4z) was generated using the three clones described above.

Sequence of Human Beta-Cell Glucokinase cDNA and Protein

Human glucokinase cDNA clones were isolated from a liver cDNA library by low-stringency cross-hybridization with a human hexokinase I cDNA probe. The sequence of the insert in one of these clones, now termed λhGK12-1, did not correspond to hexokinase I. With the publication of the rat glucokinase cDNA sequence by Andreone et al. (1989), it became evident that λhGK12-1 encoded part of human glucokinase. Since subsequent reports indicated that the region of glucokinase mRNA present in this clone was common to transcripts expressed by beth liver and Beta cells/insulinomas, it was used as a focus to obtain the sequence for the human Beta-cell isoform. The remainder of the human sequence was obtained with a combination of reverse transcription-PCR and RACE-based approaches using human insulinoma RNA. The composite sequence of the human glucokinase cDNA clones is shown in SEQ ID NO: 36.

The sequence was obtained from the following clones: hGK-p5, nucleotides 1–393; hGK3.1, nucleotides 372–831; and hGK12-1, nucleotides 771–2603. The corresponding amino acid residue of rat Beta-cell glucokinase (Magnuson 1989; Andreone et al. 1989) is indicated above that of the human sequence at those sites at which the sequences differ. There are three differences between the cDNA sequence presented here and the sequence of human liver glucokinase (Matsutani 1992) in the region in which these two sequences overlap: Codon 107 is ATG (Met) here, in the human glucokinase gene and in the rat glucokinase cDNA sequence, and ACG (Thr) in Matsutani et al. (1989); and there are two differences in the 3'-untranslated region which are G and C in the present invention's sequence and GG and CC, respectively, in Matsutani et al. (1992). We show the sequence of codon 74 as being TTC (Phe) which is also the sequence in Matsutani et al. (1992) and in the gene disclosed herein. However, in two independent PCR products that were obtained from this region it was TCC (Ser). We assume that is difference is a conscience of misincorporation by either reverse transcriptase or Taq DNA polymerase. It is unknown if the sequence differences noted above represent polymorphisms in the human glucokinase gene.

This sequence indicates that human Beta-cell glucokinase is 465 amino acids ($M_r$=52,166). There is 97% amino acid identity between human and rat Beta-cell glucokinase. There are fifteen differences between human and rat Beta-cell glucokinase. They are scattered throughout the protein and one is in the region encoded by the Beta-cell specific exon 1. Six of the differences (amino acids 159, 181, 276, 292, 308, and 342) represent conservative amino acid replacements.

EXAMPLE IV

Isolation and Partial Sequence of the Human Glucokinase Gene from Genomic DNA of Pancreatic β-Cells Four clones, λhGK-1, 2, 5 and 7, were isolated by screening a human genomic library with the cDNA clone (SEQ ID NO: 36 as shown above) encoding human β-cell glucokinase (FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R). The partial sequence of these clones indicates that human GCK has 12 exons. Exons 1a and 2–10 encode the β-cell glucokinase mRNA. Two different glucokinase transcripts have been identified in human liver RNA; the major transcript is encoded by exons 1b and 2–10, and the minor transcript by exons 1b, 1c and 2–10. With the exception of exon 1c which is not present in the rat glucokinase gene, the organization of the human and rat glucokinase genes is otherwise identical including the positions of each of the introns, all of which interrupt the gene in protein coding regions. Because of differences in the size of the region encoded by exon 1a, 1b and 1c, the β-cell, and liver (liver$^{1b}$ and liver$^{1c}$) transcripts encode proteins of 465, 466 and 464 amino acids, respectively. In this report, amino acids are designated relative to the sequence of β-cell glucokinase.

The insert from the full-length β-cell glucokinase clone pGEM-hGK20 (Nishi et al., 1992) was labeled by nick translation and used to screen a male Caucasian placenta genomic library (Catalogue no. 946203, Stratagene, LaJolla, Calif.). The hybridization was performed in 5×SSC, 50% formamide, 2×Denhardt's solution, 20 mM sodium phosphate buffer, pH 6.5, 0.1% sodium dodecyl sulphate, 100 μg/ml of sonicated and denatured salmon testes DNA, 10% dextran sulphate, and $1\times10^6$ cpm/ml of probe at 42° C. for 10 h. The final post-hybridization wash was in 0.1×SSC and 0.1% sodium dodecyl sulfate at 56° C. for 1 h. Five clones (λHGK 1-, 2 -, 4 -, 5- and 7) were isolated. The exons were isolated using standard procedures (Sambrook et al., 1989) and sequenced using the dideoxynucleotide chain-termination procedure (Sanger et al., 1980).

EXAMPLE V

Analysis for Condon 279

Figure 3B:
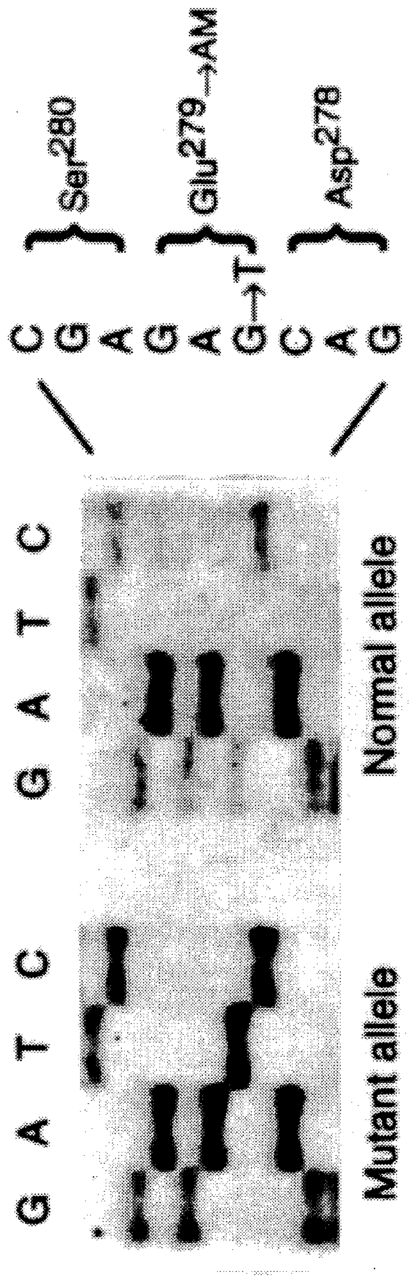
FIGS. 3A and 3B.
Figure 3A:
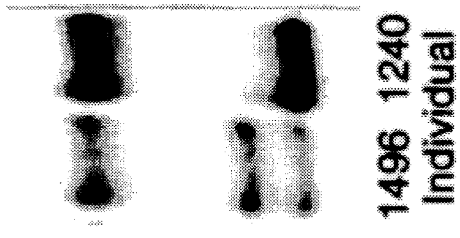

The regions of the exons were amplified in vitro using the polymerase chain reaction (PCR)(Saiki et al. 1988) and were scanned for mutations using, the technique of single-strand conformational polymorphism (SSCP)(Orita et al. 1989a; Orita et al. 1989b). Two unrelated non-diabetic individuals and an affected member from each of five families (F8, F28, F51, F85 and F393) showing tight linkage between microsatellite DNA polymorphisms in GCK and MODY (Froguel et al. 1992) were studied. SSCP-analysis of exon 7 in family F8 revealed a pattern in a patient with MODY consistent with the presence of a nucleotide substitution in one allele (FIG. 3A and FIG. 3B). This pattern was not seen in affected individuals from the other four families. (FIG. 3A and 3B represents SSCP analysis of exon 7 of GCK from a member of kindred F8 with MODY (1496) and a normal relative (1240).

One hundred nanograms of subject DNA was mixed with 10 pmol of the human GCK exon 7 specific primers, hGK7a (upstream, 5'-AGTGCAGCTCTCGCTGACAG-3') (SEQ ID NO: 40) and hGK7b (downstream, 5'-CATCTGCGCTGCACAGAG-3') (SEQ ID NO: 41) using GeneAmp (Perkin Elmer Cetus, Norwalk, Conn.). reagents and GeneAmp PCR System 9600, the $MgC_{12}$ concentration was 1.5 mM. For SSCP, the reaction volume was 10 ul and included 0.5 uCi of α-$^{32}$P-labelled dCTP (Amersham, Clinton Heights, Ill.). The PCR conditions were initial denaturation for 5 min at 94 degrees C., then 30 cycles of denaturation at 94 degrees for 1 minute and annealing and extension at 65 degrees C. for 2 min, with a final extension at 65 degrees C. for 7 min. The amplified PCR product was 286 bp and contained exon 7

(184 bp) and 41 and 61 bp of the flanking introns, including primers.

Samples were processed for SSCP analysis according to the methods of Orita et al. The fragments were separated on a 40 cm 5% acrylamide (24:1 acrylamide:bis) gel run in 1×Tris-borate buffer at room temperature without glycerol. The gel was run at 6 watts for 12 h at which time the xylene cyanol dye was at the bottom of the gel. The gel was exposed to X-ray film overnight. For amplifying exon 7 for sequencing, the reaction volume was 100 ul and the PCR conditions were as described above except 35 cycles were used. After PCR, unincorporated nucleotides and primers were removed using a Centricon-100 microconcentrator (Amicon, Danvers, Mass). The 286 bp PCR product was cloned into the Hinc II site of the M13mp18 DNA and sequenced using a Sequenase DNA Sequencing Kit (USB, Cleveland, Ohio). PCR products of exon 7 were sequenced directly using a DNA Cycle Sequencing System (GIBCO-BRL, Gaithersburg, Md.) and primers HGK7A and ohGK 22 (5'-CATGTGCGTCATACGAGT-3') (SEQ ID NO: 42) or using these primers with an Applied Biosystem DNA Seducer (Model 373A): dideoxy-cycle-sequencing reactions (25 cycles) were carried out in tubes containing 80–120 ng of the PCR product using fluorescence-labelled dideoxy terminators as described by Applied Biosystems.

Amplification and direct sequencing of exon 7 in individual 1496 of family F8 revealed a single nucleotide change in this exon. There was a G to T substitution in codon 279 [using the amino acid numbering of the β-cell isoform of human glucokinase (this protein is 465 amino acids)] which changes GAG (Glu) to TAG, an amber termination codon. The presence of this mutation was confirmed by subcloning the PCR product into M13mp18 and determining, its sequence. SSCP analysis of other members of kindred F8 (FIG. 4) showed that this mutation was only present in individuals with MODY. The nonsense mutation was also confirmed by direct sequencing of the PCR product in seven other affected members. In addition, the sequence of exon 7 was shown to be normal in three non-diabetic members. As noted previously (Saiki et al. 1988), there is a patient in this family (individual no. 50 in FIG. 4) who has NIDDM but does not show linkage with the DNA polymorphisms in GCK that are associated with MODY in other members of this pedigree. Moreover, she does not have the nonsense mutation in codon 279. We consider that this patient has another form of NIDDM since she is obese and had a later age-at-onset (52 years) of NIDDM than other members of the family with MODY. In addition, none of her children or grandchildren, all older than 20 years, have diabetes. Thus, there are several forms of NIDDM present in kindred F8. Such heterogeneity has been noted in other families with MODY (Bell et al. 1991). The linkage between the nonsense mutation and MODY in family F8 is highly significant. Assuming a frequency of the mutation of 0.1% in the general population and considering individual 50 as unknown, with respect to MODY, a test of no linkage versus linkage with the assumption of complete linkage disequilibrium between the mutation and the disease allele gave a test statistic of 10.0 on the lod score scale. SSCP analysis of 34 unrelated non-diabetic subjects and 55 unrelated members of the CEPH families did not show the mutant pattern implying that the nonsense mutation in GCK is not a common polymorphism.

Figure 4:
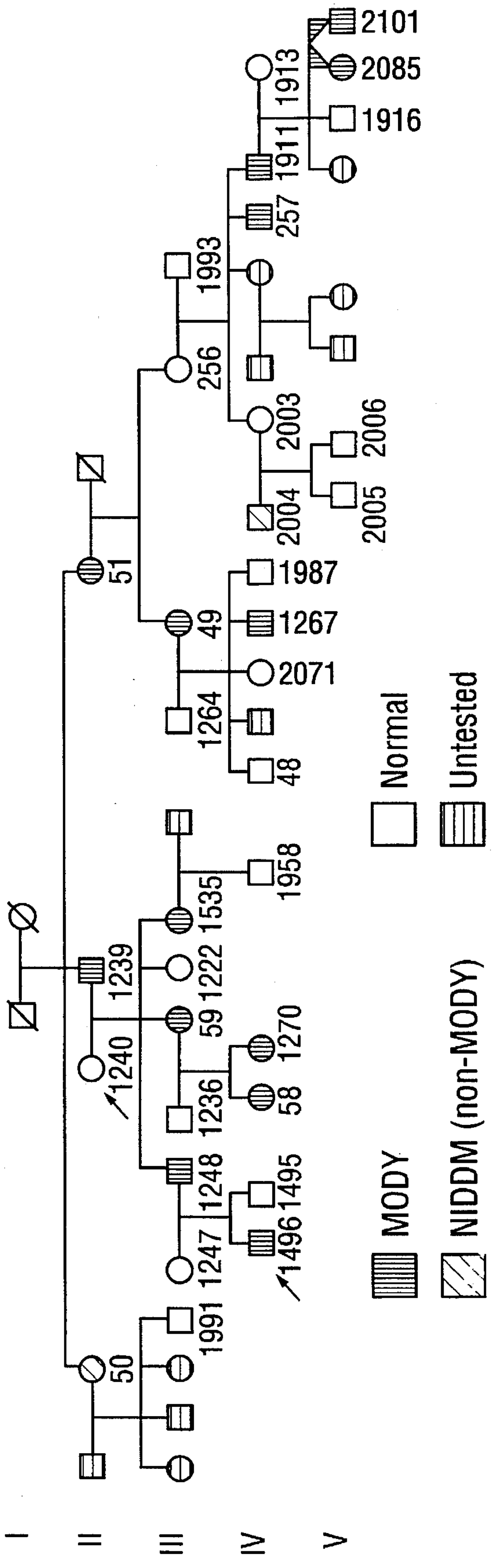
FIG. 4. Partial pedigree of kindred F8.
Figure 5:
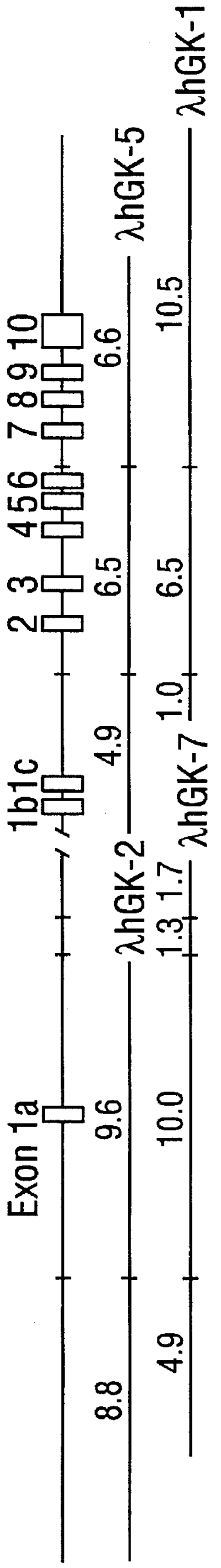
FIG. 5. Organization of the human glucokinase gene. Positions of the exons are indicated by cross-hatched boxes. The restriction map was derived from four partly overlapping clones (bottom), and EcoRI sites and corresponding fragment sizes are indicated. The microsatellite DNA polymorphisms that have been identified in GCK are located upstream of exon 1a (Nishi et al. 1992; Froguel et al. 1992) and downstream of exon 10 (Matsutani et al. 1992, Froguel et al. 1992).

FIG. 4 illustrates the partial pedigree of kindred F8. Thirty-four individuals were studied and seventeen of these have diabetes mellitus. With the exception of individual no. 50, none of the diabetic individuals are Obese (ie. BMI>26). The mean age of apparent onset of diabetes was 6 and 16 years of age in generations 5 and 4, respectively. Most of the affected individuals in this family have mild fasting hyperglycemia with blood glucose values ranging from 6.7–9.0 mM. Two individuals are presently being treated with sulfonylurea drugs (individuals 59 and 1239; the patient with NIDDM, individual no. 50 is also being treated with sulfonylurea drugs) and one with insulin (individual 1267). The fasting and 2-hour postglucose-load insulin levels are not different between affected and non-affected individuals. The form of mild diabetes seen in this family seems to be quite frequent among MODY patients in France (Lestradet et al. 1989). The CEPH identification numbers of the subjects studied are shown. Individuals considered to have MODY using the diagnostic criteria described in Froguel et al. (1992) are indicated by black symbols. All of these individuals were tested for the nonsense mutation at codon 279 in exon 7 by SSCP or direct-sequencing strategies and except for individual no. 50 (this patient is believed to have a form of NIDDM other than MODY, see discussion in text), all were heterozygous for this mutation. The affection status of the members of this family are noted. The arrows indicate the two individuals from this family who were screened using SSCP (FIG. 4).

EXAMPLE VI

Metabolic Effects of the Amber Mutation at Condon 279

MODY has an autosomal dominant mode of inheritance. The molecular mechanism by which mutations in glucokinase may lead to the development of glucose intolerance and diabetes mellitus is unknown. Since glucokinase appears to be a monomer and there is no evidence for dimerization (Holroyde et al. 1976), it seems unlikely that the nonsense peptide binds to the functional protein that is the product of the normal allele and acts as a dominant negative regulator of glucokinase activity. A more likely hypothesis may be that the levels of glucokinase activity in the β-cell are critical in determining the threshold at which the β-cell secretes insulin in response to changes in glucose concentration. In this regard, Meglasson and Matschinsky (1984) have suggested that a modest 15% decrease in glucokinase activity might shift the set point for glucose-induced insulin secretion from 5 to 6 mM.

EXAMPLE VII

Identification of Missense Mutations in Families with Early-Onset NIDDM

Figure 7:
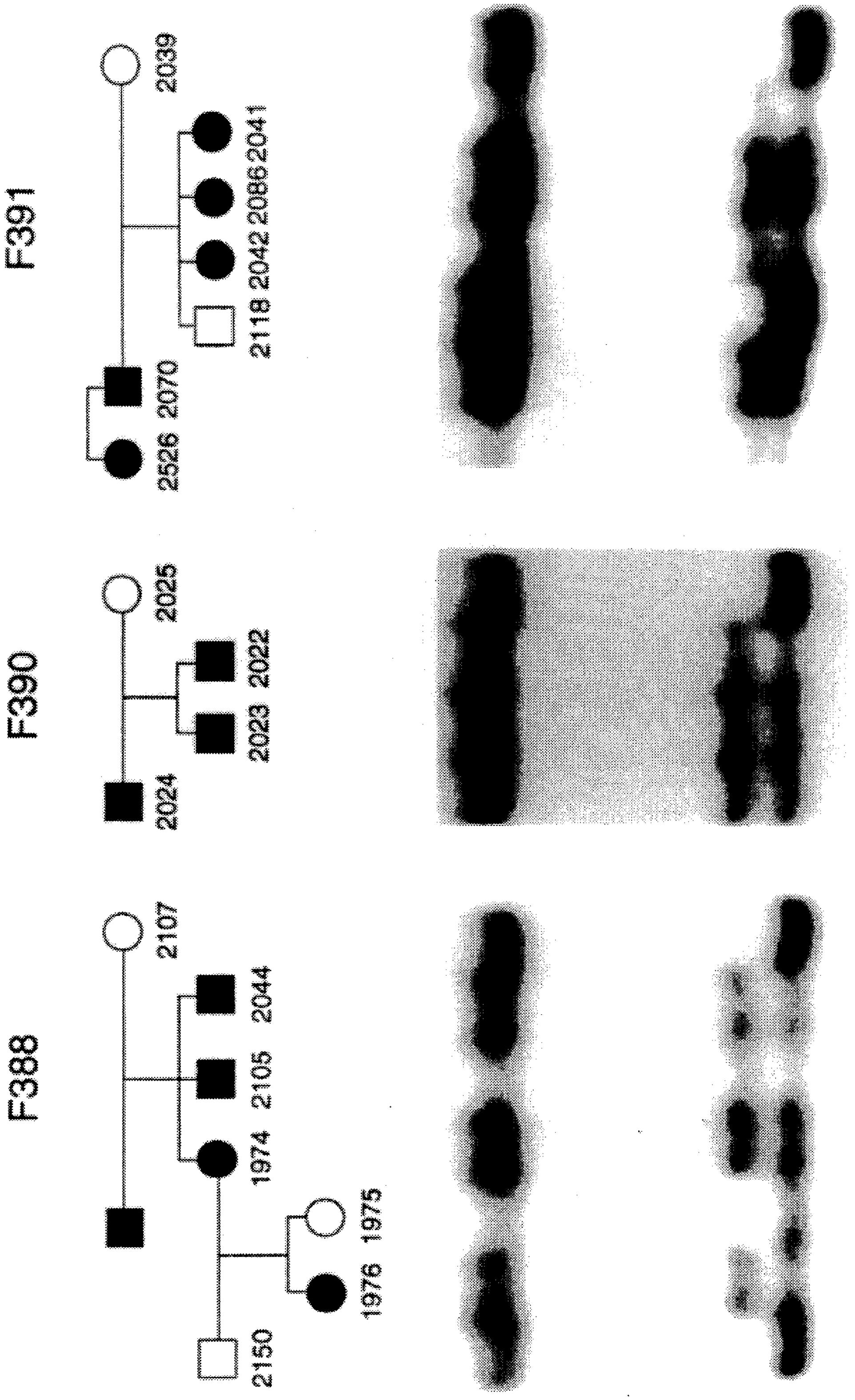
FIG. 7. SSCP analysis of kindreds F388, F390 and F391. Open symbols represent nondiabetic individuals, while filled symbols represent subjects with early-onset NIDDM. The numbers under the symbols indicate the sample identification number. The DNA fragment containing exon 7 was obtained by PCR amplification using oligonucleotide primer pair 7 (Table 3). PCR and SSCP were carried out as described in Vionnet et al. 1992; Stoffel et al. 1992. The SSCP pattern shown here was obtained from a non-glycerol containing, 5% non-denaturing polyacrylamide gel run at room temperature. The unique conformer cosegregates without exception with the diabetic phenotype.

SSCP analysis was used to scan the glucokinase gene for mutations in families with early-onset NIDDM showing evidence of linkage with microsatellite DNA polymorphisms in GCK. All 12 exons of the glucokinase gene of two affected and one unaffected family member were amplified in vitro using the PCR primer pairs described in Table 3 and analyzed by SSCP. Abnormally migrating bands in exon 7 present were observed in affected individuals of kindreds F388, F390 and F391. FIG. 7 shows the SSCP patterns and their cosegregation with NIDDM in these families. The heterozygous pattern seen is consistent with the presence of a mutation in only one allele. The variant bands (evident on both glycerol-free and glycerol-containing gels run at 4° C.) were not present in 89 unrelated French, non-diabetic, Caucasian control subjects or 115 NIDDM patients. In addition to the conformers seen in exon 7, a common conformer was seen on SSCP analysis of exon 9. As discussed below, this is a common polymorphism in intron 9 that is present in both affected and normal individuals. It does not cosegregate with NIDDM in the kindreds described above.

SSCP ANALYSIS

For SSCP analysis, 100 ng of DNA mixed with 10 pmol of human GCK specific primer pairs. The PCR reaction was using GeneAmp reagents (Perkin Elmer Cetus, Norwalk, Conn.) and 1.5 mM $MgCl_2$. The reaction volume was 10 μl and included 0.2 μl of α-[$^{32}$P]DCTP (3000 Ci/mmol, Amersham, Arlington Heights, Ill.) and 1U of Taq DNA polymerase. The PCR conditions were initial denaturing at 94° C. for 5 min, followed by 35 cycles of denaturation at 94° C. for 1 min, annealing at 60° C. for 1 min, and extension at 72° C. for 2 min, with a final extension of 10 min. Exons 5 and 6 were co-amplified using the 5'- exon 5 and 3'-exon 6 primers to yield a 379 bp fragment that was digested with Pst I prior to SSCP analysis. The resulting 214 and 166 bp fragments contained exon 5 and 6 respectively. Similarly exon 9 was digested with Sph I to yield a 205 and 162 bp fragment representing the 5'- and 3'-halves of exon 9, respectively. The amplified PCR products were diluted 10-fold in formamide buffer, denatured at 95° C. for 5 min, quick-cooled and run on a glycerol-free and 10% glycerol containing 40 cm 5% non-denaturing acrylamide (24:1 acrylamide:bis) gel at room temperature and/or 4° C. The gels were run at between 6 and 20 watts for 5–10 h. The gel was dried and autoradiographed at −80° C. overnight with intensifying screens. The polymorphism in intron 9 was noted only on glycerol-free gels run at either 4° C. or room temperature.

TABLE 3

Sequences of primer pairs for PCR-SSCP analysis of human GCK

| Exon | Upstream primer | Downstream primer | Size of PCR product (bp) |
|---|---|---|---|
| 1a | 5'-TCCACTTCAGAAGCCTACTG (SEQ ID NO: 12) | 5'-TCAGATTCTGAGGCTCAAAC (SEQ ID NO: 13) | 195 |
| 1b | 5'-AGCAGGCAGGAGCATCTCTG (SEQ ID NO: 14) | 5'-GCTGCTCTCCCAGTGCAAAG (SEQ ID NO: 15) | 149 |
| 1c | 5'-CCAGACTCTCCTCTGAACTC (SEQ ID NO: 16) | 5'-GAAGAAGAGGTTCCATCTGA (SEQ ID NO: 17) | 145 |
| 2 | 5'-TGCAGATGCCTGGTGACAGC (SEQ ID NO: 18) | 5'-CACAGCTGCTTCTGGATGAG (SEQ ID NO: 19) | 290 |
| 3 | 5'-TAATATCCGGCTCAGTCACC (SEQ ID NO: 20) | 5'-CTGAGATCCTGCATGCCTTG (SEQ ID NO: 21) | 295 |
| 4 | 5'-TAGCTTGGCTTGAGGCCGTG (SEQ ID NO: 22) | 5'-TGAAGGCAGAGTTCCTCTGG (SEQ ID NO: 23) | 272 |
| 5 | 5'-GCAGCCACGAGGCCTATCTC (SEQ ID NO: 24) | 5'-GAGAAAGGCAGGCAGTGCTG (SEQ ID NO: 25) | 195 |
| 6 | 5'-CCAGCACTGCAGCTTCTGTG (SEQ ID NO: 26) | 5'-GAGCCTCGGCAGTCTGGAAG (SEQ ID NO: 27) | 176 |
| 7 | 5'-AGTGCAGCTCTCGCTGACAG (SEQ ID NO: 28) | 5'-CATCTGCCGCTGCACCAGAG (SEQ ID NO: 29) | 285 |
| 8 | 5'-TGCCTGCTGATGTAATGGTC (SEQ ID NO: 30) | 5'-TGAGACCAAGTCTGCAGTGC (SEQ ID NO: 31) | 263 |
| 9 | 5'-ACTGTCGGAGCGACACTCAG (SEQ ID NO: 32) | 5'-CTTGGAGCTTGGGAACCGCA (SEQ ID NO: 33) | 367 |
| 10 | 5'-GTCGACTGCGTGCAGGGCGC (SEQ ID NO: 34) | 5'-TGTGGCATCCTCCCTGCGCT (SEQ ID NO: 35) | 263 |

EXAMPLE VIII

Identification of Missense Mutations in Exon 7

Sequencing of exon 7 revealed mutations in codon 228 [ACG$^{Thr}$→ATG$^{Met}$] in kindred F391 and the same mutation in codon 261 (GGG$^{Gly}$→AGG$^{Arg}$) in both kindred F388 and F390 (FIG. 4). These mutations were found in all the affected subjects and did not occur in any of the normal members of these kindreds. Both mutations occur within the context of a CpG dinucleotide and involve a CpG to TpG transitions [or CpG to CpA transition if the deamination event occurs on the complementary strand] suggesting that these sites may represent potential hotspots for mutation. The identification of the same nucleotide substitution in codon 261 in two unrelated families is consistent with this notion. The threonine at position 228 is invariant in the sequences of the catalytic domains of all mammalian and yeast hexokinases glucokinases. The glycine at 261 is invariant in all mammalian hexokinases and glucokinases.

EXAMPLE IX

Figure 8A:
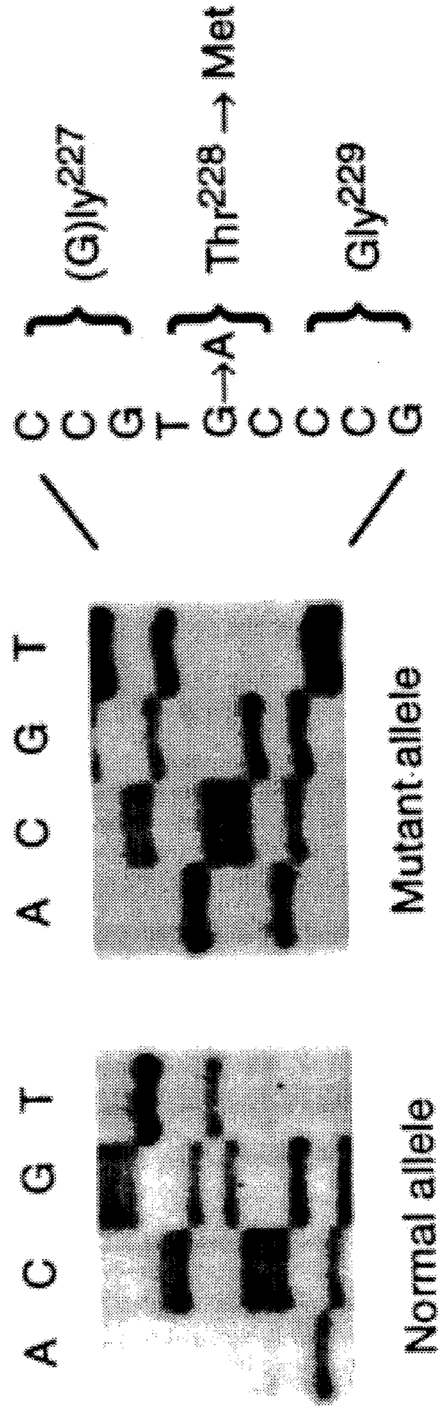
FIGS. 8A and 8B. Sequences of mutations in exon 7.
Figure 8B:
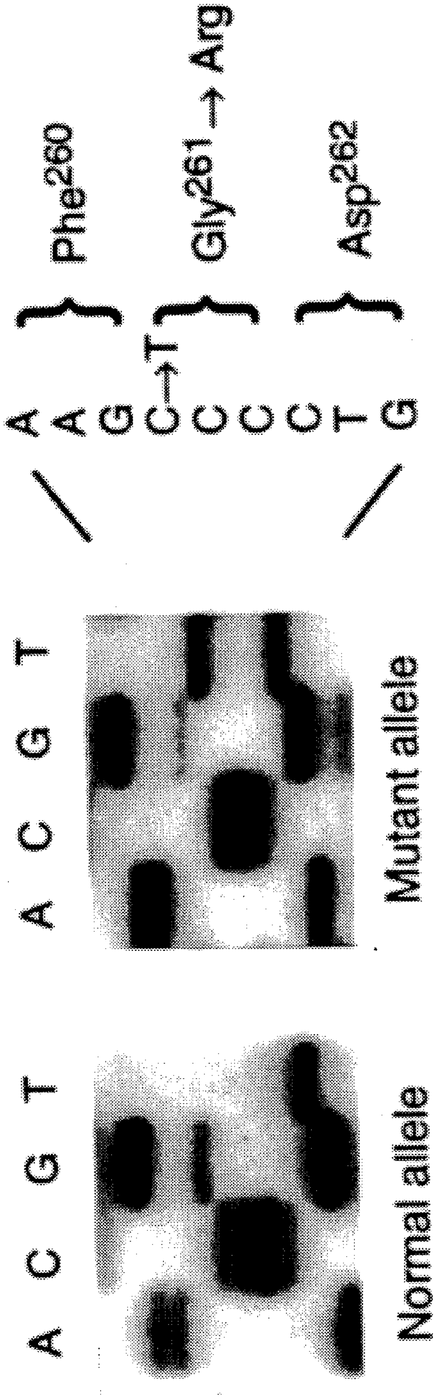

Characterization of a Common Polymorphism in Intron 9 which does not Correlate to MODY Not all DNA polymorphism identified in the GCK genomic DNA correlated to MODY. Scanning exon 9 and adjacent intron sequences by SSCP revealed a common polymorphism occurring in both affected and unaffected individuals of kindreds F380, 390 and 391. The sequence of this region revealed a C→T substitution in intron 9, eight nucleotides downstream of the splice donor site (FIG. 8A and FIG. 8B). This polymorphism also occurs in the context of a CpG dinucleotide. The frequency of the C and T alleles in a group of 30 unrelated non-diabetic individuals was 0.80 and 0.20, respectively.

SEQUENCING OF PCR PRODUCTS

The amplified PCR products were sequenced directly using an Applied Biosystems (Foster City, Calif.) DNA Sequencer, Model 373A, and a dideoxy-cycle-sequencing protocol and the primers described in Table 3 together with fluorescent-labeled dideoxy terminators as described by Applied Biosystems. PCR products were also cloned into the Hinc II site of M13mp18 DNA and sequenced using a Sequenase DNA Sequencing Kit (USB, Cleveland, Ohio).

EXAMPLE X

Mutations in Glucokinase may Alter Glucose and ATP Binding

Figure 9A:
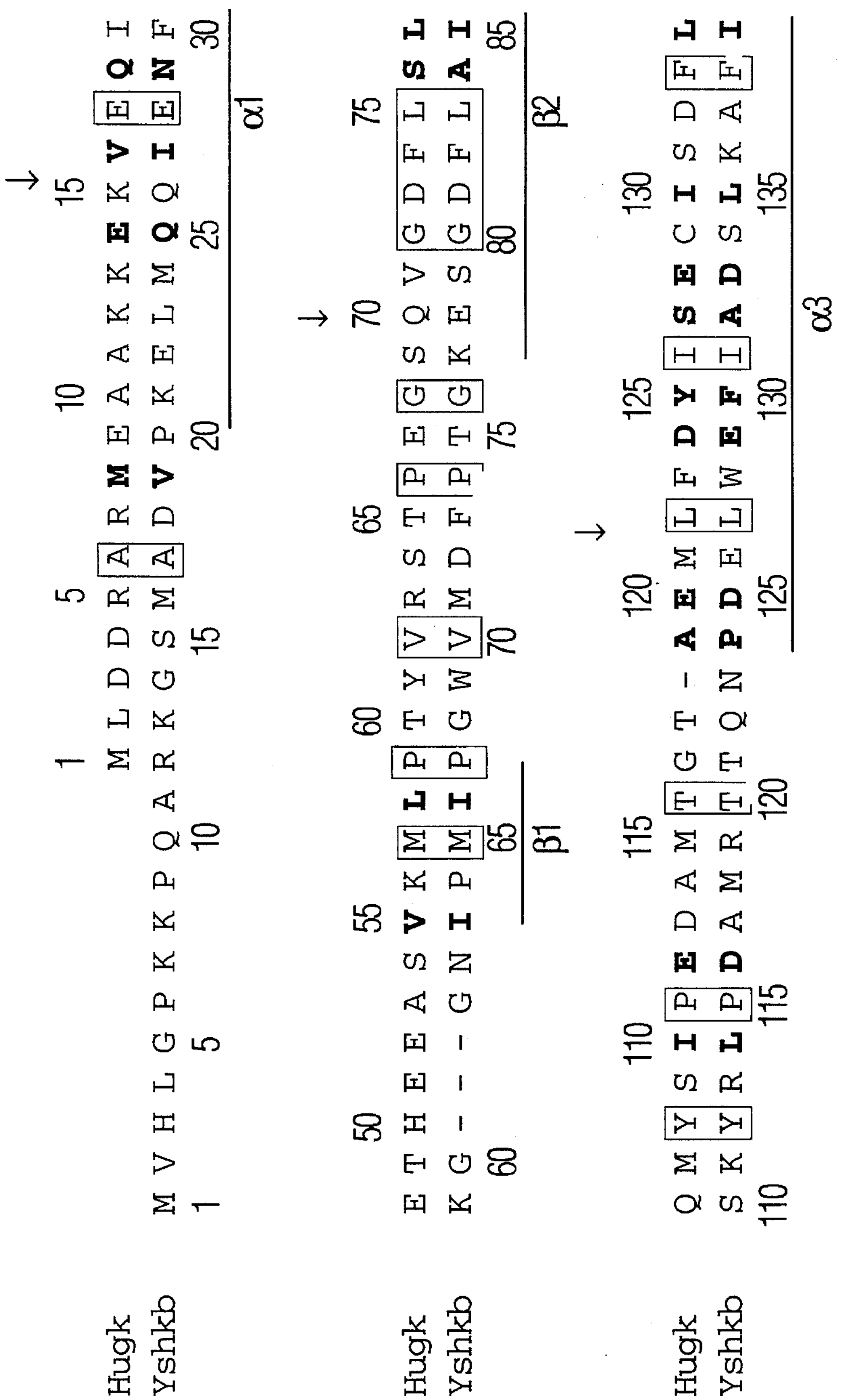
Figure 9B:
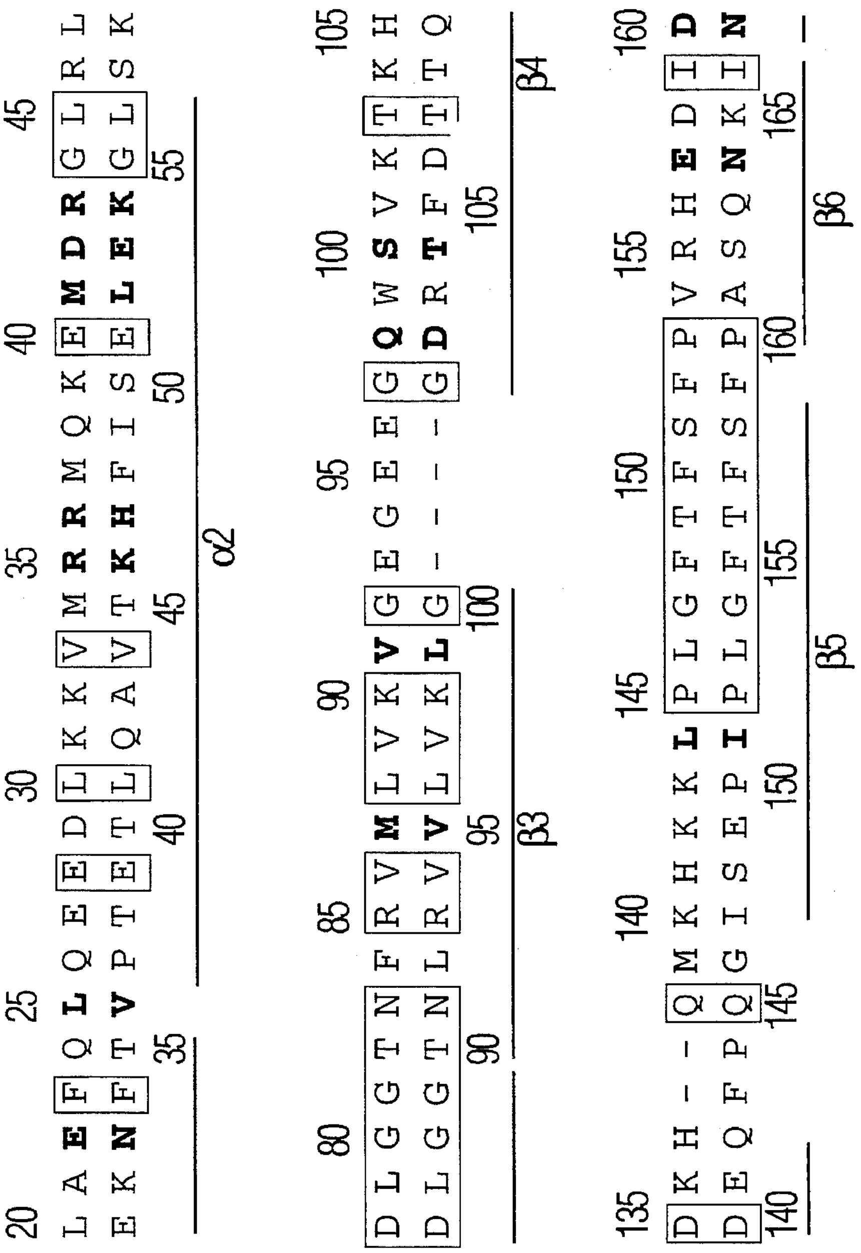
Figure 9C:
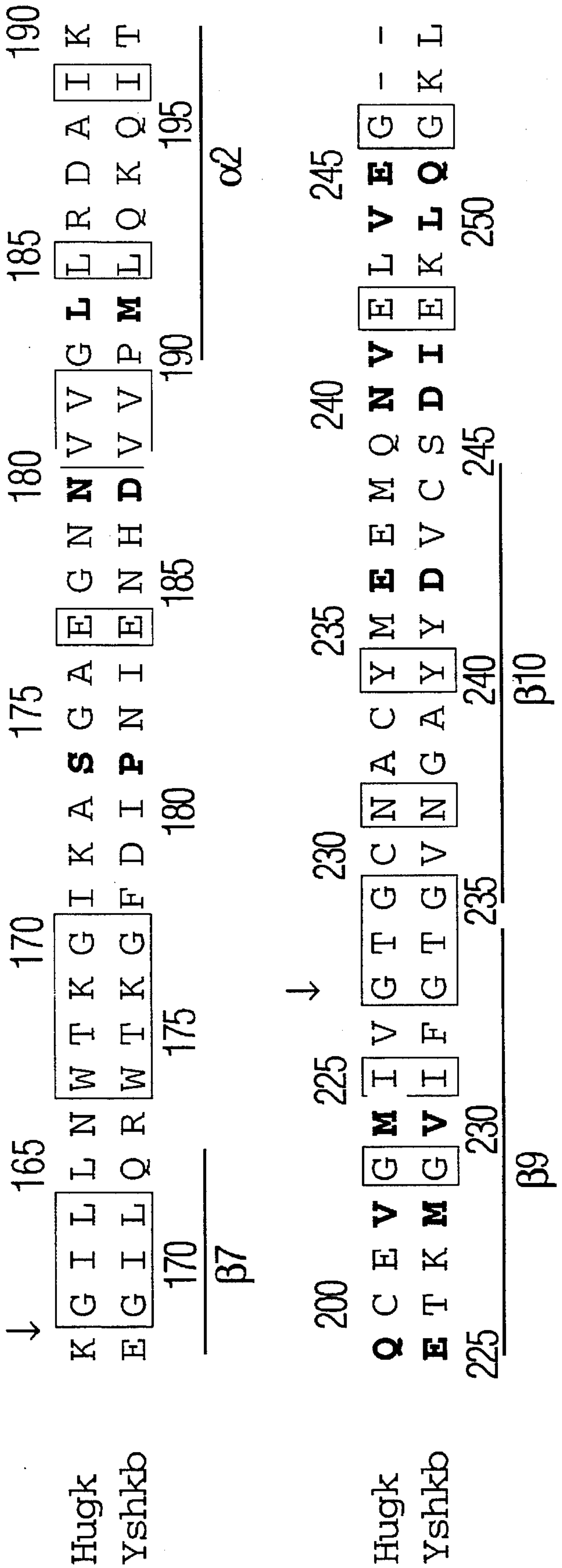
Figure 9D:
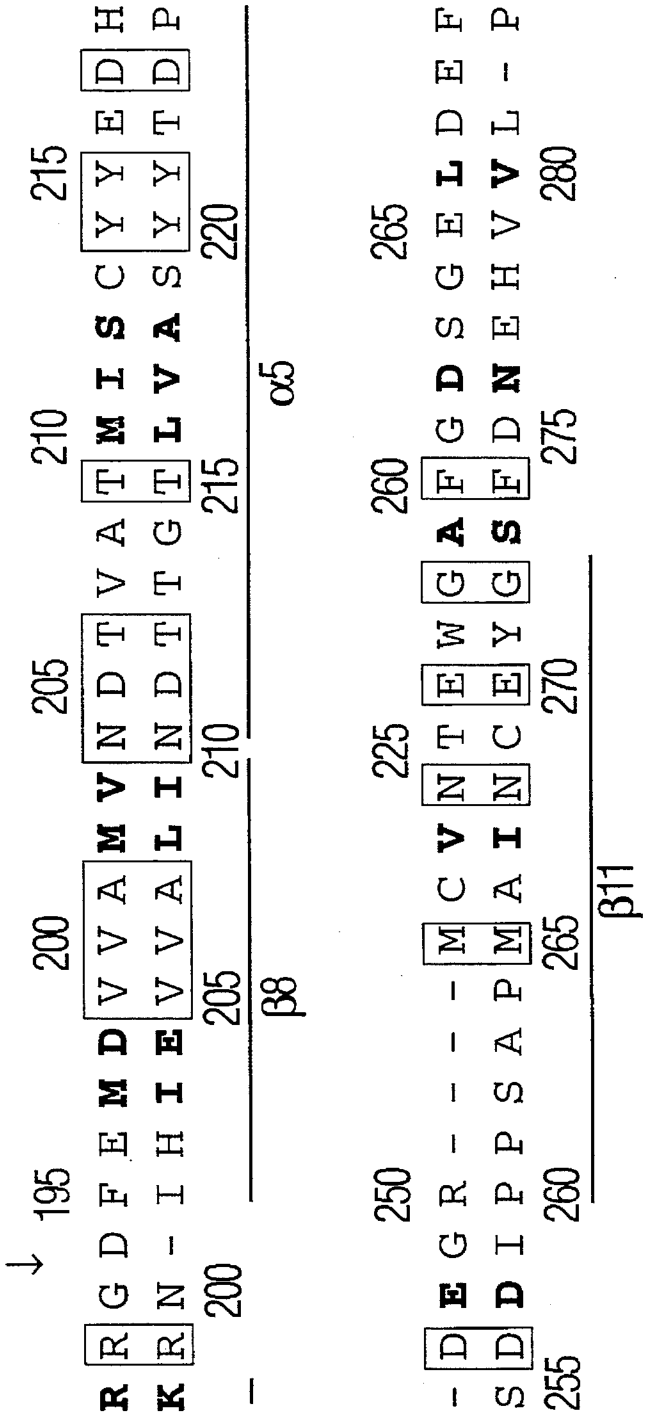
Figure 9E:
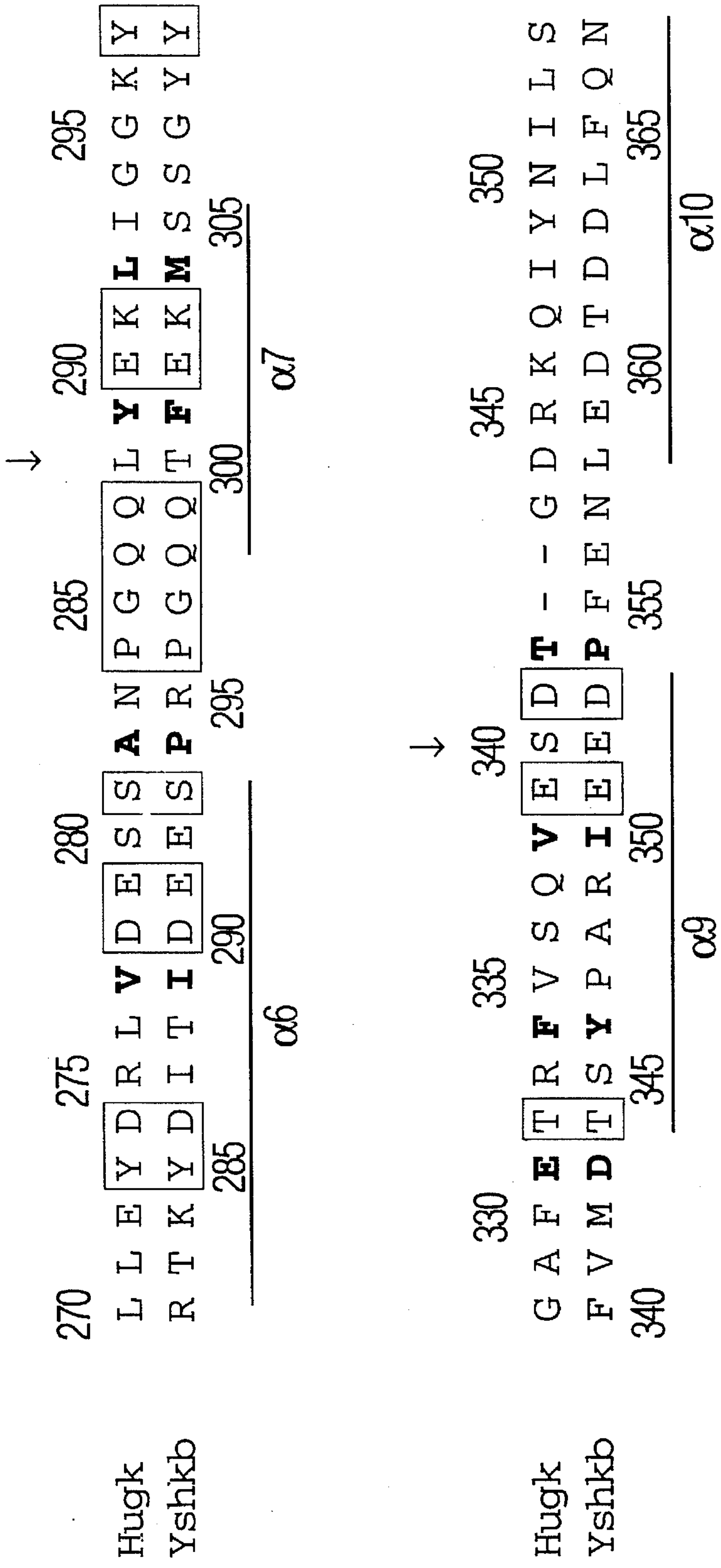
Figure 9F:
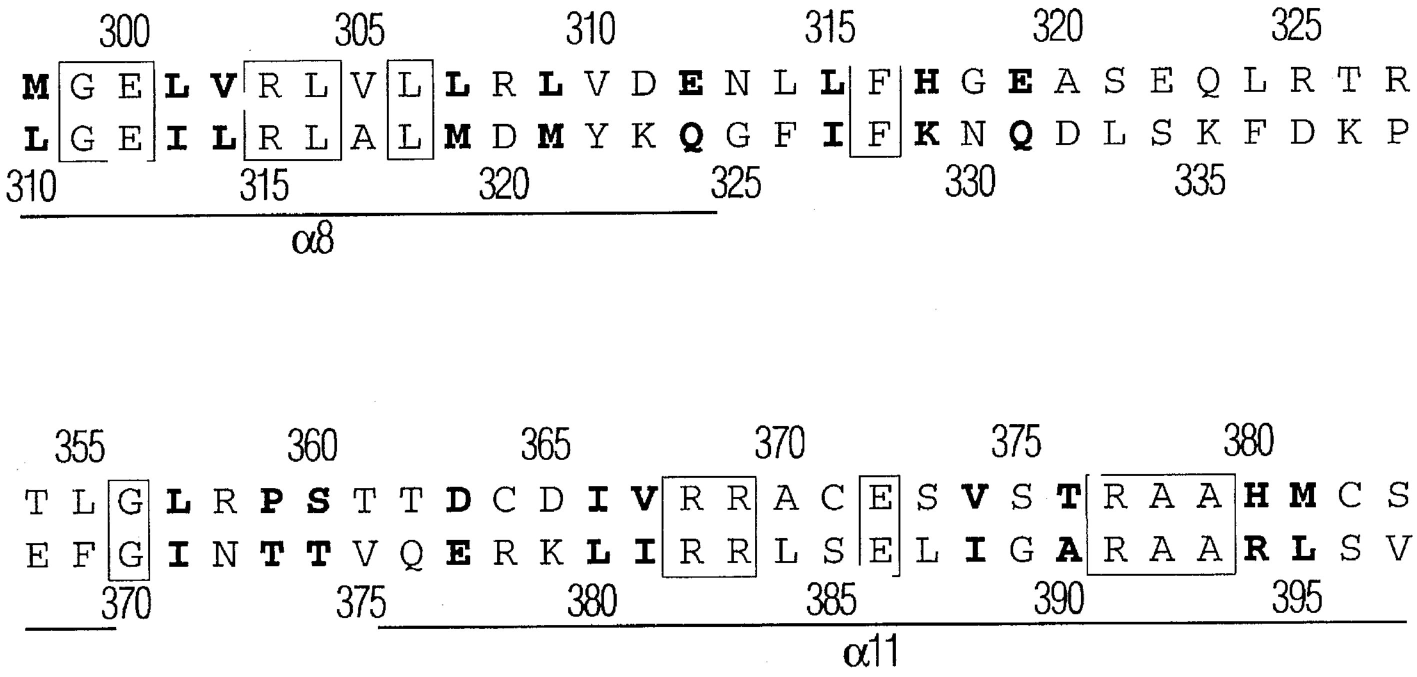
Figure 9H:
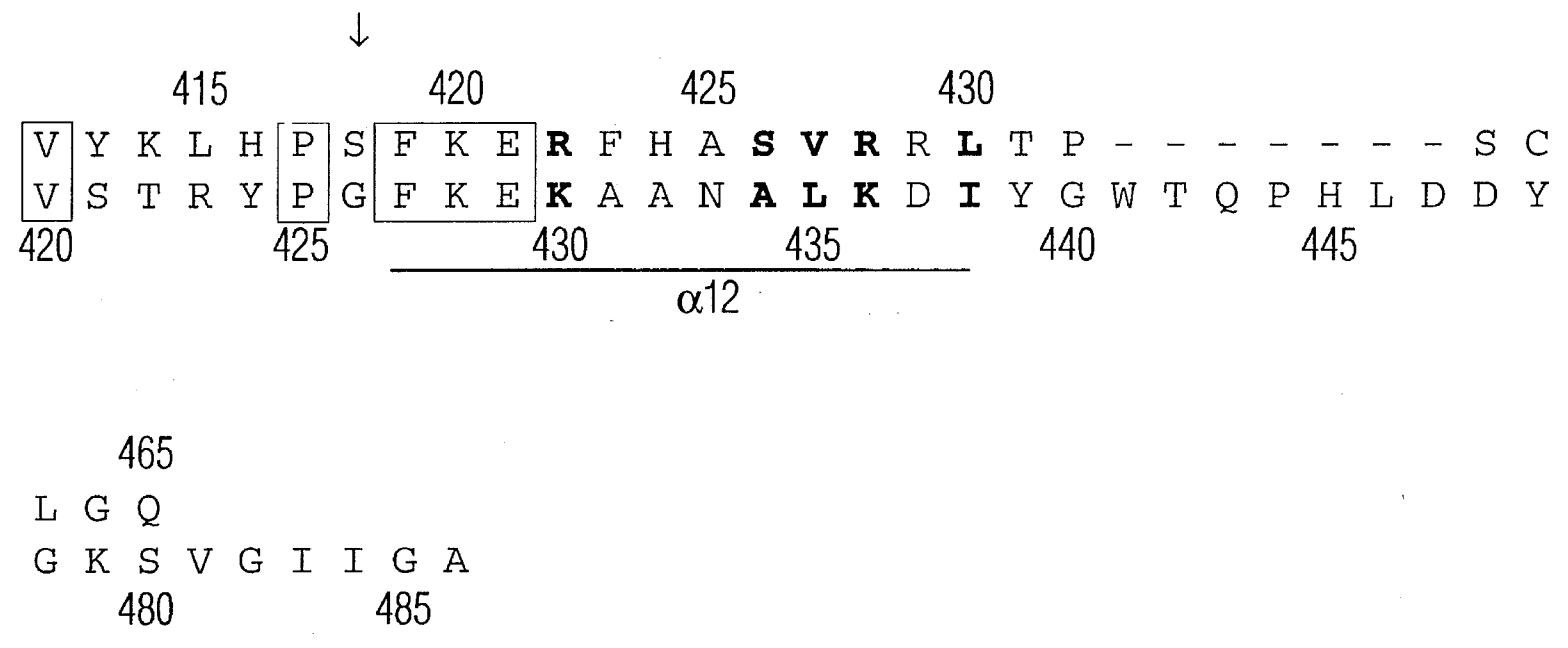

The structural alignment of the amino acid sequences of human β-cell glucokinase (465 amino acids) and yeast hexokinase β (486 amino acids) is shown in FIG. 9A, FIG. 9B, FIG. FIG. 9D, FIG. 9E, FIG. 9F, FIG. 9G, FIG. 9H. There are 11 regions of relative insertions or deletions (excluding the $NH_2$-terminus) that have been positioned relative to turns between elements of secondary structure. The insertions/deletions range in size from one to 7 residues. In the $NH_2$-terminal region of glucokinase, there are three insertions and two short deletions, and in the COOH-terminal half of glucokinase, there are several deletions relative to hexokinase. This is a preliminary structural alignment and may differ slightly from a comparison of the actual structures of these proteins. There are 138 identical residues in human glucokinase and yeast hexokinase B, about 30% identity. We predict that human glucokinase will show the same arrangement of α-helices and β-strands as observed in the crystal structure of yeast hexokinase.

The exon/intron organization is indicated on FIG. 9*a* in relation to the secondary structure predicted for glucokinase. There are nine introns within the glucokinase gene. The exon 5–6 boundary lies in the loop between helix 4 and β8, exon 10 starts at the $NH_2$-terminal residue of helix 12, 6 exons start with 2–3 residues of the ends of helices or β-strands, and exon 2 starts in the middle of helix 1. Therefore, while many of the introns occur near the ends of secondary structural elements, it is not obvious that the exons represent separate functional modules of the enzyme.

Figure 9I:

The positions of the mutations in human glucokinase associated with early-onset NIDDM have been indicated on the ribbon backbone drawing of yeast hexokinase B in FIG. 9I. The mutation of E279 to a stop codon described previously is predicted to generate an inactive enzyme. Both domains of hexokinase are involved in packing interactions with the COOH-terminal helix 13, so that synthesis of a truncated protein by removing the COOH-terminal region is predicted to greatly interfere with correct folding of the enzyme.

The two missense mutations T228H and G261R are both located in or close to the active site cleft between the two domains of the enzyme. The residue $Thr^{228}$ is invariant in all mammalian and yeast glucokinases and hexokinases. In yeast hexokinase B, the equivalent residue is $Thr^{234}$ and the hydroxyl side chain of this amino acid forms a hydrogen bond with a sulfate ion in the crystal structure. This sulfate site yam predicted to represent one of the phosphate binding sites of ATP. Therefore, in glucokinase, the T228M mutation is proposed to eliminate a hydrogen bond interaction with the phosphate of ATP, which is excepted to reduce the binding affinity for ATP and effect enzymatic activity. The residue $Gly^{261}$ of glucokinase is equivalent to amino acid $Asp^{174}$ of hexokinase B. The residue not conserved, but forms part of a loop leading into the glucose binding site. The substitution of Arg introduces a much larger side chain and this may interfere with the correct conformation of the enzyme near the active site.

MODELING OF HUMAN GLUCOKINASE STRUCTURE

The crystal structure of yeast hexokinase isozyme B was used as a simple model for the structure of human glucokinase. The atomic coordinates for the B isozyme were refined to an R-factor of 0.203 with 2.1Å X-ray data and using the correct amino acid sequence (Harrison, 1985). This structure was examined on an ESV10 Evans and Sutherland computer graphics system using the program FRODO (Jones, 1978). The assumption is that the structural core and the active site residues are likely to be conserved in yeast hexokinase and human glucokinase. The elements of secondary structure, (α-helices and β-strands were located by visual examination and plotted on the amino acid sequence of yeast hexokinase. Then, the amino acid sequence of human glucokinase was aligned to that of yeast hexokinase, allowing deletions and insertions only between the elements of secondary structure. The positions of the mutations were then located on the aligned structure and in the hexokinase crystal structure in relation to the glucose binding site.

In yeast hexokinase, the glucose binding site was defined by the position of the inhibitor, o-toluoylglucosamine (OTG), in the crystal structure of the B isozyme. The binding of glucose to hexokinase produces a conformational change that results in a closing of the cleft between the two domains of the enzyme. The ATP binding site is less well established and was predicted by extrapolation from the difference density due to AMP to the position of a sulfate ion that was pressed to represent a phosphate binding site in hexokinase B.

EXAMPLE XI

Metabolic Explanations of NIDDM

The molecular mechanism by which mutation of glucokinase may lead to the development of an autosomal dominant inherited disease of glucose intolerance and diabetes mellitus is unknown. Glucokinase Catalyses the first step, and also the first rate-limiting reaction, of glycolysis in liver and pancreatic β-cells and is believed to play an important role in glucose disposal by the liver and to participate in glucose sensing by the pancreatic β-cell. The pattern of inheritance of early-onset NIDDM argues for the presence of both normal and mutant. glucokinase molecules in the hepatocyte and β-cell. Since glucokinase appears to act as a monomer with no evidence of oligomerization, it seems unlikely that the mutant protein binds to the normal functional enzyme and acts as a dominant negative regulator of glucokinase activity. However, if glucokinase normally associates with the specific glucose transporter isoform expressed in β-cells and liver, GLUT2, perhaps the mutant protein could still bind to GLUT2 and by doing so otherwise inhibit or alter the transport of glucose across the plasma membrane; i.e., glucokinase mutations function as dominant-negative regulators of glucose transporter activity. Since decreased expression of GLUT2 is associated with an impaired insulin secretory response to glucose, this may be a reasonable hypothesis and moreover could be tested using the artificial insulin-secreting cell lines described by Hughes et al (1992). However, genetic studies have shown that the GLUT2 is not linked to early-onset NIDDM. Heterozygous defects in glucokinase may also cause early-onset diabetes by a gene dosage effect. Meglasson and Matschinsky (1984) have suggested that a modest decrease in glucokinase activity may shift the threshold for insulin secretion response to a physiological glucose challenge from 5 to 6 mM.

The pathogenesis of NIDDM involves both insulin-responsive tissues such as liver, muscle and adipose tissue, as well as the insulin-secreting pancreatic β-cell. Mutations in the insulin receptor have been implicated as a primary lesion in a small group of patients with clinical features of insulin resistance. Insulin gene mutations have also been described but are very rare and unlikely to be an important cause of impaired β-cell function leading to diabetes. The demonstration of mutations in a glycolytic enzyme that cause NIDDM implies that diabetes mellitus may truly be a disorder of glucose metabolism. Since the mutations in glucokinase that have been identified to date are in that part of the protein that is common to both the hepatic and β-cell isoforms, they may compromise glucose metabolism by each tissue. The consequences of reduced levels of hepatic glucokinase are unclear but perhaps they may impair the liver's ability to remove glucose from the portal circulation. The identification of the genetic lesion in a readily identifiable subgroup of patients with NIDDM will allow us to correlate molecular alterations with heterogenous diabetic phenotypes, disease progression, development of complications and responses to medication. Furthermore, the identification of mutations in glucokinase cause glucose intolerance and diabetes mellitus suggests that other glycolytic enzymes, especially those that control rate-limiting steps in glucose metabolism, are candidates for contributing to the development of this genetically heterogeneous disorder.

EXAMPLE XII

GCK as a Target for Therapeutic Intervention

We are continuing to screen MODY families using SSCP and direct-sequencing strategies for other mutations in GCK. In addition, we are screening NIDDM patients having the more common late-onset form of this disorder to determine if genetic variation in GCK also contributes to its development. Finally, if mutations in GCK can contribute to the development of NIDDM, perhaps acquired changes resulting in decreased levels of glucokinase may have the same effect. Glucokinase may represent an interesting target for therapeutic intervention.

EXAMPLE XIII

Diagnostic Approaches

The studies of families with early-onset NIDDM reported here have identified a diabetes-susceptibility gene on chromosome 20 and have shown that mutations in GCK in chromosome 7 can cause this form of NIDDM. However, there are families with early-onset NIDDM who show no evidence for linkage with markers on chromosome 20 or with GCK on chromosome 7 indicating that there are additional genes whose mutation can result in the phenotype of early-onset NIDDM. Of these however, GCK may be the most important. The proportion of French families with early-onset NIDDM that is linked to GCK was estimated to be 0.8 (0.45–0.95 one-lod-unit support interval). It is suggested therefore that diagnostic approaches based on the primers and techniques identified herein may provide useful methods for diagnosing previously unidentified individuals with propensity to develop MODY.

REFERENCES CITED

The following references to the extent that they provide procedural details supplementary to those set forth herein, are specifically incorporated herein by reference.

Andreone T. L. et al. *J Biol Chem* 264:363 (1989)
Barker, D. et al. *Cell* 36, 131-138 (1984).
Barnett, A. H. et al. *Diabetologia* 20, 87–93 (1981).
Bell, G. I. et al. *Proc. Natl. Acad. Sci. U.S.A.* 78, 5759–5763 (1981).
Bell, G. I. et al. *Proc. Natl. Acad. Sci. U.S.A.* 88, 1484–1488 (1991).
Cammidge, P. J. *Br. Med. J.* 2, 738–741 (1928).
Chanson, Ph. et al. *J. Med. Sci.* 7, 336–345 (1991)
Chehab et al. *Nature* 329:293 (1987)
Conner et al. *Proc. Natl. Acad. Sci. U.S.A.* 80:78 (1983)
Defronzo, R. A. *Diabetes* 37, 667–687 (1988)
Fajans, S. S. *Diab./Metab. Rev.* 5, 579–606 (1989).
Fajans, *Diabetes Care* 13, 49–64 (1990)
Froguel, Ph. et al *Nature* 356, 162–164.
Frohman N. U. et al. *Proc Natl Acad Sci U.S.A.* 85:8998 (1988)
Fukumoto H., et al. *Proc Natl Acad Sci U.S.A.* 85:5434 (1988)
Griffin, L. D. et al *Genomics* 11, 1014–1024 (1991).
Harrison, R. (1985). Ph.D. Thesis, Yale University.
Holroyde, M. J. et al. *Biochem. J.* 153, 363–373 (1976).
Hughes, S. D. et al *Proc. Natl. Acad. Sci. U.S.A.* 89, 688–692 (1992).
Jones, A. T. *Methods in Enzymology* 115, 157–171.
Kan and Dozy Proc. *Natl. Acad. Sci. U.S.A.* 75:5631 (1978)
Kidd et al. *Nature* 304:230 (1983)
Lathrop, G. M. et al. *J. Human. Genet.* 37, 482–498 (1985)
Lestradet, H. et al *Arch. Fr. Pediatr.* 46, 19–23 (1989).
Magnuson, M. A. et al *Proc. Natl. Acad. Sci. U.S.A.* 86, 4838–4842 (1989).
Magnuson, M. A. et al *J. Biol. Chem.* 264, 15936–15942 (1989).
Magnuson, M. A. *Diabetes* 39, 523–527 (1990).
Matschinsky, F. M. *Diabetes* 39, 647–652 (1990).
Matsutani A., et al. *Genomics* 12:319 (1992)
Meglasson, M. D. et al *Am. J. Physiol.* 246, E1–E13 (1984).
Meglasson, M. A. & Matschinsky, F. M. *Am. J. Physiol.* 246, 1–13 (1984)
Multicentre Study (Coord. Turner, R. C.) *Diabetologia* 24, 404–411 (1983).
Nishi S. et al. *Biochem. Biophys. Res. Commun.* 157:937 (1989)
Nishi, S. et al *Diabetologia,* in press (1992)
O'Rahilly, S. et al *Diabetologia* 31, 407–414 (1988).
O'Rahilly, S. O. & Turner, R. C. *Diab. Med.* 5, 224–229 (1988)
Orita, M. et al *Proc. Natl. Acad. Sci. U.S.A.* 86, 2766–2770 (1989a).
Orita, M. et al *Genomics* 5, 874–879 (1989b).
Pilkis, S. J. et al *Annu. Rev. Physiol.* 54, 885–909 (1992).
Piratsu, et al. *New England J. Med.* 309:284 (1983)
Rasler et al. *J. Mol. Biol.* 294m 109–1029 (1988).
Rubin and Kan *Lancet* 1985–1:75 (1985)
Saiki, R. J. et al. *Science* 239, 487–491 (1988).
Sambrook, J. et al *Molecular Cloning: A Laboratory Manual* pp. 9.14–9.23 (1989).
Sanger, F. et al *J. Mol. Biol.* 143, 161–178 (1980).
Steiner, D. F. et al *Diabetes Care* 13, 600–609 (1990).
Tanizawa, Y. et al *Proc. Natl. Acad. Sci. U.S.A.* 88, 7294–7297 (1991).
Taylor, S. I. et al *Diabetes Care* 13, 257–279 (1990).
Unger, R. H. *Science* 251, 1200–1205 (1991).
Vionnet, N. et al *Nature,* in press (1992).

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, while the glucokinase of human pancreas has special utility as described herein, other glucokinases such as human liver and rat liver and pancreatic glucokinases will find utility with the methods of the invention as well. Additionally, although a substantial number of relevant mutations have been identified using the sequences and methods of the present invention which correlate to MODY disease, other such mutations will be easily identified using the teachings and materials of the disclosure. In fact, it is not unlikley that mutations in the glucokinase gene such as those identified here may be associated with other related diseases such as the more common late-onset rarities. All such modifications are intended to be included within the scope of the appended claims.

What is claimed is:

1. A method for detecting an increased risk to develop glucokinase-linked early-onset non-insulin-dependent diabetes mellitus, comprising:

(a) obtaining a sample of DNA of a subject suspected of having diabetes; and (b) testing the DNA to detect a mutation in a glucokinase gene of the subject, wherein said mutation leads to a disorder in glucose metabolism and is associated with an increased risk to develop glucokinase-linked early-onset non-insulin-dependent diabetes mellitus.

2. The method of claim 1 where the early-onset, non-insulin-dependent diabetes mellitus comprises maturity-onset-diabetes of the young.

3. The method of claim 1 wherein testing the DNA comprises:

a) isolating the DNA of the subject to be tested for the increased risk;

b) selecting a pair of primers capable of amplifying an exon sequence of the glucokinase gene when used in conjunction with a polymerase chain reaction;

c) contacting the DNA of the subject to be tested for the increased risk with the pair of primers;

d) carrying out the polymerase chain reaction with the DNA and pair of primers to cream amplification products;

e) detecting a mutation in the DNA by analyzing the amplification products.

4. The method of claim 1 wherein the mutation is detected using an allele-specific oligonucleotide technique.

5. The method of claim 3 wherein the mutation comprises a change from C to T causing an alteration from Thr to Met at amino acid position 228 of the glucokinase protein sequence of SEQ ID NO:44.

6. The method of claim 3 wherein the mutation comprises a change from G to A causing an alteration from Gly to Arg at amino acid position 261 of the glucokinase protein sequence of SEQ ID NO:44.

7. The method of claim 3 wherein the mutation comprises a change from G to T causing an alteration from Glu to an amber nonsense codon at amino acid position 279 of the glucokinase protein sequence of SEQ ID NO:44.

8. The method of claim 3 wherein the mutation comprises a change from G to C causing an alteration from Gly to Arg at amino acid position 299 of the glucokinase protein sequence of SEQ ID NO:46.

9. The method of claim 3 wherein the mutation comprises a change from G to A causing an alteration from Glu to Lys at amino acid position 300 of the glucokinase protein sequence of SEQ ID NO:46.

10. The method of claim 3 wherein the mutation comprises a change from G to C causing an alteration from Glu to Gln at amino acid position 300 of the glucokinase protein sequence of SEQ ID NO:46.

11. The method of claim 3 wherein the mutation comprises a change from T to C causing an alteration from Leu to Pro at amino acid position 309 of the glucokinase protein sequence of SEQ ID NO: 415.

12. The method of claim 3 where the pair of primers is a pair of primers selected from the pairs of primers identified by SEQ ID NOS. 12 and 13, or SEQ ID NOS. 14 and 15, or SEQ ID NOS. 16 and 17, or SEQ ID NOS. 18 and 19, or SEQ ID NOS. 20 and 21, or SEQ ID NOS. 22 and 23, or SEQ ID NOS. 24 and 25, or SEQ ID NOS. 26 and 27, or SEQ ID NOS. 28 and 29, or SEQ ID NOS. 30 and 31, or SEQ ID NOS. 32 and 33, or SEQ ID NOS. 34 and 35.

13. The method of claim 1 wherein the glucokinase gene comprises a DNA sequence encoding an hepatocyte-derived glucokinase.

14. The method of claim 1 wherein the glucokinase gene comprises a DNA sequence encoding a pancreatic b-cell-derived glucokinase.

15. The method of either of claims 13 or 14 where the hepatocyte- or pancreatic b-cell-derived further comprises a human glucokinase.

* * * * *

UNITED STATES PATENT AND TRADEMARK OFFICE

CERTIFICATE OF CORRECTION

PATENT NO. : 5,541,060

DATED : July 30, 1996

INVENTOR(S) : Graeme I. Bell, et al

It is certified that error appears in the above-indentified patent and that said Letters Patent is hereby corrected as shown below:

In claim 3(d), column 58, line 49, delete "cream" and substitute --create--.

Signed and Sealed this

Twelfth Day of November, 1996

Attest:

BRUCE LEHMAN

*Attesting Officer*

*Commissioner of Patents and Trademarks*

UNITED STATES PATENT AND TRADEMARK OFFICE

CERTIFICATE OF CORRECTION

PATENT NO. : 5,541,060

DATED : July 30, 1996

INVENTOR(S) : Bell et al.

It is certified that error appears in the above-identified patent and that said Letters Patent is hereby corrected as shown below:

In Claim 3, column 58, line 49, delete "cream" and insert --create-- therefore.

In Claim 11, column 59, line 14, delete "SEQ ID NO:415" and insert --SEQ ID NO:46-- therefor.

Signed and Sealed this

Seventeenth Day of December, 1996

Attest:

BRUCE LEHMAN

Attesting Officer

Commissioner of Patents and Trademarks

UNITED STATES PATENT AND TRADEMARK OFFICE

CERTIFICATE OF CORRECTION

PATENT NO. : 5,541,060
APPLICATION NO. : 07/872678
DATED : July 30, 1996
INVENTOR(S) : Graeme I. Bell et al.

It is certified that error appears in the above-identified patent and that said Letters Patent is hereby corrected as shown below:

Replace Figures 6A-6R (sheets 7-24) with the attached replacement drawings labeled FIGS. 6A-6F (six sheets).

In column 4, lines 16-18, delete "FIG. 6A, FIG. 6B, FIG. 6C, FIG. 6D, FIG. 6E, FIG. 6F, FIG. 60, FIG. 6H, FIG. 6I, FIG. 6J, FIG. 6K, FIG. 6L, FIG. 6M, FIG. 6N, FIG. 6O, FIG. 6P, FIG. 6Q, FIG. 6R" and insert -- FIG. 6A-FIG. 6F -- therefor.

In column 4, lines 37-39, delete "FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R" and insert -- FIG. 6A-FIG. 6F -- therefor.

In column 5, lines 6-9, delete "FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R" and insert -- FIG. 6A-FIG. 6F -- therefor.

In column 5, lines 14-17, delete "FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R" and insert -- FIG. 6A-FIG. 6F -- therefor.

In column 5, lines 20-22, delete "FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R" and insert -- FIG. 6A-FIG. 6F -- therefor.

In column 5, lines 24-26, delete "FIG. 6A, FIG. 6B, FIG. 6C, FIG. 6D, FIG. 6E, FIG. 6F, FIG. 60, FIG. 6H, FIG. 6I, FIG. 6J, FIG. 6K, FIG. 6L, FIG. 6M, FIG. 6N, FIG. 6O, FIG. 6P, FIG. 6Q, FIG. 6R" and insert -- FIG. 6A-FIG. 6F -- therefor.

In column 5, lines 29-31, delete "FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R" and insert -- FIG. 6A-FIG. 6F -- therefor.

Signed and Sealed this

Eighth Day of June, 2010

David J. Kappos
*Director of the United States Patent and Trademark Office*

In column 5, lines 34-37, delete “FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R” and insert -- FIG. 6A-FIG. 6F -- therefor.

In column 5, lines 39-42, delete “FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R” and insert -- FIG. 6A-FIG. 6F -- therefor.

In column 7, line 1, delete “FIGS. 6A-6R” and insert -- FIG. 6A-FIG. 6F -- therefor.

In column 8, lines 11-13, delete “FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R” and insert -- FIG. 6A-FIG. 6F -- therefor.

In column 15, line 67 to column 16, lines 1-2, delete “FIG. 6A, FIG. 6B, FIG. 6C, FIG. 6D, FIG. 6E, FIG. 6F, FIG. 6G, FIG. 6H, FIG. 6I, FIG. 6J, FIG. 6K, FIG. 6L, FIG. 6M, FIG. 6N, FIG. 6O, FIG. 6P, FIG. 6Q, FIG. 6R” and insert -- FIG. 6A-FIG. 6F -- therefor.

In columns 53 and 54, at amino acid position 70 of SEQ ID NO:47, please delete “Gln” and insert -- Glu -- therefor.

In claim 5, column 58, line 57, delete “SEQ ID NO:44” and insert -- SEQ ID NO:47 -- therefor.

In claim 6, column 58, line 61, delete “SEQ ID NO:44” and insert -- SEQ ID NO:47 -- therefor.

In claim 7, column 58, line 65, delete “SEQ ID NO:44” and insert -- SEQ ID NO:47 -- therefor.

In claim 8, column 59, line 2, delete “SEQ ID NO:46” and insert -- SEQ ID NO:47 -- therefor.

In claim 9, column 59, line 6, delete “SEQ ID NO:46” and insert -- SEQ ID NO:47 -- therefor.

In claim 10, column 59, line 10, delete “SEQ ID NO:46” and insert -- SEQ ID NO:47 -- therefor.

In claim 11, column 59, line 14, delete “SEQ ID NO:46” and insert -- SEQ ID NO:47 -- therefor.

```
AGGAGGAGCCAGTCCCTGTGGCCTCTGTTCTGACAGTGTCAACCTCAGCCAGGCTTGTGGGCCAGGTGTACTGTTGTGGTTCAGATTTCAAGGAGATAGTCAGGGCAGGCCGCGCAAAGCC
CTCCGATGGGCTCCCCTACTGCCTGGCAGACCTGTCCAGCTTTGGACTCTGGCCCTGCGACCTGTCCAGCTTTGGACTCTGGCCCTGCGACCTGGAAGTCAGGCTGCCAAGAGGTCCAGGC
AGTGGCTCCACTGTGGAGGGTCTCTGGAGAGTTTACAGCCCTAGATAGGGGGGTTAGGGATGTGAGATGGTCCCAGGGGCCTGCTCCTGAGCCACGCCAAGCTGCCTGCTCCCTTTCCTCT
GCTTCCAGACTCACGGGATCCTCTGCTCATCAGAACAGGAGTGTGGGAGACCCTGAGACACTGCCCCAGGATCTGAACAGGTGGCAAAGGCTTAACAGGCTAGCGTGCACTGTAGTGACAA
GGCGATTGAGTGGTCACCATGGTGATGGGGATGGAGGCTCTTTGCCACCAGTCCCAGTTTTATGCATGGCAGCTCTAATGACAGGATGGTCAGCCCTGCTGAGGCCACTCCTGGTCACCAT
GACAACCACAGGCCCTCTCAGGAGCACAGTAAGCCCTGGCAGGAGAATCCCCCACTCCACACCTGGCTGGAGCAGGAAATGCCGAGCGGCGCCTGAGCCCCAGGGAAGCAGGCTAGGATGT
GAGAGACACAGTCACCTGCAGCCTAATTACTCAAAAGCTGTCCCCAGGTCACAGAAGGGAGAGGACATTTCCCACTGAATCTGTCTGAAGGACACTAAGCCCCACAGCTCAACACAACCAG
GAGAGAAAGTGCTGAGGACGCCACCCAAGCGCCCAGCAATGGCCCTGCCTGGAGAACATCCAGGCTCAGTGAGGAAGGGTCCAGAAGGGAATGCTTGCCGACTCGTTGGAGAACAATGAAA
AGGAGAAACTGTGACTGAACCTCAAACCCCAAACCAGCCCGAGGAGAACCACATTCTCCCAGGGACCCAGGGCGGGCCTGACCCCTGCGGCGGAGAAGCCTTGGATATTTCCACTTCAGAA
                                                Exon 1a   1                                      10                   15
                                                          Met Leu Asp Asp Arg Ala Arg Met Glu Ala Ala Lys Lys Glu Lys
GCCTACTGGGGAAGGCTGAGGGGTCCCAGCTCCCCACGCTGGCTGCTGTGCAC     ATG CTG GAC GAC AGA GCC AGG ATG GAG GCC GCC AAG AAG GAG AAG GTAT
CTCGCCCTCCATTGGGCATTCTGGGAGTGTTTGCTTGCCTGTCCCCAACATTCCATGGTTTGTTTGAGCCTCAGAATCTGATTTTATGCACAGGCTCTTTGAGAAGGGTCTTGCCAGGGGT
GCCTTCTGGGGCAGGAAGGCCTACTGCCTGGCAGACCCATCCAGCTTTGGACTCTGGTCCTGCGACCCGGAAGTCAGGCGTCCAAGAGGTC:::::: >8 kb ::::::GGGATCCCCT
TGCCTCCAAGAGCAAGTCCAGACCTGCACCAGCGCGGGCCAGGCCCCCTTAGGACCCCCTCCCTGTCCAAGGGCATTTCAGTAAGTGTTCTGTGGCCAAGGCAGCCTGGTGACTTTCTGCC
CGCACAAGGCTGAGGAATGGAAGATGGGTAGGCTCTGCACACCCCCTCCTGCTGGGCAGCAATCCCTACCCCATGTTCACAGAGTGTGGCCGGCTGCCCCATGGCTCTGTCCCCGTGGCCC
TGTCAACTGTTACCCCACATGGGCCTACCCTCCCTTTCTGGCCCTGCCTCTGACCCCATGGCAGGGGGCAGAGTATTTGAGCAGCCGCCAGCTGAGCCCTTTCAGTGCAGAAGCCCTGGGC
```

FIG. 6A

```
TGCCAGCCTCAGGCAGCTCTCCATCCAAGCAGCCGTTGCTGCCACAGGCGGGCCTTACGCTCCAAGGCTACAGCATGTGCTAGGCCTCAGCAGGCAGGAGCATCTCTGCCTCCCAAAGCAT
                 Exon 1b  1                                    10                     16
                          Met Ala Met Asp Val Thr Arg Ser Gln Ala Gln Thr Ala Leu Thr Leu
CTACCTCTTAGCCCCTCGGAGAG ATG GCG ATG GAT GTC ACA AGG AGC CAG GCC CAG ACA GCC TTG ACT CTG GTAAGGGTCACACCAAAGTTAGGGACTTTGCAC

TGGGAGAGCAGCACCCAGGGCAGGGCCTTGGTTTTGCAGATTACCAAAACTAAGGCTGGGGGCAGGGAAGGCGAGCAGGCTTGGGGCACCTTGGAAGGAGGCACATGGGCTTGGGGGTCCT
GGCTAGGGCAGCTGTGCCTC:::::: 0.6 kb ::::::CTGCAGCATCTGCCCAGGGACTGCCCTGGCCCTTGGCATTTCCTCAGGGACCCACAGCTCCACCAGCCGGCCCCTCCCAGT
GCTGGAATAGACAGTTCCTCAGTCCACATCTGCCAAAGGCGGCACTAGAAGGCATCCTGCCTTTTTTACTGCGTTCTGGAGGTGGGGTCACAAAGCACTGCTCACTGCATAAAAGGGACAG
CATCCTGCCCCTGGCAGCCCTGCCTGACCAGCTCCGCCTCTCCCACTGCTATCCAACCTGTACACCCTGGTGACCATGTCCAGGCCAGTGGCCTTAAGGACTGTCTCTGTACTGATGGCTC
                   Exon 1c                                                                                       1
                                                                                                                 Met Pro Arg Pro Arg
CACATCTACCTCTCCAG  CCAGACTCTCCTCTGAACTCGGGCCTCACATGGCCAACTGCTACTTGGAACAAATCGCCCCTTGGCTGGCAGATGTGTTAAC ATG CCC AGA CCA AGA
                10             14
Ser Gln Leu Pro Gln Pro Asn Ser Gln
TCC CAA CTC CCA CAA CCC AAC TCC CAG GTCAGATGGAACCTCTTCTTCCCAGGCCCTTCTGTTCCTCTCCTCAGCCCCTCCCACCTCCCTTCAGAATAAGTCTAGACTCTTA
TCGCTTTCACCAAGCCTGCGCCCAGCATCCCTGCACAGGGATTGTTAGGACAGCCTGACGCCCTGCTTCCACCCTGCCCCAAGATGCCCTGCTCTGCAG:::::: 4.3 kb ::::::GG
GACGAAGCAGGGTGCTACAGGACGCTGTGCCACAGGGATATCGTCAGGGACAGAAGCTACTCTGCCCTCTGCTGCTCACCCCTCCAACACGCTGTGGGCTGCATTTGTTGAGTGGCTGGTA
CCAGACTCTGCTCTTCTGACTTTCCAGCTGGTTTTACCTGTAGTAAAGTTTGAGAAGATGGTCATCCTGACCCCGGGGTCAGAAGACAGAAGGAGGCCCATGGCGTGTGGGGGAGATGCCC
                                                                                                          Exon 2  16
                                                                                                                Val Glu Gln Ile
CGTGAGGCCCTCGGTGTGCAGATGCCTGGTGACAGCCCCACCCTGAGGTCCCCAGCCTACCCCCTCCCCAGCCCGACTGCTCCCATCCCCCTCCCTGTGCAG   GTA GAG CAG ATC
 20                                  30                                      40
Leu Ala Glu Phe Gln Leu Gln Glu Glu Asp Leu Lys Lys Val Met Arg Arg Met Gln Lys Glu Met Asp Arg Gly Leu Arg Leu Glu Thr
CTG GCA GAG TTC CAG CTG CAG GAG GAG GAC CTG AAG AAG GTG ATG AGA CGG ATG CAG AAG GAG ATG GAC CGC GGC CTG AGG CTG GAG ACC
 50                                  60                                      70
His Glu Glu Ala Ser Val Lys Met Leu Pro Thr Tyr Val Arg Ser Thr Pro Glu Gly Ser G(lu)
CAT GAA GAG GCC AGT GTG AAG ATG CTG CCC ACC TAC GTG CGC TCC ACC CCA GAA GGC TCA G GTACCACATGGTAACCGGCTCCTCATCCAGAAGCAGCTGT
```

FIG. 6B

GGGCTCAGCCTAGCTGGGAGAAGCACCCCAGGCACTCCCAGACTCACAGCCAGCCCGAGACAGAATCTCCTGGGGAGCAATGAAGTCCTCGACTTGGGCCAGTTCTCACCCTTGGCTCCTC
TGGTCCGGCCCTGGGGCACTCGGGCTCACCCTGGAGCTGGCAAACCTCAGGAAAACTGGCGTTTTAA:::::: 1.2 kb ::::::TCCCTTGTGCCTTCCCTCCTCCTCTTTGTAATAT
*Exon 3* 70
(G)lu Val Gly Asp Phe Leu Ser Leu
CCGGCTCAGTCACCTGGGGCCCACCCAGCCCAAGGCCAGCCTGTGGGTGTCCCTGAGGCTGACACACTTCTCTCTGTGCCTTTAG AA GTC GGG GAC TTC CTC TCC CTG
80 90 100
Asp Leu Gly Gly Thr Asn Phe Arg Val Met Leu Val Lys Val Gly Glu Gly Glu Glu Gly Gln Trp Ser Val Lys Thr Lys His Gln Met
GAC CTG GGT GGC ACT AAC TTC AGG GTG ATG CTG GTG AAG GTG GGA GAA GGT GAG GAG GGG CAG TGG AGC GTG AAG ACC AAA CAC CAG ATG
110 120 121
Tyr Ser Ile Pro Glu Asp Ala Met Thr Gly Thr Ala Glu Met
TAC TCC ATC CCC GAG GAC GCC ATG ACC GGC ACT GCT GAG ATG GTGAGCAGCGCAGGGGCCGGGGCAGGGGGCAAGGCATGCAGGATCTCAGGGCCCAGCTAGTCCTG ACGGGAGGTGCCACCTGTCTACCAGGGGTGGGGAGAGCGGGGGCTGGAGGACCACCCAGCCTCAGAGGCAGCTGGAGGCCTGGGTGAACAGGACT:::::: 1.7 kb ::::::GACAGG
*Exon*
CCTGGCATTCAGTGGCCAGGTGTTGCAGTGTCCCTGAGGAATAGCTTGGCTTGAGGCCGTGGGGAGGGCTGCCGGCCAGCGCACCCCCCCATGCCAGATGGTCACCATGGCGTGCATCTTC
*4* 122 130 140 150
Leu Phe Asp Tyr Ile Ser Glu Cys Ile Ser Asp Phe Leu Asp Lys His Gln Met Lys His Lys Lys Leu Pro Leu Gly Phe Thr Phe
CAG CTC TTC GAC TAC ATC TCT GAG TGC ATC TCC GAC TTC CTG GAC AAG CAT CAG ATG AAA CAC AAG AAG CTG CCC CTG GGC TTC ACC TTC 160 161
Ser Phe Pro Val Arg His Glu Asp Ile Asp Lys
TCC TTT CCT GTG AGG CAC GAA GAC ATC GAT AAG GTGGGCCGGGTGGAGGGGCAGAAGGCAGATGAGGGGAGGCACAGGCACCCCAGAGGAACTCTGCCTTCAAATGTAGC

FIG. 6C

```
CCCCATACCCTGTGCTCAGAAGGGAGATCTGGATTCAAATTGTGGCCATGTCACCTGCCACTCTAATGCTGTGGAAAAGAAGCATCACATTAGCTAATTCTGGCTGTGCGCCTTGTGAGGC
ACCAGCTATGATCACCCCACTCCAGTGGAAAGAGCAGCTGGCAGTAGGGTGGGGCTCAAACTCAGGCAGCCGGCTCTGGGTCATCAGCCAGTCATGTCACATGCCTATGCTAGTCAGAATG
                                                                                        Exon 5  162                            170
                                                                                                Gly Ile Leu Leu Asn Trp Thr Lys Gly Phe
TG::::: 0.9 kb ::::::CCCTAGCACCCTGCCTCCAGATATGTTAGCAGCCACGAGGCCTATCTCTCCCCACAG  GGC ATC CTT CTC AAC TGG ACC AAG GGC TTC
                                180                                     190         193
Lys Ala Ser Gly Ala Glu Gly Asn Asn Val Val Gly Leu Leu Arg Asp Ala Ile Lys Arg Arg Gly
AAG GCC TCA GGA GCA GAA GGG AAC AAT GTC GTG GGG CTT CTG CGA GAC GCT ATC AAA CGG AGA GGG GTGAGGGGGCACCTGTACCTGCCGGGGGGGCTG
                                                                                    Exon 6  194                     200
                                                                                            Asp Phe Glu Met Asp Val Val Ala Met Val Asn
CCCTGGGCCACCCACCCCAGCACTGCCTGCCTTTCTCCTTGGCTTCCAGCACTGCAGCTTCTGTGCTTCTTGGCAG GAC TTT GAA ATG GAT GTG GTG GCA ATG GTG AAT
                    210                                     220                         227
Asp Thr Val Ala Thr Met Ile Ser Cys Tyr Tyr Glu Asp His Gln Cys Glu Val Gly Met Ile Val G(ly)
GAC ACG GTG GCC ACG ATG ATC TCC TGC TAC TAC GAA GAC CAT CAG TGC GAG GTC GGC ATG ATC GTG G GTAAGGGCTCCTTGCACCCCTGCCCCTTCCAG
ACTGCCGAGGCTCCCTGTGTACAACAGGCTTCAAGGGCCCTGTGGGTGAGGGCCAAACTACTTAACAACCGGTGATGTCAGAGCAGAGCCTGGTGCTACAGCCTGGGTGGTCTTGGGGTAT
                                                                                                          Exon 7  227  Met (F391)
                                                                                                                   (G)ly Thr Gly Cys Asn
CAAGATGGAAGC:::::: 1.9 kb ::::::GGCAGGAACCAGGCCCTACTCCGGGGCAGTGCAGCTCTCGCTGACAGTCCCCCCGACCTCCACCCCAG  GC ACG GGC TGC AAT
                                240                                     250                                 T     260 Arg (F388
Ala Cys Tyr Met Glu Glu Met Gln Asn Val Glu Leu Val Glu Gly Asp Glu Gly Arg Met Cys Val Asn Thr Glu Trp Gly Ala Phe Gly /390)
GCC TGC TAC ATG GAG GAG ATG CAG AAT GTG GAG CTG GTG GAG GGG GAC GAG GGC CGC ATG TGC GTC AAT ACC GAG TGG GGC GCC TTC GGG
                                270                                     AM (F8)                         288         A
Asp Ser Gly Glu Leu Asp Glu Phe Leu Leu Glu Tyr Asp Arg Leu Val Asp Glu Ser Ser Ala Asn Pro Gly Gln Gln Le(u)
GAC TCC GGC GAG CTG GAC GAG TTC CTG CTG GAG TAT GAC CGC CTG GTG GAC GAG AGC TCT GCA AAC CCC GGT CAG CAG CT GTAAGGATGCCCCC
                                                                        T
CTCCCCCACAACCCAGGCCCTGGGCGCTCTGGTGCAGCGGCAGATGGGAGCCGGGCCATTGCAGATAATGGGCTTGTTTTTAAACAACTCTGGGGAAAAGCAAACTGACAATCCGTTCGTA
```

*FIG. 6D*

```
AGCTCCATCCCTTCTGCTCAGTCATGACCTGCCCCTGTGAGAGATGAAGGGTTAGTCCCAGTTGTGATGTGATAAGCCCAGACCTCTTTCCTTCCGACAGGTGAT:::: 1.0 kb ::::
                                                                                                     Exon 8   288     290
                                                                                                            (Le)u Tyr Glu Lys Leu
::::CCTCAGTGGGGAGCACTGGGGCCGGCTCCCGGCTTCCACCTGCATGAGGGGCCCTCCCTCGTGCCTGCTGATGTAATGGTCCTGCCCTATGTCCAG   G TAT GAG AAG CTC
                                                                        310                                   320
Ile Gly Gly Lys Tyr Met Gly Glu Leu Val Arg Leu Val Leu Leu Arg Leu Val Asp Glu Asn Leu Leu Phe His Gly Glu Ala Ser Glu
ATA GGT GGC AAG TAC ATG GGC GAG CTG GTG CGG CTT GTG CTG CTC AGG CTC GTG GAC GAA AAC CTG CTC TTC CAC GGG GAG GCC TCC GAG
                                                                        340
Gln Leu Arg Thr Arg Gly Ala Phe Glu Thr Arg Phe Val Ser Gln Val Glu Se(r)
CAG CTG CGC ACA CGC GGA GCC TTC GAG ACG CGC TTC GTG TCG CAG GTG GAG AG GTGTGCGGAGGAGGAGGGTGGGTGCAAAGGCAGGGGCTGGGGTCGCCCG

GGCACTGCAGACTTGGTCTCAGGGCGACGCTGAGTCCCAGGCCCGGGGCGCAGGGACGGGAAACTAGGGCCTGGGGCGGGATTCCGGGCGTGGG::::: 0.5 kb :::::GCTGGGG
                                                                                                          Exon 9  340
                                                                                                               (Se)r Asp Thr Gly
GACGGCTGGCCGGGGCCCCTCCCTGGAGAACGAGAGGCCGCCGCTGGAGGGGGATGGACTGTCGGAGCGACACTCAGCGACCGCCCTACCTCCTCCCGCCCCGCAG C GAC ACG GGC
                     350                                 360                                 370
Asp Arg Lys Gln Ile Tyr Asn Ile Leu Ser Thr Leu Gly Leu Arg Pro Ser Thr Thr Asp Cys Asp Ile Val Arg Arg Ala Cys Glu Ser
GAC CGC AAG CAG ATC TAC AAC ATC CTG AGC ACG CTG GGG CTG CGA CCC TCG ACC ACC GAC TGC GAC ATC GTG CGC CGC GCC TGC GAG AGC
```

*FIG. 6E*

```
                    380                                     390                                     400
Val Ser Thr Arg Ala Ala His Met Cys Ser Ala Gly Leu Ala Gly Val Ile Asn Arg Met Arg Glu Ser Arg Ser Glu Asp Val Met Arg
GTG TCT ACG CGC GCT GCG CAC ATG TGC TCG GCG GGG CTG GCG GGC GTC ATC AAC CGC ATG CGC GAG AGC CGC AGC GAG GAC GTA ATG CGC
                    410                             418
Ile Thr Val Gly Val Asp Gly Ser Val Tyr Lys Leu His Pro Se(r)
ATC ACT GTG GGC GTG GAT GGC TCC GTG TAC AAG CTG CAC CCC AG GTGAGCCCGCCCCGCTCTCTCCCTGGTAAAGTGGGGCCCAAAAAGCGCGCGCTCCAAGGTTC
                                                                                    T
CTTGCGGTTCCCAAGCTCCAAGATTTCGTAGTCCTCTTCTCGTCCCCCTTGGCCTAGATTTGGGGGAAGGGTCGACTGCGTGCAGGGCGCCCGGTAATGAATGTGGAGGATGAGGTGGGAG
GA:::::: 0.7 kb ::::::TAGAGTCTTCTCGACCCCCTTGGCCTAGATTTGGGGGAAGGGTCGACTGCGTGCAGGGCGCCCGGTAATGAATGTGGAGGATGAGGTGGGAGGAGGGAC
               Exon 10  418     420                                     430                                     440
                          (Se)r Phe Lys Glu Arg Phe His Ala Ser Val Arg Arg Leu Thr Pro Ser Cys Glu Ile Thr Phe Ile Glu Ser
GGCAGCCCTGCTTCTCTTCTGCCCAG C TTC AAG GAG CGG TTC CAT GCC AGC GTG CGC AGG CTG ACG CCC AGC TGC GAG ATC ACC TTC ATC GAG TCG
                                450                                     460                 465
Glu Glu Gly Ser Gly Arg Gly Ala Ala Leu Val Ser Ala Val Ala Cys Lys Lys Ala Cys Met Leu Gly Gln OP
GAG GAG GGC AGT GGC CGG GGC GCG GCC CTG GTC TCG GCG GTG GCC TGT AAG AAG GCC TGT ATG CTG GGC CAG TGA GAGCAGTGGCCGCAAGCGCAG
GGAGGATGCCACAGCCCCACAGCACCCAGGCTCCATGGGGAAGTGCTCCCCACACGTGCTCGCAGCCTGGCGGGGCAGGAGGCCTGGCCTTGTCAGGACCCAGGCCGCCTGCCATACCGCT
GGGGAACAGAGCGGGCCTCTTCCCTCAGTTTTTCGGTGGGACAGCCCCAGGGCCCTAACGGGGGTGCGGCAGGAGCAGGAACAGAGACTCTGGAAGCCCCCCACCTTTCTCGCTGGAATCA
ATTTCCCAGAAGGGAGTTGCTCACTCAGGACTTTGATGCATTTCCACACTGTCAGAGCTGTTGGCCTCGCCTGGGCCCAGGCTCTGGGAAGGGGTGCCCTCTGGATCCTGCTGTGGCCTCA
CTTCCCTGGGAACTCATCCTGTGTGGGGAGGCAGCTCCAACAGCTTGACCAGACCTAGACCTGGGCCAAAAGGGCAGCCAGGGGCTGCTCATCACCCAGTCCTGGCCATTTTCTTGCCTGA
GGCTCAAGAGGCCCAGGGAGCAATGGGAGGGGGCTCCATGGAGGAGGTGTCCCAAGCTTTGAATACCCCCAGAGACCTTTTCTCTCCCATACCATCACTGAGTGGCTTGTGATTCTGGGAT
GGACCCTCGCAGCAGGTGCAAGAGACAGAGCCCCCAAGCCTCTGCCCCAAGGGGCCCACAAAGGGGAGAAGGGCCAGCCCTACATCTTCAGCTCCCATAGCGCTGGCTCAGGAAGAAACCC
CAAGCAGCATTCAGCACACCCCAAGGGACAACCCCATCATATGACATGCCACCCTCTCCATGCCCAACCTAAGATTGTGTGGGTTTTTTAATTAAAAATGTTAAAAGTTTT
```

*FIG. 6F*

UNITED STATES PATENT AND TRADEMARK OFFICE

CERTIFICATE OF CORRECTION

PATENT NO. : 5,541,060
APPLICATION NO. : 07/872678
DATED : July 30, 1996
INVENTOR(S) : Bell et al.

It is certified that error appears in the above-identified patent and that said Letters Patent is hereby corrected as shown below:

In Claim 3, column 58, line 49, delete "cream" and insert --create-- therefore.

In Claim 11, column 59, line 14, delete "SEQ ID NO:415" and insert --SEQ ID NO:46-- therefore.

Signed and Sealed this

Nineteenth Day of October, 2010

David J. Kappos

*Director of the United States Patent and Trademark Office*

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
( A ) LENGTH: 1403 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
AGGAGGAGCC AGTCCCTGTG GCCTCTGTTC TGACAGTGTC AACCTCAGCC AGGCTTGTGG      60
GCCAGGTGTA CTGTTGTGGT TCAGATTTCA AGGAGATAGT CAGGGCAGGC CGCGCAAAGC     120
CCTCCGATGG GCTCCCCTAC TGCCTGGCAG ACCTGTCCAG CTTTGGACTC TGGCCCTGCG     180
ACCTGTCCAG CTTTGGACTC TGGCCCTGCG ACCTGGAAGT CAGGCTGCCA AGAGGTCCAG     240
GCAGTGGCTC CACTGTGGAG GGTCTCTGGA GAGTTTACAG CCCTAGATAG GGGGGTTAGG     300
GATGTGAGAT GGTCCCAGGG GCCTGCTCCT GAGCCACGCC AAGCTGCCTG CTCCCTTTCC     360
TCTGCTTCCA GACTCACGGG ATCCTCTGCT CATCAGAACA GGAGTGTGGG AGACCCTGAG     420
ACACTGCCCC AGGATCTGAA CAGGTGGCAA AGGCTTAACA GGCTAGCGTG CACTGTAGTG     480
ACAAGGCGAT TGAGTGGTCA CCATGGTGAT GGGGATGGAG GCTCTTTGCC ACCAGTCCCA     540
GTTTTATGCA TGGCAGCTCT AATGACAGGA TGGTCAGCCC TGCTGAGGCC ACTCCTGGTC     600
ACCATGACAA CCACAGGCCC TCTCAGGAGC ACAGTAAGCC CTGGCAGGAG AATCCCCCAC     660
TCCACACCTG GCTGGAGCAG GAAATGCCGA GCGGCGCCTG AGCCCCAGGG AAGCAGGCTA     720
GGATGTGAGA GACACAGTCA CCTGCAGCCT AATTACTCAA AAGCTGTCCC CAGGTCACAG     780
AAGGGAGAGG ACATTTCCCA CTGAATCTGT CTGAAGGACA CTAAGCCCCA CAGCTCAACA     840
CAACCAGGAG AGAAAGTGCT GAGGACGCCA CCCAAGCGCC CAGCAATGGC CCTGCCTGGA     900
GAACATCCAG GCTCAGTGAG GAAGGGTCCA GAAGGGAATG CTTGCCGACT CGTTGGAGAA     960
CAATGAAAAG GAGAAACTGT GACTGAACCT CAAACCCCAA ACCAGCCCGA GGAGAACCAC    1020
ATTCTCCCAG GGACCCAGGG CGGGCCTGAC CCCTGCGGCG GAGAAGCCTT GGATATTTCC    1080
ACTTCAGAAG CCTACTGGGG AAGGCTGAGG GGTCCCAGCT CCCCACGCTG GCTGCTGTGC    1140
AGATGCTGGA CGACAGAGCC AGGATGGAGG CCGCCAAGAA GGAGAAGGTA TCTCGCCCTC    1200
CATTGGGCAT TCTGGGAGTG TTTGCTTGCC TGTCCCCAAC ATTCCATGGT TTGTTTGAGC    1260
CTCAGAATCT GATTTTATGC ACAGGCTCTT TGAGAAGGGT CTTGCCAGGG GTGCCTTCTG    1320
GGGCAGGAAG GCCTACTGCC TGGCAGACCC ATCCAGCTTT GGACTCTGGT CCTGCGACCC    1380
GGAAGTCAGG CGTCCAAGAG GTC                                            1403
```

( 2 ) INFORMATION FOR SEQ ID NO:2:

-continued ( i ) SEQUENCE CHARACTERISTICS:
( A ) LENGTH: 739 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

GGGATCCCCT TGCCTCCAAG AGCAAGTCCA GACCTGCACC AGCGCGGGCC AGGCCCCCTT 60
AGGACCCCCT CCCTGTCCAA GGGCATTTCA GTAAGTGTTC TGTGGCCAAG GCAGCCTGGT 120
GACTTTCTGC CCGCACAAGG CTGAGGAATG GAAGATGGGT AGGCTCTGCA CACCCCCTCC 180
TGCTGGGCAG CAATCCCTAC CCCATGTTCA CAGAGTGTGG CCGGCTGCCC CATGGCTCTG 240
TCCCCGTGGC CCTGTCAACT GTTACCCCAC ATGGGCCTAC CCTCCCTTTC TGGCCCTGCC 300
TCTGACCCCA TGGCAGGGGG CAGAGTATTT GAGCAGCCGC CAGCTGAGCC CTTTCAGTGC 360
AGAAGCCCTG GGCTGCCAGC CTCAGGCAGC TCTCCATCCA AGCAGCCGTT GCTGCCACAG 420
GCGGGCCTTA CGCTCCAAGG CTACAGCATG TGCTAGGCCT CAGCAGGCAG GAGCATCTCT 480
GCCTCCCAAA GCATCTACCT CTTAGCCCCT CGGAGAGATG GCGATGGATG TCACAAGGAG 540
CCAGGCCCAG ACAGCCTTGA CTCTGGTAAG GGTCACACCA AAGTTAGGGA CTTTGCACTG 600
GGAGAGCAGC ACCCAGGGCA GGGCCTTGGT TTTGCAGATT ACCAAAACTA AGGCTGGGGG 660
CAGGGAAGGC GAGCAGGCTT GGGGCACCTT GGAAGGAGGC ACATGGGCTT GGGGGTCCTG 720
GCTAGGGCAG CTGTGCCTC 739

( 2 ) INFORMATION FOR SEQ ID NO:3:

( i ) SEQUENCE CHARACTERISTICS:
( A ) LENGTH: 648 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

CTGCAGCATC TGCCCAGGGA CTGCCCTGGC CCTTGGCATT TCCTCAGGGA CCCACAGCTC 60
CACCAGCCGG CCCCTCCCAG TGCTGGAATA GACAGTTCCT CAGTCCACAT CTGCCAAAGG 120
CGGCACTAGA AGGCATCCTG CCTTTTTTAC TGCGTTCTGG AGGTGGGGTC ACAAAGCACT 180
GCTCACTGCA TAAAAGGGAC AGCATCCTGC CCCTGGCAGC CCTGCCTGAC CAGCTCCGCC 240
TCTCCCACTG CTATCCAACC TGTACACCCT GGTGACCATG TCCAGGCCAG TGGCCTTAAG 300
GACTGTCTCT GTACTGATGG CTCCACATCT ACCTCTCCAG CCAGACTCTC CTCTGAACTC 360
GGGCCTCACA TGGCCAACTG CTACTTGGAA CAAATCGCCC CTTGGCTGGC AGATGTGTTA 420
ACATGCCCAG ACCAAGATCC CAACTCCCAC AACCCAACTC CCAGGTCAGA TGGAACCTCT 480
TCTTCCCAGG CCCTTCTGTT CCTCTCCTCA GCCCCTCCCA CCTCCCTTCA GAATAAGTCT 540
AGACTCTTAT CGCTTTCACC AAGCCTGCGC CCAGCATCCC TGCACAGGGA TTGTTAGGAC 600
AGCCTGACGC CCTGCTTCCA CCCTGCCCCA AGATGCCCTG CTCTGCAG 648

( 2 ) INFORMATION FOR SEQ ID NO:4:

( i ) SEQUENCE CHARACTERISTICS:
( A ) LENGTH: 737 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:4:

```
GGGACGAAGC AGGGTGCTAC AGGACGCTGT GCCACAGGGA TATCGTCAGG GACAGAAGCT    60
ACTCTGCCCT CTGCTGCTCA CCCCTCCAAC ACGCTGTGGG CTGCATTTGT TGAGTGGCTG   120
GTACCAGACT CTGCTCTTCT GACTTTCCAG CTGGTTTTAC CTGTAGTAAA GTTTGAGAAG   180
ATGGTCATCC TGACCCCGGG GTCAGAAGAC AGAAGGAGGC CCATGGCGTG TGGGGGAGAT   240
GCCCCGTGAG GCCCTCGGTG TGCAGATGCC TGGTGACAGC CCCACCCTGA GGTCCCCAGC   300
CTACCCCCTC CCCAGCCCGA CTGCTCCCAT CCCCCTCCCT GTGCAGGTAG AGCAGATCCT   360
GGCAGAGTTC CAGCTGCAGG AGGAGGACCT GAAGAAGGTG ATGAGACGGA TGCAGAAGGA   420
GATGGACCGC GGCCTGAGGC TGGAGACCCA TGAAGAGGCC AGTGTGAAGA TGCTGCCCAC   480
CTACGTGCGC TCCACCCCAG AAGGCTCAGG TACCACATGG TAACCGGCTC CTCATCCAGA   540
AGCAGCTGTG GGCTCAGCCT AGCTGGGAGA AGCACCCCAG GCACTCCCAG ACTCACAGCC   600
AGCCCGAGAC AGAATCTCCT GGGGAGCAAT GAAGTCCTCG ACTTGGGCCA GTTCTCACCC   660
TTGGCTCCTC TGGTCCGGCC CTGGGGCACT CGGGCTCACC CTGGAGCTGG CAAACCTCAG   720
GAAAACTGGC GTTTTAA                                                 737
```

( 2 ) INFORMATION FOR SEQ ID NO:5:

( i ) SEQUENCE CHARACTERISTICS:
( A ) LENGTH: 434 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

```
TCCCTTGTGC CTTCCCTCCT CCTCTTTGTA ATATCCGGCT CAGTCACCTG GGGCCCACCC    60
AGCCCAAGGC CAGCCTGTGG GTGTCCCTGA GGCTGACACA CTTCTCTCTG TGCCTTTAGA   120
AGTCGGGGAC TTCCTCTCCC TGGACCTGGG TGGCACTAAC TTCAGGGTGA TGCTGGTGAA   180
GGTGGGAGAA GGTGAGGAGG GGCAGTGGAG CGTGAAGACC AAACACCAGA TGTACTCCAT   240
CCCCGAGGAC GCCATGACCG GCACTGCTGA GATGGTGAGC AGCGCAGGGG CCGGGGCAGG   300
GGGCAAGGCA TGCAGGATCT CAGGGCCCAG CTAGTCCTGA CGGGAGGTGC CACCTGTCTA   360
CCAGGGGTGG GGAGAGCGGG GGCTGGAGGA CCACCCAGCC TCAGAGGCAG CTGGAGGCCT   420
GGGTGAACAG GACT                                                    434
```

( 2 ) INFORMATION FOR SEQ ID NO:6:

( i ) SEQUENCE CHARACTERISTICS:
( A ) LENGTH: 571 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

```
GACAGGCCTG GCATTCAGTG GCCAGGTGTT GCAGTGTCCC TGAGGAATAG CTTGGCTTGA    60
GGCCGTGGGG AGGGCTGCCG GCCAGCGCAC CCCCCCATGC CAGATGGTCA CCATGGCGTG   120
CATCTTCCAG CTCTTCGACT ACATCTCTGA GTGCATCTCC GACTTCCTGG ACAAGCATCA   180
GATGAAACAC AAGAAGCTGC CCCTGGGCTT CACCTTCTCC TTTCCTGTGA GGCACGAAGA   240
```

CATCGATAAG GTGGGCCGGG TGGAGGGGCA GAAGGCAGAT GAGGGGAGGC ACAGGCACCC 300

CAGAGGAACT CTGCCTTCAA ATGTAGCCCC CATACCCTGT GCTCAGAAGG GAGATCTGGA 360

TTCAAATTGT GGCCATGTCA CCTGCCACTC TAATGCTGTG GAAAAGAAGC ATCACATTAG 420

CTAATTCTGG CTGTGCGCCT TGTGAGGCAC CAGCTATGAT CACCCCACTC CAGTGGAAAG 480

AGCAGCTGGC AGTAGGGTGG GGCTCAAACT CAGGCAGCCG GCTCTGGGTC ATCAGCCAGT 540

CATGTCACAT GCCTATGCTA GTCAGAATGT G 571

( 2 ) INFORMATION FOR SEQ ID NO:7:

( i ) SEQUENCE CHARACTERISTICS:
( A ) LENGTH: 527 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

CCCTAGCACC CTGCCTCCAG ATATGTTAGC AGCCACGAGG CCTATCTCTC CCCACAGGGC 60

ATCCTTCTCA ACTGGACCAA GGGCATCAAG GCCTCAGGAG CAGAAGGGAA CAATGTCGTG 120

GGGCTTCTGC GAGACGCTAT CAAACGGAGA GGGGTGAGGG GGCACCTGTA CCTGCCGGGG 180

GGGCTGCCCT GGGCCACCCA CCCCAGCACT GCCTGCCTTT CTCCTTGGCT TCCAGCACTG 240

CAGCTTCTGT GCTTCTTGGC AGGACTTTGA AATGGATGTG GTGGCAATGG TGAATGACAC 300

GGTGGCCACG ATGATCTCCT GCTACTACGA AGACCATCAG TGCGAGGTCG GCATGATCGT 360

GGGTAAGGGC TCCTTGCACC CCTGCCCCTT CCAGACTGCC GAGGCTCCCT GTGTACAACA 420

GGCTTCAAGG GCCCTGTGGG TGAGGGCCAA ACTACTTAAC AACCGGTGAT GTCAGAGCAG 480

AGCCTGGTGC TACAGCCTGG GTGGTCTTGG GGTATCAAGA TGGAAGC 527

( 2 ) INFORMATION FOR SEQ ID NO:8:

( i ) SEQUENCE CHARACTERISTICS:
( A ) LENGTH: 492 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

GGCAGGAACC AGGCCCTACT CCGGGGCAGT GCAGCTCTCG CTGACAGTCC CCCCGACCTC 60

CACCCCAGGC ACGGGCTGCA ATGCCTGCTA CATGGAGGAG ATGCAGAATG TGGAGCTGGT 120

GGAGGGGGAC GAGGGCCGCA TGTGCGTCAA TACCGAGTGG GGCGCCTTCG GGGACTCCGG 180

CGAGCTGGAC GAGTTCCTGC TGGAGTATGA CCGCCTGGTG GACGAGAGCT CTGCAAACCC 240

CGGTCAGCAG CTGTAAGGAT GCCCCCCTCC CCCACAACCC AGGCCCTGGG CGCTCTGGTG 300

CAGCGGCAGA TGGGAGCCGG GCCATTGCAG ATAATGGGCT TGTTTTTAAA CAACTCTGGG 360

GAAAAGCAAA CTGACAATCC GTTCGTAAGC TCCATCCCTT CTGCTCAGTC ATGACCTGCC 420

CCTGTGAGAG ATGAAGGGTT AGTCCCAGTT GTGATGTGAT AAGCCCAGAC CTCTTTCCTT 480

CCGACAGGTG AT 492

( 2 ) INFORMATION FOR SEQ ID NO:9:

( i ) SEQUENCE CHARACTERISTICS:
( A ) LENGTH: 396 base pairs

-continued ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

```
CCTCAGTGGG GAGCACTGGG GCCGGCTCCC GGCTTCCACC TGCATGAGGG GCCCTCCCTC    60
GTGCCTGCTG ATGTAATGGT CCTGCCCTAT GTCCAGGTAT GAGAAGCTCA TAGGTGGCAA   120
GTACATGGGC GAGCTGGTGC GGCTTGTGCT GCTCAGGCTC GTGGACGAAA ACCTGCTCTT   180
CCACGGGGAG GCCTCCGAGC AGCTGCGCAC ACGCGGAGCC TTCGAGACGC GCTTCGTGTC   240
GCAGGTGGAG AGGTGTGCGG AGGAGGAGGG TGGGTGCAAA GGGCAGGGGC TGGGGTCGCC   300
CGGGCACTGC AGACTTGGTC TCAGGGCGAC GCTGAGTCCC AGGCCCGGGG CGCAGGGACG   360
GGAAACTAGG GCCTGGGGCG GGATTCCGGG CGTGGG                             396
```

( 2 ) INFORMATION FOR SEQ ID NO:10:

( i ) SEQUENCE CHARACTERISTICS:
( A ) LENGTH: 532 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

```
GCTGGGGGAC GGCTGGCCGG GGCCCCTCCC TGGAGAACGA GAGGCCGCCG CTGGAGGGGG    60
ATGGACTGTC GGAGCGACAC TCAGCGACCG CCCTACCTCC TCCCGCCCCG CAGCGACACG   120
GGCGACCGCA AGCAGATCTA CAACATCCTG AGCACGCTGG GGCTGCGACC CTCGACCACC   180
GACTGCGACA TCGTGCGCCG CGCCTGCGAG AGCGTGTCTA CGCGCGCTGC GCACATGTGC   240
TCGGCGGGGC TGGCGGGCGT CATCAACCGC ATGCGCGAGA GCCGCAGCGA GGACGTAATG   300
CGCATCACTG TGGGCGTGGA TGGCTCCGTG TACAAGCTGC ACCCCAGGTG AGCCTGCCCC   360
GCTCTCTCCC TGGTAAAGTG GGGCCCAAAA AGCGCGCGCT CCAAGGTTCC TTGCGGTTCC   420
CAAGCTCCAA GATTTCGTAG TCCTCTTCTC GTCCCCCTTG GCCTAGATTT GGGGGAAGGG   480
TCGACTGCGT GCAGGGCGCC CGGTAATGAA TGTGGAGGAT GAGGTGGGAG GA           532
```

( 2 ) INFORMATION FOR SEQ ID NO:11:

( i ) SEQUENCE CHARACTERISTICS:
( A ) LENGTH: 1128 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

```
TAGAGTCTTC TCGACCCCCT TGGCCTAGAT TTGGGGGAAG GGTCGACTGC GTGCAGGGCG    60
CCCGGTAATG AATGTGGAGG ATGAGGTGGG AGGAGGGACG GCAGCCCTGC TTCTCTTCTG   120
CCCAGCTTCA AGGAGCGGTT CCATGCCAGC GTGCGCAGGC TGACGCCCAG CTGCGAGATC   180
ACCTTCATCG AGTCGGAGGA GGGCAGTGGC CGGGGCGCGG CCCTGGTCTC GGCGGTGGCC   240
TGTAAGAAGG CCTGTATGCT GGGCCAGTGA GAGCAGTGGC CGCAAGCGCA GGGAGGATGC   300
CACAGCCCCA CAGCACCCAG GCTCCATGGG GAAGTGCTCC CCACACGTGC TCGCAGCCTG   360
GCGGGGCAGG AGGCCTGGCC TTGTCAGGAC CCAGGCCGCC TGCCATACCG CTGGGGAACA   420
```

-continued

| | | | | | | |
|---|---|---|---|---|---|---|
| GAGCGGGCCT | CTTCCCTCAG | TTTTTCGGTG | GGACAGCCCC | AGGGCCCTAA | CGGGGGTGCG | 480 |
| GCAGGAGCAG | GAACAGAGAC | TCTGGAAGCC | CCCCACCTTT | CTCGCTGGAA | TCAATTTCCC | 540 |
| AGAAGGGAGT | TGCTCACTCA | GGACTTTGAT | GCATTTCCAC | ACTGTCAGAG | CTGTTGGCCT | 600 |
| CGCCTGGGCC | CAGGCTCTGG | GAAGGGGTGC | CCTCTGGATC | CTGCTGTGGC | CTCACTTCCC | 660 |
| TGGGAACTCA | TCCTGTGTGG | GGAGGCAGCT | CCAACAGCTT | GACCAGACCT | AGACCTGGGC | 720 |
| CAAAAGGGCA | GCCAGGGGCT | GCTCATCACC | CAGTCCTGGC | CATTTTCTTG | CCTGAGGCTC | 780 |
| AAGAGGCCCA | GGGAGCAATG | GGAGGGGGCT | CCATGGAGGA | GGTGTCCCAA | GCTTTGAATA | 840 |
| CCCCCAGAGA | CCTTTTCTCT | CCCATACCAT | CACTGAGTGG | CTTGTGATTC | TGGGATGGAC | 900 |
| CCTCGCAGCA | GGTGCAAGAG | ACAGAGCCCC | CAAGCCTCTG | CCCCAAGGGG | CCCACAAAGG | 960 |
| GGAGAAGGGC | CAGCCCTACA | TCTTCAGCTC | CCATAGCGCT | GGCTCAGGAA | GAAACCCCAA | 1020 |
| GCAGCATTCA | GCACACCCCA | AGGGACAACC | CCATCATATG | ACATGCCACC | CTCTCCATGC | 1080 |
| CCAACCTAAG | ATTGTGTGGG | TTTTTTAATT | AAAAATGTTA | AAAGTTTT | | 1128 |

( 2 ) INFORMATION FOR SEQ ID NO:12:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

TCCACTTCAG AAGCCTACTG 20

( 2 ) INFORMATION FOR SEQ ID NO:13:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:13:

TCAGATTCTG AGGCTCAAAC 20

( 2 ) INFORMATION FOR SEQ ID NO:14:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

AGCAGGCAGG AGCATCTCTG 20

( 2 ) INFORMATION FOR SEQ ID NO:15:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:15:

GCTGCTCTCC CAGTGCAAAG 20

( 2 ) INFORMATION FOR SEQ ID NO:16:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

CCAGACTCTC CTCTGAACTC 20

( 2 ) INFORMATION FOR SEQ ID NO:17:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

GAAGAAGAGG TTCCATCTGA 20

( 2 ) INFORMATION FOR SEQ ID NO:18:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

TGCAGATGCC TGGTGACAGC 20

( 2 ) INFORMATION FOR SEQ ID NO:19:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

CACAGCTGCT TCTGGATGAG 20

( 2 ) INFORMATION FOR SEQ ID NO:20:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

TAATATCCGG CTCAGTCACC 20

( 2 ) INFORMATION FOR SEQ ID NO:21:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

CTGAGATCCT GCATGCCTTG 20

( 2 ) INFORMATION FOR SEQ ID NO:22:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

TAGCTTGGCT TGAGGCCGTG 20

( 2 ) INFORMATION FOR SEQ ID NO:23:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

TGAAGGCAGA GTTCCTCTGG 20

( 2 ) INFORMATION FOR SEQ ID NO:24:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:24:

GCAGCCACGA GGCCTATCTC 20

( 2 ) INFORMATION FOR SEQ ID NO:25:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:25:

GAGAAAGGCA GGCAGTGCTG 20

( 2 ) INFORMATION FOR SEQ ID NO:26:

( i ) SEQUENCE CHARACTERISTICS:
( A ) LENGTH: 20 base pairs
( B ) TYPE: nucleic acid ( C ) STRANDEDNESS: single
( D ) TOPOLOGY: linear ( i i ) MOLECULE TYPE: DNA ( genomic)

( x i ) SEQUENCE DESCRIPTION: SEQ ID NO:26:

CCAGCACTGC AGCTTCTGTG 20

( 2 ) INFORMATION FOR SEQ ID NO:27:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:27:

GAGCCTCGGC AGTCTGGAAG 20

( 2 ) INFORMATION FOR SEQ ID NO:28:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:28:

AGTGCAGCTC TCGCTGACAG 20

( 2 ) INFORMATION FOR SEQ ID NO:29:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:29:

CATCTGCCGC TGCACCAGAG 20

( 2 ) INFORMATION FOR SEQ ID NO:30:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:30:

TGCCTGCTGA TGTAATGGTC 20

( 2 ) INFORMATION FOR SEQ ID NO:31:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( qenomic)

( x i ) SEQUENCE DESCRIPTION: SEQ ID NO:31:

TGAGACCAAG TCTGCAGTGC 20

( 2 ) INFORMATION FOR SEQ ID NO:32:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:32:

ACTGTCGGAG CGACACTCAG 20

( 2 ) INFORMATION FOR SEQ ID NO:33:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:33:

CTTGGAGCTT GGGAACCGCA 20

( 2 ) INFORMATION FOR SEQ ID NO:34:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( genomic)

( x i ) SEQUENCE DESCRIPTION: SEQ ID NO:34:

GTCGACTGCG TGCAGGGCGC 20

( 2 ) INFORMATION FOR SEQ ID NO:35:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:35:

TGTGGCATCC TCCCTGCGCT 20

( 2 ) INFORMATION FOR SEQ ID NO:36:

( i ) SEQUENCE CHARACTERISTICS:
( A ) LENGTH: 3618 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:36:

CATATACTTA ACTGTTATAT AGATACCACA TTATTTATCC AGTAGCATTT TTAAAACTCC 60

AGTATCTACA GTAACTATTC GTTACGGACA CTAAGCCCCA CAGCTCAACA CAACCAGGAG 120

-continued

```
AGAAAGCGCT GAGGACGCCA CCCAAGCGCC CAGCAATGGC CCTGCCTGGA GAACATCCAG   180
GCTCAGTGAG GAAGGGTCCA GAAGGGAATG CTTGCCGACT CGTTGGAGAA CAATGAAAAG   240
GAGGAAACTG TGACTGAACC TCAAACCCCA AACCAGCCCG AGGAGAACCA CATTCTCCCA   300
GGGACCCAGG GCGGGCCGTG ACCCCTGCGG CGGAGAAGCC TTGGATATTT CCACTTCAGA   360
AGCCTACTGG GGAAGGCTGA GGGGTCCCAG CTCCCCACGC TGGCTGCTGT GCAGATGCTG   420
GACGACAGAG CCAGGATGGA GGCCGCCAAG AAGGAGAAGG TAGAGCAGAT CCTGGCAGAG   480
TTCCAGCTGC AGGAGGAGGA CCTGAAGAAG GTGATGAGAC GGATGCAGAA GGAGATGGAC   540
CGCGGCCTGA GGCTGGAGAC CCATGAAGAG GCCAGTGTGA AGATGCTGCC CACCTACGTG   600
CGCTCCACCC CAGAAGGCTC AGAAGTCGGG GACTTCCTCT CCCTGGACCT GGGTGGCACT   660
AACTTCAGGG TGATGCTGGT GAAGGTGGGA GAAGGTGAGG AGGGGCAGTG GAGCGTGAAG   720
ACCAAACACC AGATGTACTC CATCCCCGAG GACGCCATGA CCGGCACTGC TGAGATGCTC   780
TTCGACTACA TCTCTGAGTG CATCTCCGAC TTCCTGGACA AGCATCAGAT GAAACACAAG   840
AAGCTGCCCC TGGGCTTCAC CTTCTCCTTT CCTGTGAGGC ACGAAGACAT CGATAAGGGC   900
ATCCTTCTCA ACTGGACCAA GGGCATCAAG GCCTCAGGAG CAGAAGGGAA CAATGTCGTG   960
GGGCTTCTGC GAGACGCTAT CAAACGGAGA GGGGACTTTG AAATGGATGT GGTGGCAATG  1020
GTGAATGACA CGGTGGCCAC GATGATCTCC TGCTACTACG AAGACCATCA GTGCGAGGTC  1080
GGCATGATCG TGGGCACGGG CTGCAATGCC TGCTACATGG AGGAGATGCA GAATGTGGAG  1140
CTGGTGGAGG GGGACGAGGG CCGCATGTGC GTCAATACCG AGTGGGGCGC CTTCGGGGAC  1200
TCCGGCGAGC TGGACGAGTT CCTGCTGGAG TATGACCGCC TGGTGGACGA GAGCTCTGCA  1260
AACCCCGGTC AGCAGCTGTA TGAGAAGCTC ATAGGTGGCA AGTACATGGG CGAGCTGGTG  1320
CGGCTTGTGC TGCTCAGGCT CGTGGACGAA AACCTGCTCT TCCACGGGGA GGCCTCCGAG  1380
CAGCTGCGCA CACGCGGAGC CTTCGAGACG CGCTTCGTGT CGCAGGTGGA GAGCGACACG  1440
GGCGACCGCA AGCAGATCTA CAACATCCTG AGCACGCTGG GGCTGCGACC CTCGACCACC  1500
GACTGCGACA TCGTGCGCCG CGCCTGCGAG AGCGTGTCTA CGCGCGCTGC GCACATGTGC  1560
TCGGCGGGGC TGGCGGGCGT CATCAACCGC ATGCGCGAGA GCCGCAGCGA GGACGTAATG  1620
CGCATCACTG TGGGCGTGGA TGGCTCCGTG TACAAGCTGC ACCCCAGCTT CAAGGAGCGG  1680
TTCCATGCCA GCGTGCGCAG GCTGACGCCC AGCTGCGAGA TCACCTTCAT CGAGTCGGAG  1740
GAGGGCAGTG GCCGGGGCGC GGCCCTGGTC TCGGCGGTGG CCTGTAAGAA GGCCTGTATG  1800
CTGGGCCAGT GAGAGCAGTG GCCGCAAGCG CAGGGAGGAT GCCACAGCCC CACAGCACCC  1860
AGGCTCCATG GGGAAGTGCT CCCCACACGT GCTCGCAGCC TGGCGGGGCA GGAGGCCTGG  1920
CCTTGTCAGG ACCCAGGCCG CCTGCCATAC CGCTGGGGAA CAGAGCGGGC CTCTTCCCTC  1980
AGTTTTTCGG TGGGACAGCC CCAGGGCCCT AACGGGGGTG CGGCAGGAGC AGGAACAGAG  2040
ACTCTGGAAG CCCCCCACCT TTCTCGCTGG AATCAATTTC CCAGAAGGGA GTTGCTCACT  2100
CAGGACTTTG ATGCATTTCC ACACTGTCAG AGCTGTTGGC CTCGCCTGGG CCCAGGCTCT  2160
GGGAAGGGGT GCCCTCTGGA TCCTGCTGTG GCCTCACTTC CCTGGGAACT CATCCTGTGT  2220
GGGGAGGCAG CTCCAACAGC TTGACCAGAC CTAGACCTGG GCCAAAAGGG CAGCCAGGGG  2280
CTGCTCATCA CCCAGTCCTG GCCATTTTCT TGCCTGAGGC TCAAGAGGCC CAGGGAGCAA  2340
TGGGAGGGGG CTCCATGGAG GAGGTGTCCC AAGCTTTGAA TACCCCCAGA GACCTTTTCT  2400
CTCCCATACC ATCACTGAGT GGCTTGTGAT TCTGGGATGG ACCCTCGCAG CAGGTGCAAG  2460
AGACAGAGCC CCCAAGCCTC TGCCCCAAGG GGCCCACAAA GGGGAGAAGG GCCAGCCCTA  2520
```

-continued

```
CATCTTCAGC TCCCATAGCG CTGGCTCAGG AAGAAACCCC AAGCAGCATT CAGCACACCC 2580
CAAGGGACAA CCCCATCATA TGACATGCCA CCCTCTCCAT GCCCAACCTA AGATTGTGTG 2640
GGTTTTTTAA TTAAAAATGT TAAAAGTTTT TTCTTATTGT TATGTCTCAT ATAGATCTAC 2700
ATCTACACCG TTTAACATTA TTACAACAAC CTTATATTAC AACAACCTTC TCATATTTTA 2760
TAGATCTACA TCTACTTATA TAGATACCAC ACTTTATTAA ATTATTAAAT TTATTAAAAA 2820
TTATTAACAT ATTATTAAAA ATTTAAGTTT AATTTAACAT TTAATTTAAA TTTAACATAT 2880
TATTTTATTA AATTATTAAA TTTATTAAAA ATTATTAACA TATTATTAAA AATTTAAGTT 2940
TAATTTAACA TTTAATTTAA ATTTAACTTT AACCTTATCC TTATTGTTAT GTCTATTATA 3000
CTTAAAGCAT TATAACTTTC ATTAACATCT ACGCACACAC AATTCGTCAT ATTTCATATT 3060
TCATAATGAT ATTATATAGC TTATATTAAC TTATAAGTAA CTTATATATA TACTTATATA 3120
GATACCACAC TTATTTATCC AGTAGCATTT TTAAAACTCC AGTATCTACA TTATATAATA 3180
CCTTCTCATA TTTAACTAAT TTAAAAGTAT TGGGGTGGGT ATGTACGTGT GAGAGGAGAT 3240
ATCCGGTGCA CGGCTGAGGA GGGGGATGAT TGTGTTCACT AACAGAGTGG ATCTGGGAAA 3300
ACACGTTATA TAGATACCAC ACTCATAACT GTGCATCTAC AATCATATAG CAGCAAACAA 3360
ACATAAAAAT AAATAGTGTA ATAACATCTA CGCACACATC AATTCGTCAA AGTTTTATTA 3420
TAAGAAGCAT TTTCCAGAAA CCAGAACCCT ATAGATCTAC ATCCCCTACC CACCCACCAA 3480
GCCCCAAATA ATTTCATATC TCTGCAAACT AATATAAAAG TATTGGGGTG GGTATGTACG 3540
TGTGAGAGGA GATATCCGGT GCACGGCTGA GGAGGGGGAT GATTGTGTTC ACTAACAGAG 3600
TGGATCTGGG AAAACACG 3618
```

( 2 ) INFORMATION FOR SEQ ID NO:37:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:37:

```
GTCGAGCAGA TCCTGGCAGA G 21
```

( 2 ) INFORMATION FOR SEQ ID NO:38:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:38:

```
TGGTCCAGTT GAGAAGGAAG 20
```

( 2 ) INFORMATION FOR SEQ ID NO:39:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:39:

CTCTGCCAGG ATCTGCTCTA C 21

( 2 ) INFORMATION FOR SEQ ID NO:40:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:40:

AGTGCAGCTC TCGCTGACAG 20

( 2 ) INFORMATION FOR SEQ ID NO:41:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:41:

CATCTGCGCT GCACAGAG 18

( 2 ) INFORMATION FOR SEQ ID NO:42:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:42:

CATGTGCGTC ATACGAGT 18

( 2 ) INFORMATION FOR SEQ ID NO:43:

( i ) SEQUENCE CHARACTERISTICS:
( A ) LENGTH: 183 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..183

( x i ) SEQUENCE DESCRIPTION: SEQ ID NO:43:

```
ACG GGC TGC AAT GCC TGC TAC ATG GAG GAG ATG CAG AAT GTG GAG CTG     48
Thr Gly Cys Asn Ala Cys Tyr Met Glu Glu Met Gln Asn Val Glu Leu
  1                 5                  10                  15

GTG GAG GGG GAC GAG GGC CGC ATG TGC GTC AAT ACC GAG TGG GGC GCC     96
Val Glu Gly Asp Glu Gly Arg Met Cys Val Asn Thr Glu Trp Gly Ala
             20                  25                  30

TTC GGG GAC TCC GGC GAG CTG GAC GAG TTC CTG CTG GAG TAT GAC CGC    144
Phe Gly Asp Ser Gly Glu Leu Asp Glu Phe Leu Leu Glu Tyr Asp Arg
         35                  40                  45

CTG GTG GAC GAG AGC TCT GCA AAC CCC GGT CAG CAG CTG                183
Leu Val Asp Glu Ser Ser Ala Asn Pro Gly Gln Gln Leu
```

-continued 50 55 60

( 2 ) INFORMATION FOR SEQ ID NO:44:

( i ) SEQUENCE CHARACTERISTICS:
( A ) LENGTH: 61 amino acids
( B ) TYPE: amino acid
( D ) TOPOLOGY: linear ( i i ) MOLECULE TYPE: protein ( x i ) SEQUENCE DESCRIPTION: SEQ ID NO:44:

Thr Gly Cys Asn Ala Cys Tyr Met Glu Glu Met Gln Asn Val Glu Leu
1 5 10 15

Val Glu Gly Asp Glu Gly Arg Met Cys Val Asn Thr Glu Trp Gly Ala
20 25 30

Phe Gly Asp Ser Gly Glu Leu Asp Glu Phe Leu Leu Glu Tyr Asp Arg
35 40 45

Leu Val Asp Glu Ser Ser Ala Asn Pro Gly Gln Gln Leu
50 55 60

( 2 ) INFORMATION FOR SEQ ID NO:45:

( i ) SEQUENCE CHARACTERISTICS:
( A ) LENGTH: 156 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..156

( x i ) SEQUENCE DESCRIPTION: SEQ ID NO:45:

TAT GAG AAG CTC ATA GGT GGC AAG TAC ATG GGC GAG CTG GTG CGG CTT 48
Tyr Glu Lys Leu Ile Gly Gly Lys Tyr Met Gly Glu Leu Val Arg Leu
1 5 10 15

GTG CTG CTC AGG CTC GTG GAC GAA AAC CTG CTC TTC CAC GGG GAG GCC 96
Val Leu Leu Arg Leu Val Asp Glu Asn Leu Leu Phe His Gly Glu Ala
20 25 30

TCC GAG CAG CTG CGC ACA CGC GGA GCC TTC GAG ACG CGC TTC GTG TCG 144
Ser Glu Gln Leu Arg Thr Arg Gly Ala Phe Glu Thr Arg Phe Val Ser
35 40 45

CAG GTG GAG AGC 156
Gln Val Glu Ser
50

( 2 ) INFORMATION FOR SEQ ID NO:46:

( i ) SEQUENCE CHARACTERISTICS:
( A ) LENGTH: 52 amino acids
( B ) TYPE: amino acid
( D ) TOPOLOGY: linear ( i i ) MOLECULE TYPE: protein ( x i ) SEQUENCE DESCRIPTION: SEQ ID NO:46:

Tyr Glu Lys Leu Ile Gly Gly Lys Tyr Met Gly Glu Leu Val Arg Leu
1 5 10 15

Val Leu Leu Arg Leu Val Asp Glu Asn Leu Leu Phe His Gly Glu Ala
20 25 30

Ser Glu Gln Leu Arg Thr Arg Gly Ala Phe Glu Thr Arg Phe Val Ser
35 40 45

Gln Val Glu Ser
50

( 2 ) INFORMATION FOR SEQ ID NO:47:

( i ) SEQUENCE CHARACTERISTICS:
( A ) LENGTH: 465 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:47:

Met Leu Asp Asp Arg Ala Arg Met Glu Ala Ala Lys Lys Glu Lys Val
1 5 10 15

Glu Gln Ile Leu Ala Glu Phe Gln Leu Gln Glu Glu Asp Leu Lys Lys
20 25 30

Val Met Arg Arg Met Gln Lys Glu Met Asp Arg Gly Leu Arg Leu Glu
35 40 45

Thr His Glu Glu Ala Ser Val Lys Met Leu Pro Thr Tyr Val Arg Ser
50 55 60

Thr Pro Glu Gly Ser Gln Val Gly Asp Phe Leu Ser Leu Asp Leu Gly
65 70 75 80

Gly Thr Asn Phe Arg Val Met Leu Val Lys Val Gly Glu Gly Glu Glu
85 90 95

Gly Gln Trp Ser Val Lys Thr Lys His Gln Met Tyr Ser Ile Pro Glu
100 105 110

Asp Ala Met Thr Gly Thr Ala Glu Met Leu Phe Asp Tyr Ile Ser Glu
115 120 125

Cys Ile Ser Asp Phe Leu Asp Lys His Gln Met Lys His Lys Lys Leu
130 135 140

Pro Leu Gly Phe Thr Phe Ser Phe Pro Val Arg His Glu Asp Ile Asp
145 150 155 160

Lys Gly Ile Leu Leu Asn Trp Thr Lys Gly Ile Lys Ala Ser Gly Ala
165 170 175

Glu Gly Asn Asn Val Val Gly Leu Leu Arg Asp Ala Ile Lys Arg Arg
180 185 190

Gly Asp Phe Glu Met Asp Val Val Ala Met Val Asn Asp Thr Val Ala
195 200 205

Thr Met Ile Ser Cys Tyr Tyr Glu Asp His Gln Cys Glu Val Gly Met
210 215 220

Ile Val Gly Thr Gly Cys Asn Ala Cys Tyr Met Glu Glu Met Gln Asn
225 230 235 240

Val Glu Leu Val Glu Gly Asp Glu Gly Arg Met Cys Val Asn Thr Glu
245 250 255

Trp Gly Ala Phe Gly Asp Ser Gly Glu Leu Asp Glu Phe Leu Leu Glu
260 265 270

Tyr Asp Arg Leu Val Asp Glu Ser Ser Ala Asn Pro Gly Gln Gln Leu
275 280 285

Tyr Glu Lys Leu Ile Gly Gly Lys Tyr Met Gly Glu Leu Val Arg Leu
290 295 300

Val Leu Leu Arg Leu Val Asp Glu Asn Leu Leu Phe His Gly Glu Ala
305 310 315 320

Ser Glu Gln Leu Arg Thr Arg Gly Ala Phe Glu Thr Arg Phe Val Ser
325 330 335

Gln Val Glu Ser Asp Thr Gly Asp Arg Lys Gln Ile Tyr Asn Ile Leu

-continued 340 345 350

Ser Thr Leu Gly Leu Arg Pro Ser Thr Thr Asp Cys Asp Ile Val Arg
355 360 365

Arg Ala Cys Glu Ser Val Ser Thr Arg Ala Ala His Met Cys Ser Ala
370 375 380

Gly Leu Ala Gly Val Ile Asn Arg Met Arg Glu Ser Arg Ser Glu Asp
385 390 395 400

Val Met Arg Ile Thr Val Gly Val Asp Gly Ser Val Tyr Lys Leu His
405 410 415

Pro Ser Phe Lys Glu Arg Phe His Ala Ser Val Arg Arg Leu Thr Pro
420 425 430

Ser Cys Glu Ile Thr Phe Ile Glu Ser Glu Glu Gly Ser Gly Arg Gly
435 440 445

Ala Ala Leu Val Ser Ala Val Ala Cys Lys Lys Ala Cys Met Leu Gly
450 455 460

Gln
465

( 2 ) INFORMATION FOR SEQ ID NO:48:

( i ) SEQUENCE CHARACTERISTICS:
( A ) LENGTH: 486 amino acids
( B ) TYPE: amino acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:48:

Met Val His Leu Gly Pro Lys Lys Pro Gln Ala Arg Lys Gly Ser Met
1 5 10 15

Ala Asp Val Pro Lys Glu Leu Met Gln Gln Ile Glu Asn Phe Glu Lys
20 25 30

Asn Phe Thr Val Pro Thr Glu Thr Leu Gln Ala Val Thr Lys His Phe
35 40 45

Ile Ser Glu Leu Glu Lys Gly Leu Ser Lys Lys Gly Gly Asn Ile Pro
50 55 60

Met Ile Pro Gly Trp Val Met Asp Phe Pro Thr Gly Lys Glu Ser Gly
65 70 75 80

Asp Phe Leu Ala Ile Asp Leu Gly Gly Thr Asn Leu Arg Val Val Leu
85 90 95

Val Lys Leu Gly Gly Asp Arg Thr Phe Asp Thr Thr Gln Ser Lys Tyr
100 105 110

Arg Leu Pro Asp Ala Met Arg Thr Thr Gln Asn Pro Asp Glu Leu Trp
115 120 125

Glu Phe Ile Ala Asp Ser Leu Lys Ala Phe Ile Asp Glu Gln Phe Pro
130 135 140

Gln Gly Ile Ser Glu Pro Ile Pro Leu Gly Phe Thr Phe Ser Phe Pro
145 150 155 160

Ala Ser Gln Asn Lys Ile Asn Glu Gly Ile Leu Gln Arg Trp Thr Lys
165 170 175

Gly Phe Asp Ile Pro Asn Ile Glu Asn His Asp Val Val Pro Met Leu
180 185 190

Gln Lys Gln Ile Thr Lys Arg Asn Ile His Ile Glu Val Val Ala Leu
195 200 205

Ile Asn Asp Thr Thr Gly Thr Leu Val Ala Ser Tyr Tyr Thr Asp Pro
210 215 220

-continued

| | | | | | | | | | | | | | | | |
|---|---|---|---|---|---|---|---|---|---|---|---|---|---|---|---|
| Glu | Thr | Lys | Met | Gly | Val | Ile | Phe | Gly | Thr | Gly | Val | Asn | Gly | Ala | Tyr |
| 225 | | | | | 230 | | | | | 235 | | | | | 240 |
| Tyr | Asp | Val | Cys | Ser | Asp | Ile | Glu | Lys | Leu | Gln | Gly | Lys | Leu | Ser | Asp |
| | | | | 245 | | | | | 250 | | | | | 255 | |
| Asp | Ile | Pro | Pro | Ser | Ala | Pro | Met | Ala | Ile | Asn | Cys | Glu | Tyr | Gly | Ser |
| | | | 260 | | | | | 265 | | | | | 270 | | |
| Phe | Asp | Asn | Glu | His | Val | Val | Leu | Pro | Arg | Thr | Lys | Tyr | Asp | Ile | Thr |
| | | 275 | | | | | 280 | | | | | 285 | | | |
| Ile | Asp | Glu | Glu | Ser | Pro | Arg | Pro | Gly | Gln | Gln | Thr | Phe | Glu | Lys | Met |
| | 290 | | | | | 295 | | | | | 300 | | | | |
| Ser | Ser | Gly | Tyr | Tyr | Leu | Gly | Phe | Ile | Leu | Arg | Ile | Ala | Leu | Met | Asp |
| 305 | | | | | 310 | | | | | 315 | | | | | 320 |
| Met | Tyr | Lys | Gln | Gly | Phe | Ile | Phe | Lys | Asn | Gln | Asp | Leu | Ser | Lys | Phe |
| | | | | 325 | | | | | 330 | | | | | 335 | |
| Asp | Lys | Pro | Phe | Val | Met | Asp | Thr | Ser | Tyr | Pro | Ala | Arg | Ile | Glu | Glu |
| | | | 340 | | | | | 345 | | | | | 350 | | |
| Asp | Pro | Phe | Glu | Asn | Leu | Glu | Asp | Thr | Asp | Asp | Leu | Phe | Gln | Asn | Glu |
| | | 355 | | | | | 360 | | | | | 365 | | | |
| Phe | Gly | Ile | Asn | Thr | Thr | Val | Gln | Glu | Arg | Lys | Leu | Ile | Arg | Arg | Leu |
| | 370 | | | | | 375 | | | | | 380 | | | | |
| Ser | Phe | Leu | Ile | Gly | Ala | Arg | Ala | Ala | Arg | Leu | Ser | Val | Cys | Gly | Ile |
| 385 | | | | | 390 | | | | | 395 | | | | | 400 |
| Ala | Ala | Ile | Cys | Gln | Lys | Arg | Gly | Tyr | Lys | Thr | Gly | His | Ile | Ala | Ala |
| | | | | 405 | | | | | 410 | | | | | 415 | |
| Asp | Gly | Ser | Val | Ser | Thr | Arg | Tyr | Pro | Gly | Phe | Lys | Glu | Lys | Ala | Ala |
| | | | 420 | | | | | 425 | | | | | 430 | | |
| Asn | Ala | Leu | Lys | Asp | Ile | Tyr | Gly | Trp | Thr | Gln | Pro | His | Leu | Asp | Asp |
| | | 435 | | | | | 440 | | | | | 445 | | | |
| Tyr | Pro | Ile | Lys | Val | Val | Pro | Ala | Glu | Asp | Gly | Ser | Gly | Pro | Gly | Ala |
| | 450 | | | | | 455 | | | | | 460 | | | | |
| Ala | Val | Ile | Ala | Ala | Leu | Ala | Gln | Lys | Arg | Ile | Ala | Glu | Gly | Lys | Ser |
| 465 | | | | | 470 | | | | | 475 | | | | | 480 |
| Val | Gly | Ile | Ile | Gly | Ala | | | | | | | | | | |
| | | | | 485 | | | | | | | | | | | |